US007763644B2

(12) United States Patent
Kenda et al.

(10) Patent No.: US 7,763,644 B2
(45) Date of Patent: Jul. 27, 2010

(54) IMIDAZOLE DERIVATIVES, PROCESSES FOR PREPARING THEM AND THEIR USES

(75) Inventors: Benoît Kenda, La Bruyère (BE); Philippe Michel, Beersel (BE); Yannick Quesnel, Lasne (BE)

(73) Assignee: UCB Pharma, S.A., Brussels (BE)

( * ) Notice: Subject to any disclaimer, the term of this patent is extended or adjusted under 35 U.S.C. 154(b) by 97 days.

(21) Appl. No.: 11/808,558

(22) Filed: Jun. 11, 2007

(65) Prior Publication Data

US 2008/0081832 A1 Apr. 3, 2008

Related U.S. Application Data

(62) Division of application No. 10/999,217, filed on Nov. 30, 2004, now Pat. No. 7,244,747.

(30) Foreign Application Priority Data

Dec. 2, 2003 (EP) .................................. 03027614

(51) Int. Cl.
*A61K 31/4184* (2006.01)
*C07D 403/06* (2006.01)

(52) U.S. Cl. .................................... 514/394; 548/306.1

(58) Field of Classification Search .............. 548/300.1, 548/301.7, 302.7, 304.4, 306.1; 514/394
See application file for complete search history.

(56) References Cited

U.S. PATENT DOCUMENTS

| | | | |
|---|---|---|---|
| 3,903,110 | A | 9/1975 | Freyermuth et al. |
| 4,178,167 | A | 12/1979 | Schneider et al. |
| 4,216,221 | A | 8/1980 | de Lannoy |

FOREIGN PATENT DOCUMENTS

| | | |
|---|---|---|
| GB | 1519914 | 8/1978 |
| WO | WO 93/07141 | 4/1993 |
| WO | WO 01/62726 | 8/2001 |

OTHER PUBLICATIONS

"Tautomer." Retrieved online via the Internet [Jan. 14, 2009]. URL: http://en.wikipedia.org/wiki/Tautomer.*

Belavin, I. Yu. Trimethylchlorosilane-catalyzed attachment of azole derivatives to 1-vinylpyrrolidone-2 and pharmacological activity of resultants. Khimiko-Farmatsevticheskii Zhurnal 26(9-10) (1992) 74-6.*

Abe et al. "A novel class of orally active non-peptide bradykinin B2 receptor antagonists. 2. Overcoming the species difference between guinea pig and man" J Med Chem. 41(21):4053-4061 (1998).

Beilstein Registry No. 6740745, Database Beilstein Crossfire Beilstein-Institut zur Foerderung der Wissenschaften, Frankfurt am Main, DE, abstract & Kumar et al. Journal of the Indian Chemical Society, 62(3): 257-259 (1985) [XP002270762].

Database Chemabs 'Online! Chemical Abstracts Service, Columbus, Ohio, US; Belavin, I. Yu. et al: "Trimethylchlorosilane-catalyzed attachment of azole derivatives to 1-vinylpyrrolidone-2 and pharmacological activity of resultants" retrieved from STN Database accession No. 1993: 539168 abstract & Khimiko-Farmatsevticheskii Zhurnal, 26(9-10), 74-6 Coden: Khfzan; ISSN: 0023-1134, 1992 [XP002270761].

Gouliaev et al. "Piracetam and other structurally related nootropics" Brain Research Reviews, Elsevier, XX, 19(2): 180-222 (1994).

Heine et al. "On Cyclic Intermediates in Substitution Reactions VII . The Alkaline Solvolysis of Some N-Ary1-4-bromobutanamides" Journal of the American Chemical Society, American Chemical Society, Washington, DC, US, 77:5420-5422 (1955).

Lions et al. "Sexadentate Chelate Compounds. X." Journal of the American Chemical Society, American Chemical Society, Washington, DC, US, 80: 3858-3865 (1958).

Weitzel et al. "Cytostatische Effekte von Imidazothion und dessen Derivaten" Hoppe-Seyler's Zeitschrift Fuer Physiologische Chemie, Walter de Gruyter, Berlin, DE, 346(2): 208-223 (1966).

* cited by examiner

*Primary Examiner*—Kamal A Saeed
*Assistant Examiner*—Samantha L Shterengarts
(74) *Attorney, Agent, or Firm*—Morgan, Lewis & Bockius LLP

(57) ABSTRACT

The present invention relates to imidazole derivatives, processes for preparing them, pharmaceutical compositions containing them and their use as pharmaceuticals.

9 Claims, 2 Drawing Sheets

IMIDAZOLE DERIVATIVES, PROCESSES FOR PREPARING THEM AND THEIR USES

RELATED APPLICATIONS

The present application is a divisional of U.S. application Ser. No. 10/999,217, filed Nov. 30, 2004 now U.S. Pat. No. 7,244,747 (now allowed), which claims the benefit of European Patent Application No. 03027614.1, filed Dec. 2, 2003, all of which are herein incorporated by reference in their entirety.

BACKGROUND OF THE INVENTION

The present invention concerns imidazole derivatives, processes for preparing them, pharmaceutical compositions containing them and their use as pharmaceuticals.

European Patent No. 0 162 036 B1 discloses compound (S)-α-ethyl-2-oxo-1-pyrrolidine acetamide, which is known under the International Nonproprietary Name of levetiracetam.

Levetiracetam, a levorotary compound, is disclosed as a protective agent for the treatment and prevention of hypoxic and ischemic type aggressions of the central nervous system. This compound is also effective in the treatment of epilepsy, a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (Gower A. J. et al., Eur. J. Pharmacol. (1992), 222, 193-203).

Belavin I. Yu. et al. (Khimiko-Farmatsevticheskii Zhurnal (1992), 26 (9-10), 74-76) discloses 1-[1-(1H-benzimidazol-1-yl)ethyl]-2-pyrrolidinone and its anticonvulsant activity.

DETAILED DESCRIPTION OF THE INVENTION

It has now surprisingly been found that certain imidazole derivatives demonstrate markedly improved therapeutic properties.

In one aspect the invention therefore provides a compound having the formula I or a pharmaceutically acceptable salt thereof, (I)

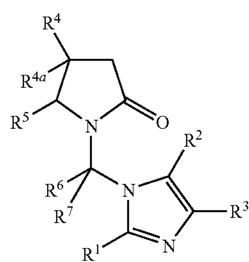

wherein $R^1$ is hydrogen, $C_{1-20}$ alkyl, $C_{3-8}$ cycloalkyl, halogen, hydroxy, alkoxy, aryloxy, ester, amido, cyano, nitro, amino, guanidine, amino derivative, alkylthio, arylthio, alkylsulfonyl, arylsulfonyl, alkylsulfinyl, arylsulfinyl, aryl or heterocycle;

$R^2$ is hydrogen, $C_{1-20}$ alkyl, alkoxy, amino, halogen, hydroxy, ester, amido, nitro, cyano, carbamate, or aryl;

$R^3$ is hydrogen, $C_{1-20}$ alkyl, alkoxy, amino, halogen, hydroxy, ester, amido, nitro, cyano, carbamate, or aryl;

or $R^2$ and $R^3$ can form together with the imidazole ring the following 1H-benzimidazole cycle

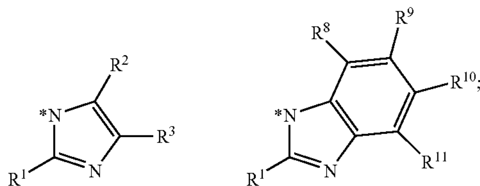

$R^4$ is hydrogen, $C_{1-20}$ alkyl, $C_{2-12}$ alkenyl, $C_{2-12}$ alkynyl, aryl, azido, alkoxycarbonylamino, arylsulfonyloxy or heterocycle;

$R^{4a}$ is hydrogen or $C_{1-20}$ alkyl;

or $R^4$ and $R^{4a}$ can form together a $C_{3-8}$ cycloalkyl;

$R^5$ is hydrogen;

or $R^4$, $R^{4a}$ and $R^5$ can form together with the 2-oxo-1-pyrrolidine ring the following 1,3-dihydro-2H-indol-2-one cycle

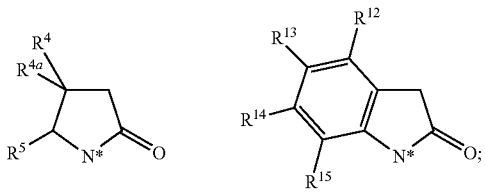

$R^6$ is hydrogen or $C_{1-20}$ alkyl;

$R^7$ is hydrogen;

or $R^6$ and $R^7$ are linked together to form a $C_{3-6}$ cycloalkyl;

$R^8$ is hydrogen, halogen, nitro, cyano, $C_{1-20}$ alkyl or alkoxy;

$R^9$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{10}$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{11}$ is hydrogen, halogen, nitro, cyano, $C_{1-20}$ alkyl or alkoxy;

$R^{12}$ is hydrogen or halogen;

$R^{13}$ is hydrogen, nitro, halogen, heterocycle, amino, aryl, $C_{1-20}$ alkyl unsubstituted or substituted by halogen, or alkoxy unsubstituted or substituted by halogen;

$R^{14}$ is hydrogen, $C_{1-20}$ alkyl or halogen;

$R^{15}$ is hydrogen, $C_{1-20}$ alkyl or halogen;

with the proviso that $R^4$ is different from hydrogen when

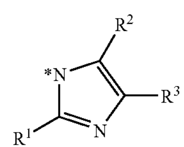

represents a group of formula

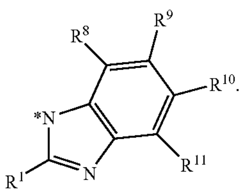

The asterisk * indicates the point of attachment of the substituents.

In a preferred embodiment, the invention concerns a compound having the formula I, their tautomers, geometrical isomers (including cis and trans, Z and E isomers), enantiomers, diastereoisomers and mixtures thereof (including all possible mixtures of stereoisomers), or pharmaceutically acceptable salts thereof, (I)

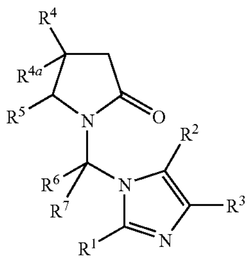

wherein $R^1$ is hydrogen, $C_{1-20}$ alkyl, $C_{3-8}$ cycloalkyl, halogen, hydroxy, ester, amido, cyano, nitro, amino, guanidine, alkylthio, alkylsulfonyl, alkylsulfinyl, aryl or heterocycle;

$R^2$ is hydrogen, $C_{1-20}$ alkyl, halogen, cyano, ester, carbamate or amido;

$R^3$ is hydrogen, cyano, $C_{1-20}$ alkyl, halogen or ester;

or $R^2$ and $R^3$ can form together with the imidazole ring the following 1H-benzimidazole cycle

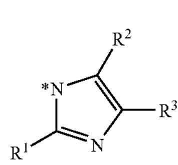

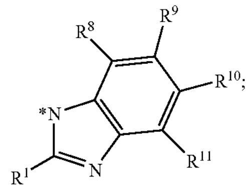

$R^4$ is hydrogen, $C_{1-20}$ alkyl, $C_{2-12}$ alkenyl or aryl;

$R^{4a}$ is hydrogen;

$R^5$ is hydrogen;

or $R^4$, $R^{4a}$ and $R^5$ can form together with the 2-oxo-1-pyrrolidine ring the following 1,3-dihydro-2H-indol-2-one cycle

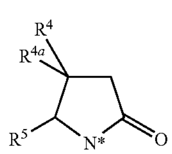

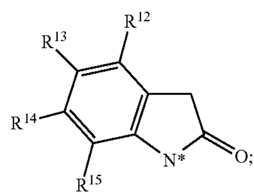

$R^6$ is hydrogen or $C_{1-20}$ alkyl;

$R^7$ is hydrogen;

or $R^6$ and $R^7$ are linked together to form a $C_{3-6}$ cycloalkyl;

$R^8$ is hydrogen;

$R^9$ is hydrogen, $C_{1-20}$ alkyl, halogen or alkoxy;

$R^{10}$ is hydrogen, $C_{1-20}$ alkyl, halogen or cyano;

$R^{11}$ is hydrogen;

$R^{12}$ is hydrogen or halogen;

$R^{13}$ is hydrogen, halogen, heterocycle or $C_{1-20}$ alkyl;

$R^{14}$ is hydrogen;

$R^{15}$ is hydrogen;

with the proviso that $R^4$ is different from hydrogen when

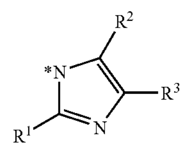

represents a group of formula

The term "alkyl", as used herein, represents saturated, monovalent hydrocarbon radicals having straight (unbranched) or branched or cyclic or combinations thereof and containing 1-20 carbon atoms, preferably 1-10 carbon atoms, more preferably 1-4 carbon atoms; most preferred alkyl groups have 1-3 carbon atoms. Alkyl moieties may optionally be substituted by 1 to 5 substituents independently selected from the group consisting of halogen, hydroxy, cyano, azido, aryloxy, alkoxy, alkylthio, alkanoylamino, arylcarbonylamino, aminocarbonyl, methylaminocarbonyl, dimethylaminocarbonyl or aryl. Usually alkyl groups, in the present case, are methyl, ethyl, n-propyl, i-propyl, n-butyl, i-butyl, t-butyl, 1-ethylpropyl, n-heptyl, 2,4,4-trimethylpentyl, n-decyl, chloromethyl, trifluoromethyl, 2-bromo-2,2-difluoroethyl, 2,2,2-trifluoroethyl, 3,3,3-trifluoropropyl, hydroxymethyl, cyanomethyl, azidomethyl, (acetylamino)methyl, (propionylamino)methyl, (benzoylamino)methyl, (4-chlorophenoxy)methyl, benzyl, 2-phenylethyl or 2-(methylthio)ethyl. Preferred alkyl groups are methyl, ethyl, n-propyl, i-propyl, n-butyl, i-butyl, t-butyl, 1-ethylpropyl, 2,4,4-trimethylpentyl, chloromethyl, trifluoromethyl, 2,2,2-trifluoroethyl, hydroxymethyl, cyanomethyl, azidomethyl, (acetylamino)methyl, (propionylamino)methyl, (benzoylamino)methyl or 2-(methylthio)ethyl. More preferred alkyl groups are methyl, ethyl, n-propyl, i-propyl, n-butyl, azidomethyl or trifluoromethyl. Most preferred alkyl groups are methyl or n-propyl.

The term "cycloalkyl", as used herein, represents a monovalent group of 3 to 8 carbon atoms, usually 3-6 carbon atoms derived from a saturated cyclic hydrocarbon, which may be substituted by any suitable group including but not limited to one or more moieties selected from groups as described above for the alkyl groups. Preferred cycloalkyl groups are cyclopropyl and cyclohexyl.

The term “alkenyl” as used herein, represents straight, branched or cyclic unsaturated hydrocarbon radicals or combinations thereof having at least one carbon-carbon double bond, containing 2-12 carbon atoms, preferably usually 2-4 carbon atoms. Alkenyl groups are being optionally substituted with any suitable group, including but not limited to one or more moieties selected from groups as described above for the alkyl groups. Usually an alkenyl group is ethenyl (vinyl) optionally substituted by 1 to 3 halogens. Preferred alkenyl group, in the present case, is 2,2-difluorovinyl.

The term “alkynyl” as used herein, represents straight, branched or cyclic hydrocarbon radicals or combinations thereof containing at least one carbon-carbon triple bond, containing 2-12 carbon atoms, preferably 2-6 carbon atoms, and being optionally substituted by any suitable group, including but not limited to one or more moieties selected from groups as described above for the alkyl groups. Preferably an alkynyl group is a halogenoalkynyl group (haloalkynyl group).

Groups qualified by prefixes such as “s”, “i”, “t” and the like (e.g. “i-propyl”, “s-butyl”) are branched derivatives.

The term “aryl” as used herein, is defined as phenyl optionally substituted by 1 to 4 substituents independently selected from halogen, cyano, alkoxy, alkylthio, $C_{1-3}$ alkyl or azido, preferably halogen or azido. Usually aryl groups, in the present case are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl, 3-azido-2,4-difluorophenyl or 3-azido-2,4,6-trifluorophenyl. Preferably, aryl groups are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl or 3-azido-2,4-difluorophenyl. Most preferred aryl groups are phenyl, 3-chlorophenyl, 3-fluorophenyl, 3,5-difluorophenyl, 2,3,4-trifluorophenyl, 2,4,5-trifluorophenyl, 2,3,5-trifluorophenyl, 3,4,5-trifluorophenyl or 3-azido-2,4-difluorophenyl.

The term “heterocycle”, as used herein, is defined as including an aromatic or non aromatic cycloalkyl moiety as defined above, having at least one O, S and/or N atom interrupting the carbocyclic ring structure. Heterocyclic ring moieties can be optionally substituted by alkyl groups or halogens and optionally, one of the carbon of the carbocyclic ring structure may be replaced by a carbonyl. Usually heterocycles are 2-pyridyl, 3-pyridyl, 4-pyridyl, 2-furyl, 3-furyl, 2-thienyl, 3-thienyl, 2-tetrahydrofuranyl, 1H-pyrrol-2-yl, 1-methyl-1H-pyrrol-2-yl, 1H-pyrazol-2-yl, 1H-pyrazol-3-yl, 4-chloro-1-methyl-1H-pyrazol-3-yl, 5-chloro-1,3-dimethyl-1H-pyrazol-4-yl, 1,2,3-thiadiazol-4-yl, 3,5-dimethyl-4-isothiazyl, 1H-imidazol-2-yl, 1-methyl-1H-imidazol-2-yl, 4-methyl-1H-imidazol-5-yl, or 2-methyl-1,3-thiazol-4-yl. Preferred heterocycles are 1H-imidazol-2-yl, 1,2,3-thiadiazol-4-yl, 1H-pyrazol-3-yl, 2-furyl, 3-furyl, 2-thienyl, 1-methyl-1H-pyrrol-2-yl, 1H-pyrrol-2-yl.

The term “halogen”, as used herein, includes an atom of chlorine, bromine, fluorine, iodine. Usually halogens are chlorine, bromine and fluorine. Preferred halogens are fluorine, bromine and chlorine.

The term “hydroxy”, as used herein, represents a group of formula —OH.

The term “alkoxy”, as used herein, represents a group of formula $—OR^a$ wherein $R^a$ is an alkyl group, as defined above. Preferred alkoxy group is methoxy.

The term “aryloxy”, as used herein, represents a group of formula $—OR^b$ wherein $R^b$ is an aryl group, as defined above. Preferred aryloxy group is phenoxy.

The term “ester”, as used herein, represents a group of formula $—COOR^c$ wherein $R^c$ is an alkyl group or aryl group, as defined above. Preferred ester group is methoxycarbonyl.

The term “amido”, as used herein, represents a group of formula $—CONH_2$.

The term “amino”, as used herein, represents a group of formula $—NH_2$.

The term “aminoderivative”, as used herein, represents an alkylamino or an arylamino group, wherein the terms “alkyl” and “aryl” are defined as above.

The term “cyano”, as used herein, represents a group of formula —CN.

The term “nitro”, as used herein, represents a group of formula $—N_2$.

The term “azido”, as used herein, represents a group of formula $—N_3$.

The term “guanidine”, as used herein, represents a group of formula $—NHC(=NH)NH_2$.

The term “alkylthio”, as used herein, represents a group of formula $—SR^d$ wherein $R^d$ is an alkyl group, as defined above. Preferred alkylthio group is methylthio.

The term “alkylsulfonyl”, as used herein, represents a group of formula $—S(=O)_2R^e$ wherein $R^e$ is an alkyl group, as defined above. Preferred alkylsulfonyl group is methylsulfonyl.

The term “alkylsulfinyl”, as used herein, represents a group of formula $—S(=O)R^f$ wherein $R^f$ is an alkyl group, as defined above. Preferred alkylsulfinyl group is methylsulfinyl.

The term “arylthio”, as used herein, represents a group of formula $—SR^g$ wherein $R^g$ is an aryl group, as defined above.

The term “arylsulfonyl”, as used herein, represents a group of the formula $—S(=O)_2R^h$ wherein $R^h$ is an aryl group, as defined above.

The term “arylsulfinyl”, as used herein, represents a group of the formula $—S(=O)R^i$ wherein $R^i$ is an aryl group, as defined above.

The term “carbamate” as used herein, represents a group of formula $—N(H)C(O)OR^j$, wherein $R^j$ is an alkyl or an aryl, as defined above. Usually carbamate groups are (propoxycarbonyl)amino or (benzyloaxycarbonyl)amino. Preferred carbamate group is (benzyloaxycarbonyl)amino.

The term “alkanoylamino” as used herein, represents a group of the formula $—NHC(=O)R^k$ wherein $R^k$ is an alkyl group, as defined above.

The term “(arylcarbonyl)amino” as used herein, represents a group of the formula $—NHC(=O)R^m$ wherein $R^m$ is an aryl group, as defined above. Preferred (arylcarbonyl)amino is benzoylamino.

Usually, $R^1$ is hydrogen; $C_{1-10}$ alkyl unsubstituted or substituted by halogen, hydroxy, cyano, methylthio, phenyl or 4-chlorophenoxy; hydroxy; $C_{3-6}$ cycloalkyl; halogen; ester; amido; nitro; cyano; amino; phenyl; alkylthio; alkylsulfonyl; alkylsulfinyl; heterocycle unsubstituted or substituted by alkyl groups; or guanidine. Preferably, $R^1$ is hydrogen; methyl; ethyl; i-propyl; n-propyl; cyclopropyl; n-butyl; i-butyl; t-butyl; 1-ethylpropyl; 2,4,4-trimethylpentyl; hydroxymethyl; chloromethyl; trifluoromethyl; 2,2,2-trifluoroethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2 thienyl;

1H-pyrazol-3-yl; 1,2,3-thiadiazol-4-yl or 1H-imidazol-2-yl. More preferably, $R^1$ is hydrogen; methyl; ethyl; i-propyl; n-propyl; n-butyl; methylthio; nitro; cyano; amino; chloro or 1H-pyrrol-2-yl. Most preferably, $R^1$ is hydrogen; methyl; methylthio; nitro; cyano; amino or chloro.

Usually, $R^2$ is hydrogen; $C_{1-4}$ alkyl unsubstituted or substituted by hydroxy, alkanoylamino or benzoylamino; halogen; ester; cyano; alkyl carbamate; [(N-methoxy-N-methyl)amino]carbonyl. Preferably, $R^2$ is hydrogen; methyl; hydroxymethyl; (acetylamino)methyl; (propionylamino)methyl; (benzoylamino)methyl; [(benzyloxy)carbonyl]amino; chloro or cyano. More preferably, $R^2$ is hydrogen; chloro or cyano.

Usually, $R^3$ is hydrogen; $C_{1-4}$ alkyl unsubstituted or substituted by hydroxy; halogen; ester or cyano. Preferably, $R^3$ is hydrogen; hydroxymethyl; chloro; cyano. More preferably, $R^3$ is hydrogen or cyano. Most preferred $R^3$ is hydrogen.

Usually, $R^4$ is hydrogen; $C_{1-4}$ alkyl unsubstituted or substituted by halogens; $C_{2-4}$ alkenyl substituted by halogens or phenyl group unsubstituted or substituted by azido or/and halogens. Preferably, $R^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl or 3-azido-2,4,6-trifluorophenyl. More preferably, $R^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl or 3-azido-2,4-difluorophenyl. Most preferably, $R^4$ is n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl or 3-azido-2,4-difluorophenyl.

Usually, $R^{4a}$ is hydrogen.

Usually, $R^5$ is hydrogen.

Usually, $R^6$ is hydrogen or $C_{1-10}$ alkyl unsubstituted or substituted by hydroxy or azido. Preferably, $R^6$ is hydrogen or azidomethyl. More preferably $R^6$ is hydrogen.

Usually $R^7$ is hydrogen.

In other preferred embodiments, $R^6$ and $R^7$ are linked to form a cyclopropyl.

In other preferred embodiments, $R^2$ and $R^3$ can form together with the imidazole ring the following 1H-benzimidazole cycle

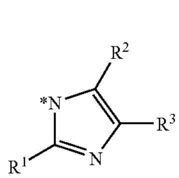

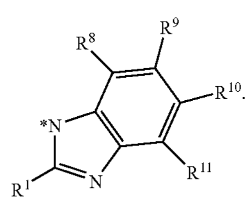

Usually, $R^8$ is hydrogen.

Usually, $R^9$ is hydrogen; halogen; $C_{1-3}$ alkyl or alkoxy. Preferably, $R^9$ is hydrogen; methyl; chloro or methoxy. More preferred $R^9$ is hydrogen.

Usually, $R^{10}$ is hydrogen; halogen; cyano; $C_{1-3}$ alkyl unsubstituted or substituted by halogens; or alkoxy. Preferably, $R^{10}$ is methyl; hydrogen; trifluoromethyl; fluoro; cyano or methoxy. More preferred $R^{10}$ is hydrogen; trifluoromethyl; fluoro or cyano.

Usually, $R^{11}$ is hydrogen.

In other preferred embodiments, $R^4$, $R^{4a}$ and $R^5$ can form together with the 2-oxo-1-pyrrolidine ring the following 1,3-dihydro-2H-indol-2-one cycle

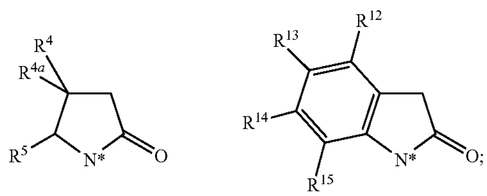

Usually, $R^{12}$ is hydrogen or halogen. Preferably $R^{12}$ is hydrogen; chloro or fluoro. More preferred $R^{12}$ is hydrogen.

Usually, $R^{13}$ is hydrogen; $C_{1-3}$ alkyl; halogen or thiazolyl unsubstituted or substituted by alkyl groups, such as methylthiazolyl. Preferably $R^{13}$ is hydrogen; chloro; bromo or methyl. Most preferred $R^{13}$ is chloro; bromo or methyl.

Usually $R^{14}$ is hydrogen.

Usually, $R^{15}$ is hydrogen.

Combinations of one or more of these preferred compound groups are especially preferred.

In a general embodiment of the invention, the compounds of formula I, or pharmaceutically acceptable salts thereof, are those wherein $R^1$ is selected from hydrogen; $C_{1-10}$ alkyl unsubstituted or substituted by halogen, hydroxy, cyano, methylthio, phenyl or 4-chlorophenoxy; $C_{3-6}$ cycloalkyl; halogen; ester; amido; nitro; cyano; amino; phenyl; alkylthio; alkylsulfonyl; alkylsulfinyl; heterocycle unsubstituted or substituted by alkyl group; or guanidine;

$R^2$ is selected from hydrogen; $C_{1-4}$ alkyl unsubstituted or substituted by hydroxy, alkanoylamino or benzoylamino; halogen; ester; cyano; alkyl carbamate or [(N-methoxy-N-methyl)amino]carbonyl.

$R^3$ is selected from hydrogen; $C_{1-4}$ alkyl unsubstituted or substituted by hydroxy; halogen; ester or cyano;

$R^4$ is selected from hydrogen; $C_{1-4}$ alkyl unsubstituted or substituted by halogens; $C_{2-4}$ alkenyl substituted by halogens or phenyl group unsubstituted or substituted by azido or/and halogens;

$R^{4a}$ is hydrogen;

$R^5$ is hydrogen;

$R^6$ is selected from hydrogen or $C_{1-10}$ alkyl unsubstituted or substituted by hydroxy or azido;

$R^7$ is hydrogen;

or $R^6$ and $R^7$ can be linked to form a cyclopropyl;

or $R^2$ and $R^3$ can form together with the imidazole ring the following 1H-benzimidazole cycle

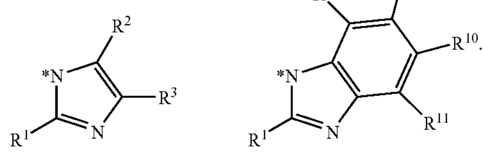

$R^8$ is hydrogen;

$R^9$ is selected from hydrogen; halogen; $C_{1-3}$ alkyl; alkoxy;

$R^{10}$ is selected from hydrogen; halogen; cyano or $C_{1-3}$ alkyl unsubstituted or substituted by halogens; or alkoxy;

$R^{11}$ is hydrogen;

or $R^4$, $R^{4a}$ and $R^5$ can form together with the 2-oxo-1-pyrrolidine ring the following 1,3-dihydro-2H-indol-2-one cycle

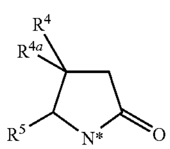
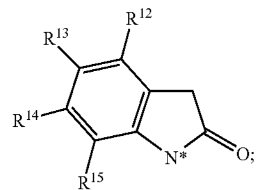

$R^{12}$ is selected from hydrogen or halogen;

$R^{13}$ is selected from hydrogen; $C_{1-3}$ alkyl; halogen; thiazolyl unsubstituted or substituted by alkyl groups, such as methylthiazolyl;

$R^{14}$ is hydrogen;

$R^{15}$ is hydrogen;

with the proviso that $R^4$ is different from hydrogen when

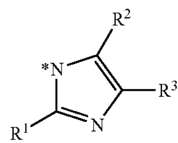

represents a group of formula

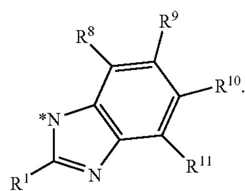

In a preferred embodiment of the invention, the compounds of formula I, or pharmaceutically acceptable salt thereof, are those wherein $R^1$ is selected from hydrogen; methyl; ethyl; i-propyl; n-propyl; cyclopropyl; n-butyl; i-butyl; t-butyl; 1-ethylpropyl; 2,4,4-trimethylpentyl; trifluoromethyl; 2,2,2-trifluoroethyl; hydroxymethyl; chloromethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl; or 1H-imidazol-2-yl;

$R^2$ is selected from hydrogen; methyl; hydroxymethyl; (acetylamino)methyl; (propionylamino)methyl; (benzoylamino)methyl; (benzyloxycarbonyl)amino; chloro; or cyano;

$R^3$ is selected from hydrogen; hydroxymethyl; chloro; cyano;

or $R^2$ and $R^3$ can form together with the imidazole ring the following 1H-benzimidazole cycle

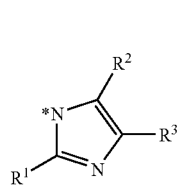
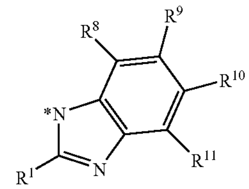

$R^8$ is hydrogen;

$R^9$ is selected from hydrogen; methyl; choro; methoxy;

$R^{10}$ is selected from methyl; hydrogen; trifluoromethyl; fluoro; cyano; or methoxy;

$R^{11}$ is hydrogen;

$R^4$ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl; or 3-azido-2,4,6-trifluorophenyl.

$R^{4a}$ is hydrogen;

$R^5$ is hydrogen;

or $R^4$, $R^{4a}$ and $R^5$ can form together with the 2-oxo-1-pyrrolidine ring the following 1,3-dihydro-2H-indol-2-one cycle

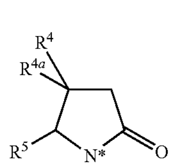
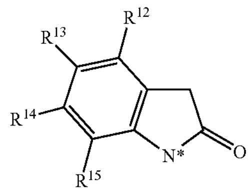

$R^{12}$ is selected from hydrogen; chloro; fluoro;

$R^{13}$ is selected from hydrogen; chloro; bromo; methyl;

$R^{14}$ is hydrogen;

$R^{15}$ hydrogen;

$R^6$ is selected from hydrogen; azidomethyl;

$R^7$ is hydrogen;

or $R^6$ and $R^7$ are linked to form a cyclopropyl;

with the proviso that $R^4$ is different from hydrogen when

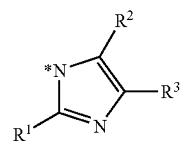

represents a group of formula

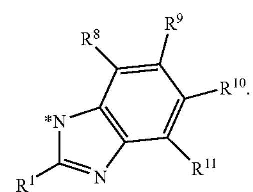

In a more preferred embodiment of the invention, the compounds of formula I, or pharmaceutically acceptable salt thereof, are those wherein $R^1$ is selected from hydrogen; methyl; ethyl; i-propyl; n-propyl; n-butyl; methylthio; nitro; cyano; amino; chloro; or 1H-pyrrol-2-yl;

$R^2$ is selected from hydrogen; chloro; cyano;

$R^3$ is selected from hydrogen; cyano;

or $R^2$ and $R^3$ can form together with the imidazole ring the following 1H-benzimidazole cycle

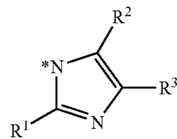

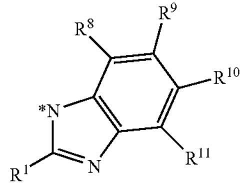

$R^8$ is hydrogen;

$R^9$ is hydrogen;

$R^{10}$ is selected from hydrogen; trifluoromethyl; fluoro; cyano;

$R^{11}$ is hydrogen;

$R^4$ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; or 3-azido-2,4-difluorophenyl;

$R^{4a}$ is hydrogen;

$R^5$ is hydrogen;

or $R^4$, $R^{4a}$ and $R^5$ can form together with the 2-oxo-1-pyrrolidine ring the following 1,3-dihydro-2H-indol-2-one cycle

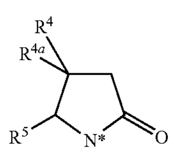

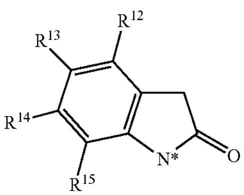

wherein $R^{12}$ is hydrogen;

$R^{13}$ is selected from methyl; chloro; bromo;

$R^{14}$ is hydrogen;

$R^{15}$ hydrogen;

$R^6$ is hydrogen;

$R^7$ is hydrogen;

with the proviso that $R^4$ is different from hydrogen when

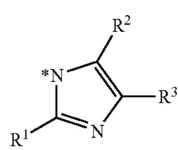

represents a group of formula

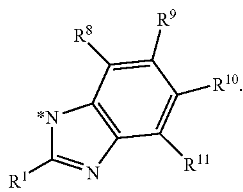

In a most preferred embodiment of the invention, the compounds of formula I, or pharmaceutically acceptable salt thereof, are those wherein $R^1$ is selected from hydrogen; methyl; methylthio; nitro; cyano; amino; chloro;

$R^2$ is selected from hydrogen; chloro; cyano;

$R^3$ is hydrogen;

$R^4$ is selected from n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl; 3-azido-2,4-difluorophenyl;

$R^{4a}$ is hydrogen;

$R^5$ is hydrogen;

or $R^4$, $R^{4a}$ and $R^5$ can form together with the 2-oxo-1-pyrrolidine ring the following 1,3-dihydro-2H-indol-2-one cycle

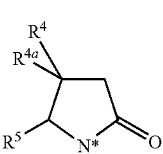

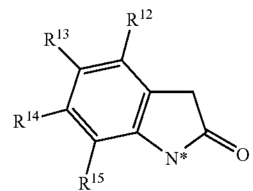

$R^{12}$ is hydrogen;

$R^{13}$ is selected from chloro; bromo; methyl;

$R^{14}$ is hydrogen;

$R^{15}$ hydrogen;

$R^6$ is hydrogen;

$R^7$ is hydrogen.

Preferred compounds are: 1-(1H-imidazol-1-ylmethyl)pyrrolidin-2-one; 1-(1H-imidazol-1-ylmethyl)-4-phenylpyrrolidin-2-one; 4-(3-azido-2,4,6-trifluorophenyl)-1-(1H-imidazol-1-ylmethyl)pyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 1-[(2-phenyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-{[2-(methylsulfinyl)-1H-imidazol-1-yl]methyl}-4-propylpyrrolidin-2-one; 1-[(2-tert-butyl-1H-imidazol-1-yl)methyl]-4-propylpyrrolidin-2-one; 1-[1-(1H-imidazol-1-yl)cyclopropyl]pyrrolidin-2-one; 1-[(2-methyl-1H-imidazol-1-yl)methyl]-4-phenylpyrrolidin-2-one; 1-{[2-(methylsulfonyl)-1H-imidazol-1-yl]methyl}-4-propylpyrrolidin-2-one; 1-[(2-oxo-4-propylpyrrolidin-1-yl)methyl]-1H-imidazole-2-carboxamide; 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one;

4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-{[2-(hydroxymethyl)-1H-imidazol-1-yl]methyl}-4-propylpyrrolidin-2-one; methyl 1-[(2-oxo-4-propylpyrrolidin-1-yl)methyl]-1H-imidazole-2-carboxylate; 1-[(2-nitro-1H-imidazol-1-yl)methyl]-4-(3,4,5-trifluorophenyl)pyrrolidin-2-one; 1-{[2-oxo-4-(3,4,5-trifluorophenyl) pyrrolidin-1-yl]methyl}-1H-imidazole-2-carbonitrile; 1-[(2-amino-1H-imidazol-1-yl)methyl]-4-propylpyrrolidin-2-one; 1-[(2,4-dichloro-1H-imidazol-1-yl)methyl]-4-(3,4,5-trifluorophenyl)pyrrolidin-2-one; 1-[(5-chloro-1H-imidazol-1-yl) methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; 1-{[2-oxo-4-(2,3,5-trifluorophenyl) pyrrolidin-1-yl]methyl}-1H-imidazole-5-carbonitrile; (−)-1-{[2-oxo-4-(2,3,4-trifluorophenyl)pyrrolidin-1-yl]methyl}-1H-imidazole-5-carbonitrile; (+)-1-{[2-oxo-4-(2,3,4-trifluorophenyl)pyrrolidin-1-yl]methyl}-1H-imidazole-5-carbonitrile; (−)-1-{[2-oxo-4-(2,3,4-trifluorophenyl) pyrrolidin-1-yl]methyl}-1H-imidazole-4-carbonitrile; (+)-1-{[2-oxo-4-(2,3,4-trifluorophenyl)-1-pyrrolidinyl]methyl}-1H-imidazole-4-carbonitrile; (−)-1-{[2-oxo-4-(3,4,5-trifluorophenyl)pyrrolidin-1-yl]methyl}-1H-imidazole-4-carbonitrile; (+)-1-{[2-oxo-4-(3,4,5-trifluorophenyl) pyrrolidin-1-yl]methyl}-1H-imidazole-4-carbonitrile; (+)-1-{[2-oxo-4-(2,4,5-trifluorophenyl)pyrrolidin-1-yl]methyl}-1H-imidazole-4-carbonitrile; (−)-1-{[2-oxo-4-(2,4,5-trifluorophenyl)pyrrolidin-1-yl]methyl}-1H-imidazole-4-carbonitrile; (−)-1-{[2-oxo-4-(2,3,5-trifluorophenyl) pyrrolidin-1-yl]methyl}-1H-imidazole-4-carbonitrile; (−)-1-{[2-oxo-4-(3,4,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-[(5-methyl-2-phenyl-1H-imidazol-1-yl)methyl]-4-propylpyrrolidin-2-one; 1-[(5-methyl-1H-imidazol-1-yl)methyl]-4-propylpyrrolidin-2-one; 1-[(5-phenyl-1H-imidazol-1-yl) methyl]-4-propylpyrrolidin-2-one; 1-[(2-ethyl-5-methyl-1H-imidazol-1-yl)methyl]-4-propylpyrrolidin-2-one; 1-[(2,5-dimethyl-1H-imidazol-1-yl)methyl]-4-propylpyrrolidin-2-one; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(4-chloro-1H-imidazol-1-yl)methyl]-4-(3,4,5-trifluorophenyl) pyrrolidin-2-one; 1-[(2-bromo-4,5-dichloro-1H-imidazol-1-yl)methyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-{[5-(hydroxymethyl)-1H-imidazol-1-yl]methyl}-4-propylpyrrolidin-2-one; 1-{[4-(hydroxymethyl)-1H-imidazol-1-yl]methyl}-4-propylpyrrolidin-2-one; benzyl 1-[(2-oxo-4-propylpyrrolidin-1-yl)methyl]-1H-imidazol-5-ylcarbamate; N-[(1-{[2-oxo-4-(3,4,5-trifluorophenyl)pyrrolidin-1-yl]methyl}-1H-imidazol-5-yl)methyl]acetamide; N-[(1-{[2-oxo-4-(3,4,5-trifluorophenyl)pyrrolidin-1-yl]methyl}-1H-imidazol-5-yl)methyl]benzamide; N-[(1-{[2-oxo-4-(3,4,5-trifluorophenyl)pyrrolidin-1-yl]methyl}-1H-imidazol-5-yl) methyl]propanamide; 1-(1H-benzimidazol-1-ylmethyl)-4-propylpyrrolidin-2-one; 1-[(2-methyl-1H-benzimidazol-1-yl)methyl]-4-propylpyrrolidin-2-one; 4-propyl-1-[(2-propyl-1H-benzimidazol-1-yl)methyl]pyrrolidin-2-one; 1-[(2-isopropyl-1H-benzimidazol-1-yl)methyl]-4-propylpyrrolidin-2-one; 4-propyl-1-{[2-(trifluoromethyl)-1H-benzimidazol-1-yl]methyl}pyrrolidin-2-one; 1-{[2-(methylthio)-1H-benzimidazol-1-yl]methyl}-4-propylpyrrolidin-2-one; 1-[(2-amino-1H-benzimidazol-1-yl)methyl]-4-propylpyrrolidin-2-one; 1-{[2-(chloromethyl)-1H-benzimidazol-1-yl]methyl}-4-propylpyrrolidin-2-one; {1-[(2-oxo-4-propylpyrrolidin-1-yl)methyl]-1H-benzimidazol-2-yl}acetonitrile; 1-[(5-methoxy-1H-benzimidazol-1-yl) methyl]-4-propylpyrrolidin-2-one; 1-[(5-methyl-1H-benzimidazol-1-yl)methyl]-4-propylpyrrolidin-2-one; 1-[(5,6-dimethyl-1H-benzimidazol-1-yl)methyl]-4-propylpyrrolidin-2-one; 1-{[2-isopropyl-5-(trifluoromethyl)-1H-benzimidazol-1-yl]methyl}-4-propylpyrrolidin-2-one; 1-[(6-chloro-1H-benzimidazol-1-yl)methyl]-4-propylpyrrolidin-2-one; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl] methyl}pyrrolidin-2-one; 1-[(5-fluoro-2-propyl-1H-benzimidazol-1-yl)methyl]-4-propylpyrrolidin-2-one; 1-{[6-methyl-2-(1H-pyrrol-2-yl)-1H-benzimidazol-1-yl]methyl}-4-propylpyrrolidin-2-one; 1-[(6-methoxy-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-{[2-[2-(methylthio)ethyl]-5-(trifluoromethyl)-1H-benzimidazol-1-yl]methyl}-4-propylpyrrolidin-2-one; 1-[(5-fluoro-2-isobutyl-1H-benzimidazol-1-yl)methyl]-4-propylpyrrolidin-2-one; 1-{[5-fluoro-2-(2,4,4-trimethylpentyl)-1H-benzimidazol-1-yl] methyl}-4-propylpyrrolidin-2-one; 2-cyclopropyl-1-[(2-oxo-4-propylpyrrolidin-1-yl)methyl]-1H-benzimidazole-5-carbonitrile; 1-[(2-oxo-4-propylpyrrolidin-1-yl)methyl]-2-(1H-pyrazol-3-yl)-1H-benzimidazole-5-carbonitrile; 1-[(2-cyclopropyl-5-fluoro-1H-benzimidazol-1-yl)methyl]-4-propylpyrrolidin-2-one; 1-[(5-fluoro-2-isopropyl-1H-benzimidazol-1-yl)methyl]-4-propylpyrrolidin-2-one; 1-{[2-(3-furyl)-6-methoxy-1H-benzimidazol-1-yl]methyl}-4-propylpyrrolidin-2-one; 1-[(2-cyclopropyl-6-methoxy-1H-benzimidazol-1-yl)methyl]-4-propylpyrrolidin-2-one; 1-[(2-isopropyl-6-methoxy-1H-benzimidazol-1-yl)methyl]-4-propylpyrrolidin-2-one; 1-[(2-oxo-4-propylpyrrolidin-1-yl) methyl]-2-(1,2,3-thiadiazol-4-yl)-1H-benzimidazole-5-carbonitrile; 1-{[2-(1H-imidazol-2-yl)-5-(trifluoromethyl)-1H-benzimidazol-1-yl]methyl}-4-propylpyrrolidin-2-one; 1-{[5-fluoro-2-(2,2,2-trifluoroethyl)-1H-benzimidazol-1-yl] methyl}-4-propylpyrrolidin-2-one; 1-{[2-(1-ethylpropyl)-6-methoxy-1H-benzimidazol-1-yl]methyl}-4-propylpyrrolidin-2-one; 1-{[6-methoxy-2-(1-methyl-1H-pyrrol-2-yl)-1H-benzimidazol-1-yl]methyl}-4-propylpyrrolidin-2-one; 1-{[2-(2-furyl)-5-(trifluoromethyl)-1H-benzimidazol-1-yl] methyl}-4-propylpyrrolidin-2-one; 4-propyl-1-{[2-thien-2-yl-5-(trifluoromethyl)-1H-benzimidazol-1-yl] methyl}pyrrolidin-2-one; 1-{[2-(3-furyl)-5-(trifluoromethyl)-1H-benzimidazol-1-yl]methyl}-4-propylpyrrolidin-2-one; 1-{[2-cyclopropyl-5-(trifluoromethyl)-1H-benzimidazol-1-yl]methyl}-4-propylpyrrolidin-2-one; 4-propyl-1-{[2-(1H-pyrrol-2-yl)-5-(trifluoromethyl)-1H-benzimidazol-1-yl]methyl}pyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 4-fluoro-1-(1H-imidazol-1- ylmethyl)-1,3-dihydro-2H-indol-2-one; 4-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(2-oxo-2,3-dihydro-1H-indol-1-yl)methyl]-1H-imidazole-5-carbonitrile; and 1-[(5-chloro-2-oxo-2,3-dihydro-1H-indol-1-yl)methyl]-1H-imidazole-5-carbonitrile.

More preferred compounds are: 1-(1H-imidazol-1-ylmethyl)pyrrolidin-2-one, 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one; 4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; (+); 1-{[2-oxo-4-(3,4,5-trifluorophenyl)pyrrolidin-1-yl]methyl}-1H-imidazole-4-carbonitrile; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-[(5-fluoro-2-isopropyl-1H-benzimidazol-1-yl)methyl]-4-propylpyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

Most preferred compounds are: 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; (+)-1-(1H-imidazol-1-ylmethyl)-4-phenylpyrrolidin-2-one; (−)-1-(1H-imidazol-1-ylmethyl)-4-phenylpyrrolidin-2-one; 1-[(2-chloro-1H-imidazol-1-yl)methyl]-4-(3,4,5-trifluorophenyl)pyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

Best compounds are: (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(3-azido-2,4-difluorophenyl)-1-(1H-imidazol-1-ylmethyl)pyrrolidin-2-one.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicity indicated in the above formula are intended to be included within the scope of the present invention.

In another preferred embodiment, the present invention concerns also compounds of formula IA and their tautomeric form IB

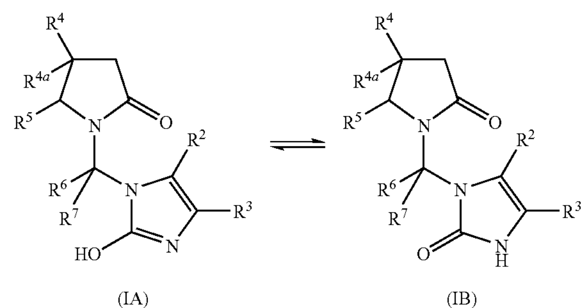

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are intended to be included within the scope of the present invention.

The invention also includes within its scope pro-drug forms of the compounds of formula I and its various subscopes and sub-groups.

The compounds of formula I according to the invention can be prepared analogously to conventional methods as understood by the person skilled in the art of synthetic organic chemistry.

A. According to one embodiment, some compounds having the general formula I wherein $R^7$ is H may be prepared by chlorination of a compound of formula II and reaction of the corresponding derivative of formula III with an imidazole of formula IV according to the equation:

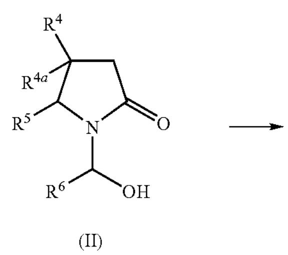

-continued

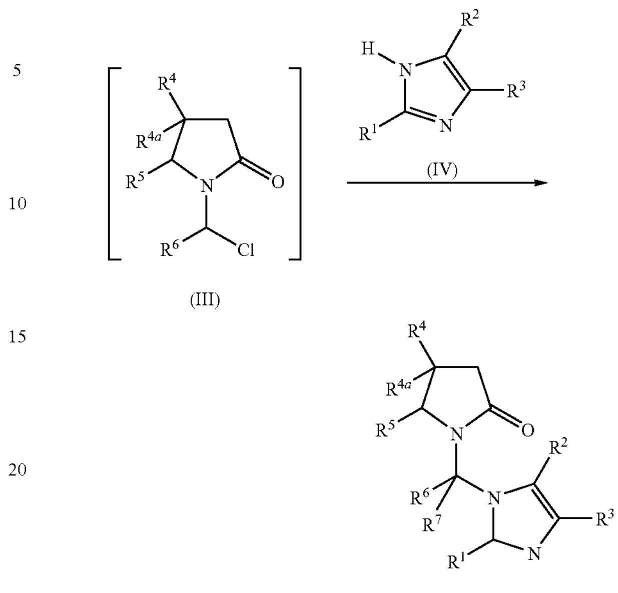

This reaction may be carried out using thionyl chloride (or any other chlorination agent such as HCl, $POCl_3$, $PCl_5$ . . . ) neat or in toluene at a temperature ranging from 20° C. to 80° C.

Compounds of formula II may be prepared by hydroxyalkylation of a compound of formula V with an aldehyde of formula $R^6CHO$ according to the equation:

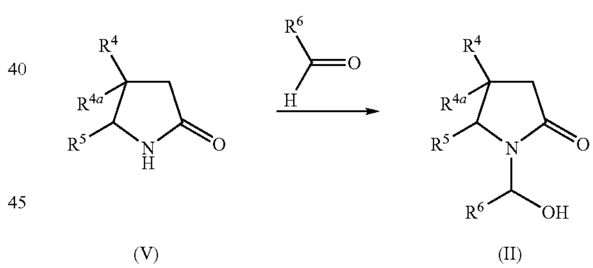

This reaction may be carried out by heating the pyrrolidone derivative with an aldehyde (or its synthetic equivalent such as paraformaldehyde in the case of formaldehyde) in the presence of an acid or a base such as $CF_3CO_2H$ or NaOH.

The pyrrolidones of formula V are synthesized using either conventional methods described in the literature (see for example: Gouliaev A. H., Monster J. B., Vedso M., Senning A., Org. Prep. Proceed. Int. (1995), 27, 273-303) or methods described in international patent application WO 01/62726.

B. According to another embodiment, some compounds having the general formula I wherein $R^7$ is H may be prepared by transformation of compound of formula II into the corresponding carbamate of formula VI and reaction of this carbamate with a compound of formula IV according to the equation:

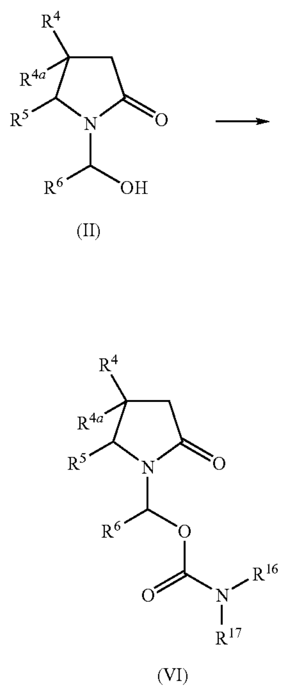

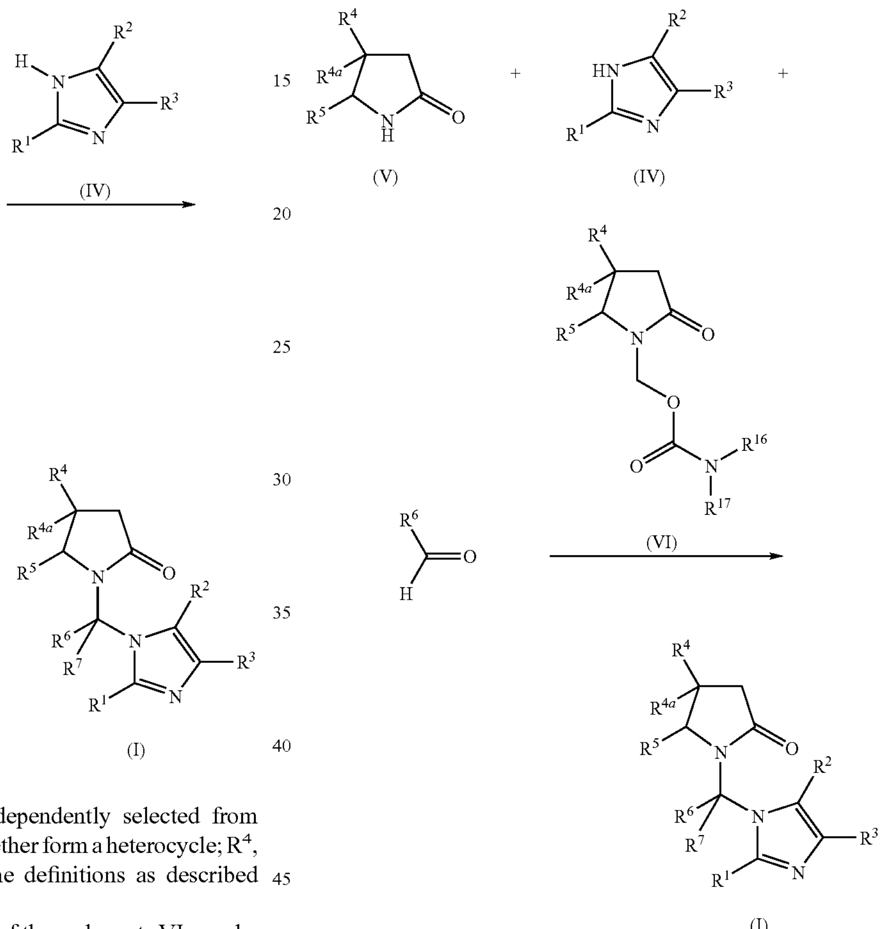

wherein $R^{16}$ and $R^{17}$ are independently selected from hydrogen; $C_{1-20}$ alkyl; aryl or together form a heterocycle; $R^4$, $R^{4a}$, $R^5$ and $R^6$ having the same definitions as described above.

This reaction for the synthesis of the carbamate VI may be carried out under any conventional method known to the person skilled in the art or as described in U.S. Pat. No. 3,903,110.

Reaction of carbamate VI with an imidazole derivative of formula IV can be carried out in three different ways:

- the stoechiometric version consists in mixing the carbamate VI with an excess of the nucleophile IV (2.2 eq is usually used to assure the complete consumption of the starting carbamate VI) in an inert solvent such as acetonitrile and in heating the mixture either at reflux temperature in a conventional apparatus, or under microwave irradiation (100 W irradiation is usually enough to insure the complete consumption of the starting carbamate VI);
- the catalytic version consists in heating a mixture of compound II and a slight excess of nucleophile IV (1.2 eq usually required) in presence of a catalytic amount of carbamate VI (note that the pyrrolidone moiety of II and VI may be different) either in a conventional apparatus (reflux of the used solvent is required) or under microwave irradiation (100 W irradiation is usually enough to insure the complete consumption of the starting carbamate VI).
- an alternative to the catalytic method is to generate the compound II in situ and to prepare compound I in a one step reaction according to the equation:

This reaction can be carried out using a slight excess of nucleophile IV (1.2 eq usually required), an excess of aldehyde $R^6CHO$ (4 eq usually required) and carbamate VI as a catalyst (10 mol % are usually used but the amount of catalyst can be easily reduced) in an inert solvent such as acetonitrile under microwave irradiation (100 W irradiation is usually enough to insure the complete consumption of the starting pyrrolidone V). Note that conventional heating of the reaction mixture versus microwave irradiation can also be used. N,N-disubstituted carbamoyl chloride can also be used as a catalyst instead of carbamate VI.

C. According to another embodiment, some compounds having the general formula I wherein $R^6$ and $R^7$ are linked together to form a $C_{3-6}$ cycloalkyl and $R^5$ is hydrogen may be prepared by cyclisation of a compound of formula VII according to the equation:

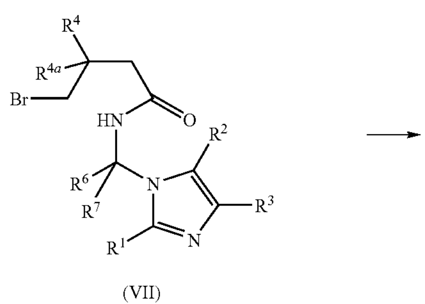

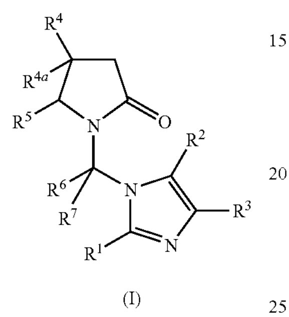

This reaction may be carried out using potassium carbonate as a base in an inert solvent (such as DMF) at temperature ranging from 20° C. to 100° C.

Compound of formula VII may be prepared by chloration of a compound of formula VIII and reaction of the corresponding derivative of formula IX with an imidazole of formula IV according to the equation:

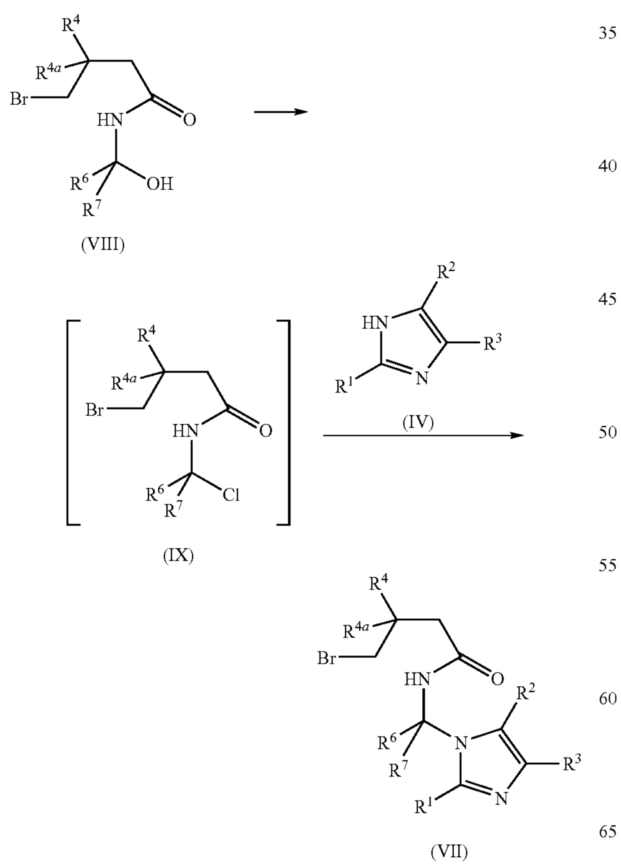

This reaction may be carried out as described in A.

Compound of formula VIII may be prepared by any conventional method known to the person skilled in the art.

D. According to another embodiment, some compounds having the general formula I wherein $R^6$ is amido or $CH_2OH$ may be prepared by transformation of a compound of formula (IX)

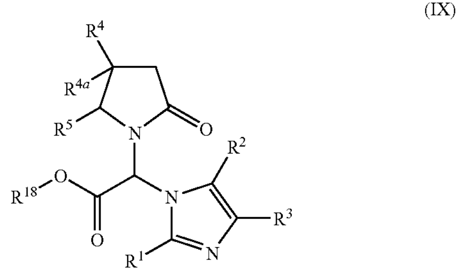

wherein $R^{18}$ is a $C_{1-4}$ alkyl, preferably methyl or ethyl.

These transformations may be performed according to any method known to the person skilled in the art.

E. According to another embodiment, some compounds having the general formula I wherein $R^7$ is H and $R^4$, $R^{4a}$ and $R^5$ form together with the 2-oxo-1-pyrrolidine ring the following 1,3-dihydro-2H-indol-2-one cycle

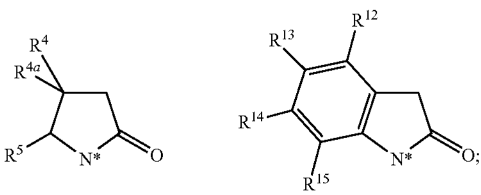

may be prepared by reaction of a compound of formula (XI) with an aldehyde of formula $R^1CHO$ according to the equation:

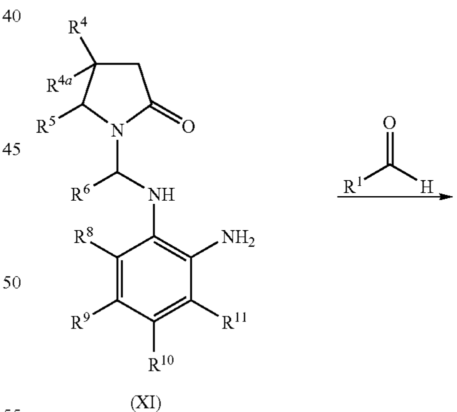

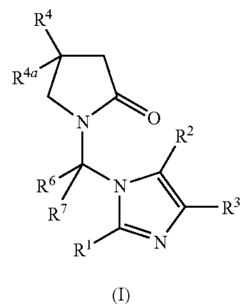

This reaction may be performed according to any method known to the person skilled in the art.

Compounds of formula XI may be prepared by reduction of a compound of formula XII.

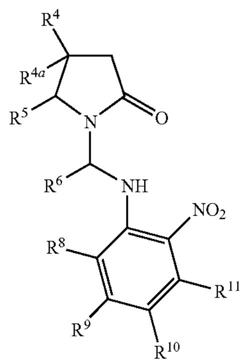

This reaction may be performed according to any method known to the person skilled in the art.

Compounds of formula XII may be prepared by reaction of an amino derivative of formula XIII with a compound of formula XIV according to the equation

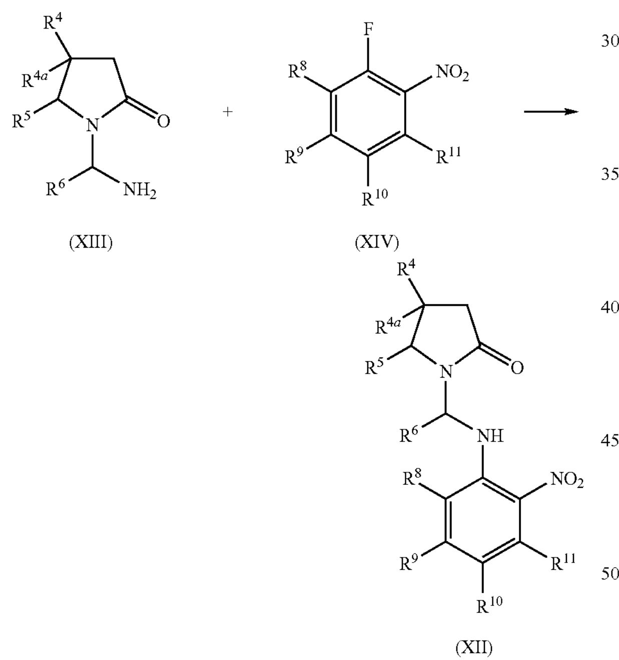

This Reaction May be Performed According to any Method Known to the Person skilled in the art.

Compounds of formula XIII may be obtained from the corresponding compound of formula III according to any method known to the person skilled in the art.

F. According to another embodiment, some compounds having the general formula I may be prepared by functional group transformation.

(a) compound of formula I wherein $R^4$ is —CH═$CF_2$ may be prepared from the corresponding compound of formula I wherein $R^4$ is —$CH_2$—$CBrF_2$ by treatment with a base;

(b) methylthio-imidazole derivatives may be oxidized using $NaIO_4$ in MeOH for the synthesis of corresponding methylsulfinyl-imidazol derivative of formula I;

(c) 1H-imidazole-2-carboxylic acid alkyl ester derivatives of formula I may be transformed into the corresponding amides or into the corresponding alcohol;

(d) nitro-imidazoles derivatives of formula I can be reduced by hydrogen in the presence of Pd/C into the corresponding amino-imidazoles derivatives according to any method known to the person skilled in the art.

(e) compound of formula I wherein $R^6$ is —$CH_2N_3$ may be prepared from the corresponding compound of formula I wherein $R^6$ is —$CH_2OH$, using a mesylate intermediate of formula (XV).

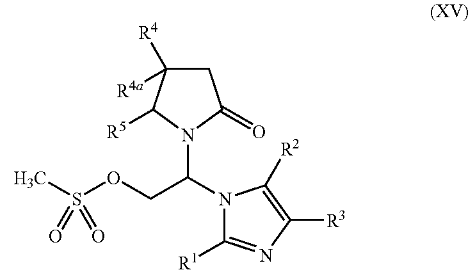

(f) compounds of formula I wherein $R^2$ and/or $R^3$ is —NHCOR$^{19}$, $R^{19}$ being an alkyl or an aryl group, may be prepared by Curtius rearrangement of the corresponding acid wherein at least one of the substituent $R^2$ or $R^3$ is —COOH, under any condition known to the person skilled in the art (for example by action of diphenylphosphorazidate and triethylamine and quenching in situ by an alcohol ($R^{19}OH$) as described in: Kim D., Weinreb S. M., J. Org. Chem. (1978), 43, 125).

(g) compounds of formula I wherein $R^2$ and/or $R^3$ is —$CH_2NHCOR^{20}$, $R^{20}$ being an alkyl or an aryl group, may be prepared by selective reduction of the corresponding amide ($R^2$ and/or $R^3$ is —$CONH_2$) or nitrile ($R^2$ and/or $R^3$ is —CN) of formula I into the aminomethyl derivative of formula I ($R^2$ and/or $R^3$ is —$CH_2NH_2$), and reaction with an acid chloride under any condition known to the person skilled in the art.

(h) compounds of formula I wherein $R^2$ and/or $R^3$ is amido are prepared by activation of the corresponding acid wherein $R^2$ and/or $R^3$ is —COOH and reaction with a primary or secondary amine under any condition known to the person skilled in the art.

(i) compounds of formula I wherein $R^2$ and/or $R^3$ is —$CH_2OH$ may be prepared from the corresponding compound wherein at least one of the substituents $R^2$ or $R^3$ is —$CH_2OSiMe_2tBu$, according to any condition known to the person skilled in the art, for example by reaction with n-$Bu_4NF$ in THF at room temperature. Such transformations may be performed according to any method known to the person skilled in the art any person.

G. According to another embodiment, some compounds having the general formula I wherein $R^2$ and $R^3$ form together with the imidazole ring the following 1H-benzimidazole cycle

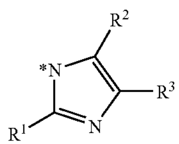

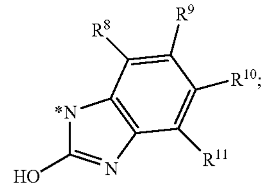

may be prepared by reaction of a compound of formula (XI) with carbonyldiimidazole. This reaction may be performed according to any method known to the person skilled in the art.

In another embodiment, the present invention concerns the following synthesis intermediates of formula II: 4-(2-bromo-2,2-difluoro-ethyl)-1-hydroxymethyl-pyrrolidin-2-one; 1-(hydroxymethyl)-4-(3,4,5-trifluorophenyl)pyrrolidin-2-one; 1-(hydroxymethyl)-4-propyl-pyrrolidin-2-one; 4-(3-chloro-phenyl)-1-hydroxymethyl-pyrrolidin-2-one; 4-(3-fluoro-phenyl)-1-hydroxymethyl-pyrrolidin-2-one; 4-(4-chloro-phenyl)-1-hydroxymethyl-pyrrolidin-2-one; 4-(4-fluoro-phenyl)-1-hydroxymethyl-pyrrolidin-2-one; 4-(3,5-difluoro-phenyl)-1-hydroxymethyl-pyrrolidin-2-one; 1-hydroxymethyl-4-(2,3,5-trifluoro-phenyl)-pyrrolidin-2-one; 1-hydroxymethyl-4-(2,3,4-trifluoro-phenyl)-pyrrolidin-2-one; 4-(3-chloro-4-fluoro-phenyl)-1-hydroxymethyl-pyrrolidin-2-one; 4-(3,4-difluoro-phenyl)-1-hydroxymethyl-pyrrolidin-2-one; 1-hydroxymethyl-4-(2,4,5-trifluoro-phenyl)-pyrrolidin-2-one; 4-(3-azido-2,4,6-trifluoro-phenyl)-1-hydroxymethyl-pyrrolidin-2-one; 4-(3-azido-2,4-difluoro-phenyl)-1-hydroxymethyl-pyrrolidin-2-one; 5-chloro-1-hydroxymethyl-1,3-dihydro-indol-2-one; 1-(hydroxymethyl)-1,3-dihydro-2H-indol-2-one; 4-chloro-1-hydroxymethyl-1,3-dihydro-indol-2-one; 4-fluoro-1-hydroxymethyl-1,3-dihydro-indol-2-one; 5-bromo-1-hydroxymethyl-1,3-dihydro-indol-2-one; 1-hydroxymethyl-5-methyl-1,3-dihydro-indol-2-one and 1-hydroxymethyl-5-(2-methyl-thiazol-4-yl)-1,3-dihydro-indol-2-one.

In another embodiment, the present invention concerns also synthesis intermediates of formula VII (VII)

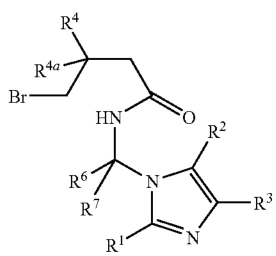

wherein $R^6$ and $R^7$ are linked together to form a $C_{3-6}$ cycloalkyl; $R^1$, $R^2$, $R^3$, $R^4$ and $R^{4a}$ have the same definitions as described above;

or $R^2$ and $R^3$ can form together with the imidazole ring the following 1H-benzimidazole cycle

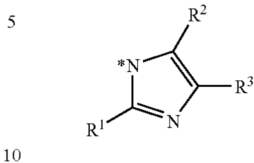

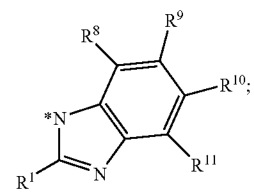

wherein $R^8$, $R^9$, $R^{10}$ and $R^{11}$ have the same definitions as described above.

In another embodiment, the present invention concerns the following synthesis intermediate of formula VII: 4-bromo-N-(1-imidazol-1-yl-cyclopropyl)-butyramide.

In another embodiment, the present invention concerns also synthesis intermediates of formula X (X)

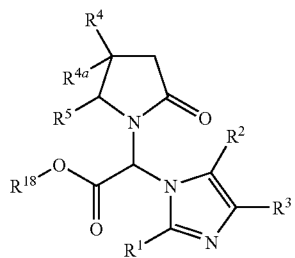

wherein $R^{18}$ is a $C_{1-4}$ alkyl;

$R^1$, $R^2$ and $R^3$ have the same definitions as described above;

or $R^2$ and $R^3$ can form together with the imidazole ring the following 1H-benzimidazole cycle

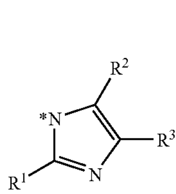

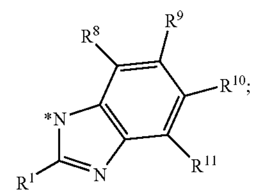

wherein $R^8$, $R^9$, $R^{10}$ and $R^{11}$ have the same definitions as described above;

and $R^4$, $R^{4a}$ and $R^5$ have the same definitions as described above;

or $R^4$, $R^{4a}$ and $R^5$ can form together with the 2-oxo-1-pyrrolidine ring the following 1,3-dihydro-2H-indol-2-one cycle

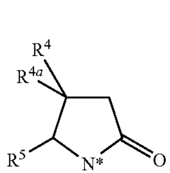

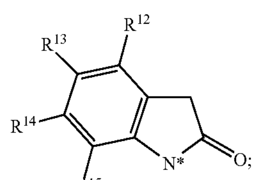

wherein $R^{12}$, $R^{13}$, $R^{14}$ and $R^{15}$ have the same definitions as defined above.

In another embodiment, the present invention concerns the following synthesis intermediate of formula X: imidazol-1-yl-(2-oxo-4-propyl-pyrrolidin-1-yl)-acetic acid ethyl ester.

In another embodiment, the present invention concerns also synthesis intermediates of formula XI (XI)

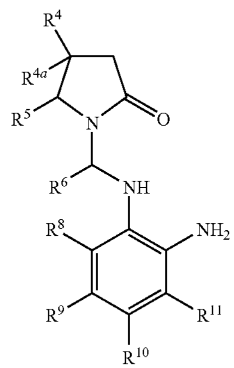

wherein $R^4$, $R^{4a}$, $R^5$, $R^6$, $R^8$, $R^9$, $R^{10}$ and $R^{11}$ have the same definitions as described above; or $R^4$, $R^{4a}$ and $R^5$ can form together with the 2-oxo-1-pyrrolidine ring the following 1,3-dihydro-2H-indol-2-one cycle

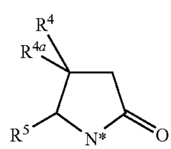

represents a group of formula

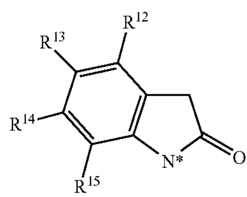

wherein $R^{12}$, $R^{13}$, $R^{14}$ and $R^{15}$ have the same definitions as defined above.

In another embodiment, the present invention concerns the following synthesis intermediate of formula XI: (2-aminophenyl){(2-oxo-4-propyl-pyrrolidin-1-yl)methyl}amine.

In another embodiment, the present invention concerns also synthesis intermediates of formula XII (XII)

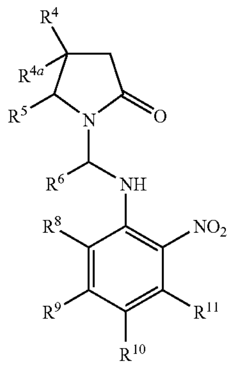

wherein $R^4$, $R^{4a}$, $R^5$, $R^6$, $R^8$, $R^9$, $R^{10}$ and $R^{11}$ have the same definitions as described above; or $R^4$, $R^{4a}$ and $R^5$ can form together with the 2-oxo-1-pyrrolidine ring the following 1,3-dihydro-2H-indol-2-one cycle

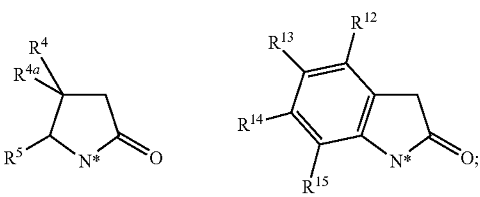

wherein $R^{12}$, $R^{13}$, $R^{14}$ and $R^{15}$ have the same definitions as defined above.

In another embodiment, the present invention concerns the following synthesis intermediate of formula XII: (2-nitrophenyl){(2-oxo-4-propyl-pyrrolidin-1-yl)methyl}amine.

In another embodiment, the present invention concern the following synthesis intermediates: 1-(4-methoxy-benzyl)-5-oxo-pyrrolidine-3-carbaldehyde; 4-(2,2-difluoro-vinyl)-1-(4-methoxy-benzyl)-pyrrolidin-2-one; 4-(2,2-difluoro-vinyl)-pyrrolidin-2-one; 4-(2-bromo-2,2-difluoro-ethyl)-pyrrolidin-2-one; (4-bromo-2,6-difluoro-phenyl)-pyrrolidin-1-yl-diazene; 6-bromo-2,4-difluoro-3-(pyrrolidin-1-ylazo)-benzaldehyde; 3-[6-bromo-2,4-difluoro-3-(pyrrolidin-1-ylazo)-phenyl]-acrylic acid ethyl ester; 3-[6-bromo-2,4-difluoro-3-(pyrrolidin-1-ylazo)-phenyl]-4-nitro-butyric acid ethyl ester; 4-[2,4-difluoro-3-(pyrrolidin-1-ylazo)-phenyl]-pyrrolidin-2-one; 4-(3-azido-2,4-difluoro-phenyl)-pyrrolidin-2-one; 4-bromo-N-(1-hydroxy-cyclopropyl)-butyramide; hydroxy-(2-oxo-4-propyl-pyrrolidin-1-yl)-acetic acid ethyl ester and 1-aminomethyl-4-propyl-pyrrolidin-2-one.

It has now been found that compounds of formula I and their pharmaceutically acceptable salts are useful in a variety of pharmaceutical disorders.

For example, the compounds according to the invention are useful for the treatment of epilepsy, epileptogenesis, seizure disorders and convulsions.

These compounds may also be used for the treatment of Parkinson's disease. These compounds may also be used for the treatment of dyskinesia induced by dopamine replacement therapy, tardive dyskinesia induced by administration of neuroleptic drugs or Huntington Chorea.

The present invention also concerns use of a compound having the formula I for the manufacture of a medicament for the treatment and prevention of epilepsy, epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

In addition, the compounds according to the invention may also be used for treating other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention also concerns a compound having the formula I or a pharmaceutically acceptable salt thereof as defined above for use as a medicament.

In a further aspect, the present invention concerns also the use of a compound of formula I or a pharmaceutically acceptable salt thereof for the manufacture of a medicament for the treatment of neurological and other disorders such as mentioned above.

In particular, the present invention concerns the use of a compound of formula I or a pharmaceutically acceptable salt thereof for the manufacture of a medicament for the treatment of epilepsy, Parkinson's disease, dyskinesia, migraine, tremor, essential tremor, bipolar disorders, chronic pain, neuropathic pain, or bronchial, asthmatic or allergic conditions.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg, preferably 25 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manisfestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

The term "Parkinsonian symptoms" relates to a syndrome characterised by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia, exposure to toxins/drugs and head injury. It is widely appreciated that the primary pathology underlying Parkinson's disease is degeneration, in the brain, of the dopaminergic projection from the substantia nigra to the striatum. This has led to the widespread use of dopamine-replacing agents (e.g. L-3,4-dihydroxyphenylalanine (L-DOPA) and dopamine agonists) as symptomatic treatments for Parkinson's disease and such treatments have been successful in increasing the quality of life of patients suffering from Parkinson's disease. However, dopamine-replacement treatments do have limitations, especially following long-term treatment. Problems can include a wearing-off of the anti-parkinsonian efficacy of the treatment and the appearance of a range of side-effects which manifest as abnormal involuntary movements, such as dyskinesias.

The term "dyskinesia" is defined as the development in a subject of abnormal involuntary movements. This appears in patients with Huntington's disease, in Parkinson's disease patients exposed to chronic dopamine replacement therapy, and in Schizophrenia patients exposed to chronic treatment with neuroleptics. Dyskinesias, as a whole, are characterised by the development in a subject of abnormal involuntary movements. One way in which dyskinesias may arise is as a side effect of dopamine replacement therapy for parkinsonism or other basal ganglia-related movement disorders.

The term "migraine" as used herein means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV ™), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain initiated by a pathological change in a nerve which signals the presence of a noxious stimulus when no such recognisable stimulus exists, giving rise to a false sensation of pain. In other words, it appears that the pain system has been turned on and cannot turn itself off.

The term "tics" refers to common and often disabling neurological disorders. They are frequently associated with behaviour difficulties, including obsessive-compulsive disorder, attention deficit hyperactivity disorder and impulse control. Tics are involuntary, sudden, rapid, repetitive, nonrhythmic stereotype movements or vocalizations. Tics are manifested in a variety of forms, with different durations and degrees of complexity. Simple motor tics are brief rapid movements that often involve only one muscle group. Complex motor tics are abrupt movements that involve either a cluster of simple movements or a more coordinated sequence of movements. Simple vocal tics include sounds such as grunting, barking, yelping, and that clearing. Complex vocal tics include syllables, phrases, repeating other people's words and repeating one's own words.

The activity of the compounds of formula I, or their pharmaceutically acceptable salts, as anticonvulsants can be determined in the audiogenic seizure model. The objective of this test is to evaluate the anticonvulsant potential of a compound by means of audiogenic seizures induced in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41). Results obtained with compounds of formula I are indicative of a strong pharmacological effect.

Another assay indicative of potential anticonvulsant activity is binding to levetiracetam binding site (LBS) as hereinafter described. As set forth in U.S. patent application Ser. Nos. 10/308,163 and 60/430,372 LBS has been identified as belonging to the family of SV2 proteins. As used herein reference to "LBS" is to be understood as including reference to SV2.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin); antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

Of particular interest in accordance with the present invention are combinations of at least one compound of formula I or a pharmaceutically acceptable salt thereof and at least one compound inducing neural inhibition mediated by $GABA_A$ receptors. The compounds of formula I exhibit a potentiating effect on the compounds inducing neural inhibition mediated by $GABA_A$ receptors enabling, in many cases, effective treatment of conditions and disorders under reduced risk of adverse effects.

Examples of compounds inducing neural inhibition mediated by $GABA_A$ receptors include the following: benzodiazepines, barbiturates, steroids, and anticonvulsants such as valproate, viagabatrine, tiagabine or pharmaceutical acceptable salts thereof.

Benzodiazepines include the 1,4-benzodiazepines, such as diazepam and clonazepam, and the 1,5-benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenyloin, ethotoin, etc), oxazolidines (trimethadione, etc.), succinimides (ethosuximide, etc.), phenacemides (phenacemide, acetylpheneturide, etc.), sulfonamides (sulthiame, acetoazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxil, sodium valproate, semi-sodium valproate, divalproex, clonazepam, phenobarbital, vigabatrine, tiagabine, amantadine.

For the preferred oral compositions, the daily dosage is in the range 3 to 3000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 3 mg to 3000 mg of compounds of formula I.

The daily dose can fall within a wide range of dosage units of compound of formula I and is generally in the range 3 to 3000 mg. However, it should be understood that the specific doses can be adapted to particular cases depending on the individual requirements, at the physician's discretion.

The LBS binding compounds provided by this invention and labelled derivatives thereof may be useful as standards and reagents in determining the ability of tested compounds (e.g., a potential pharmaceutical) to bind to the LBS receptor.

Labelled derivatives of LBS ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to LBS/SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A, but including SV2B and SV2C, to a putative agent and incubating the membranes or proteins or fragments and the agent with labelled compound of formula I. The method further comprises determining if the binding of the compound of formula I to the protein is inhibited by the putative agent, thereby identifying binding partners for the protein. Thus, the screening assays enable the identification of new drugs or compounds that interact with LBS/SV2. The present invention also provides photoactivable ligands of SV2/LBS. The method also includes a binding assay for the SV2 isoform SV2C, with labelled compound of formula I. While the SV2 isoform SV2A binds a series of levetiracetam-derived ligands with identical affinity to the LBS, the isoform SV2C shows selective binding to a subset of these ligands, and specifically has a high affinity binding to compound of formula I.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3H$, a fluorescent label, an enzyme, europium, biotin and other conventional labels for assays of this type. A particularly preferred compound for use in this aspect of the invention is [$^3H$]-(+)-4-(3-azido-2,4-difluorophenyl)-1-(1H-imidazol-1-ylmethyl)pyrrolidin-2-one ([$^3H$]-compound 7).

BRIEF DESCRIPTION OF THE DRAWINGS

Description of figures (in all figures (+)-4-(3-azido-2,4-difluorophenyl)-1-(1H-imidazol-1-ylmethyl)pyrrolidin-2-one is referred to as "compound 7" and "compound Z" stands for (2S)-2-[4-(3-azidophenyl)-2-oxopyrrolidin-1-yl]butanamide (referring to compound 86 in the PCT patent application WO 01/62726). L059 refers to (S)-(−)-α-ethyl-2-oxo-1-pyrrolidineacetamide, which is known under the International Nonproprietary Name of levetiracetam.

Figure 1:
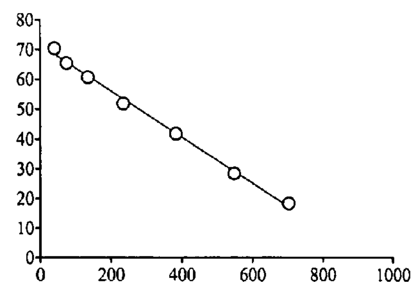
FIG. 1 depicts the saturation binding curves of [$^3H$]-compound 7 with rat brain membranes. Y-axis represents bound to free radioligand ratio: B/F (fmol/assay/nM) and X-axis represents bound radioligand: B (fmol/assay). Bmax=9.2 μmol/mg protein and Kd=13 nM.

Screening assays of the present invention include methods of identifying agents or compounds that compete for binding to the LBS (especially SV2A). Labelled compounds of formula I are useful in the methods of the invention as probes in assays to screen for new compounds or agents that bind to the LBS (especially SV2A). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of antiligand antibodies. The compounds may also include spacers or linkers in cases where the compounds are to be attached to a solid support. To identify agents or compounds which compete or interact with labelled ligands according to the invention for binding to the LBS (especially SV2A), intact cells, cellular or membrane fragments containing SV2A or the entire SV2 protein or a fragment comprising the LBS of the SV2 protein can be used. The agent or compound may be incubated with the cells, membranes, SV2 protein or fragment prior to, at the same time as, or after incubation with L059 or an analog or derivative thereof. Assays of the invention may be modified or prepared in any available format, including high-throughput screening (HTS) assays that monitor the binding of L059 or the binding of derivatives or analogs thereof to SV2 or to the LBS of the SV2 protein. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labelled ligand according to the invention to SV2 or a fragment of SV2 comprising the LBS or of L059, or derivatives or analogs thereof, to SV2 or a fragment of SV2 comprising the LBS. The inhibition of complex formation may be detected by a variety of techniques such as filtration assays, Flashplates (Perkin Elmer, scintillation proximity assays (SPA, Amersham Biosciences). For high-throughput screenings (HTS), scintillation proximity assay is a powerful method which uses microspheres coated with biological membranes and requires no separation or washing steps. This invention describes a method to use compound of formula I as a probe for binding assays, both low and high throughput, against the SV2 protein isoform SV2C. In addition, the demonstration of differential binding of ligands to SV2C over SV2A shows that it is possible to identify isoform specific compounds that can be utilized for the treatment of disease by selectively targeting SV2A or SV2C. The ligand for SV2C studies could be directly or indirectly labelled. The label could be any of a number of chemical moieties, such as $^3$H, a fluorescent label, a biotin or an enzyme. Labelled ligands are also useful for assessing the conformational state of SV2 after solubilization, purification, and chromatography. Moreover, the present invention provides photoactivable versions of the ligands for labelling and detection in biological samples. The photoactivable ligands may also be used to localize and purify SV2 from tissues, isolated cells, subcellular fractions and membranes. The photoactivable could also be used for SV2 crosslinking and identification of binding domains of LBS ligands.

Without further description, it is believed that one of ordinary skill in the art can, using the preceding description and the following illustrative examples, make and utilize the claimed invention. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

The following examples are provided for illustrative purposes.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^{1}H/^{13}C$ dual probehead or BRUKER DRX 400 FT NMR fitted with a SG Indigo$^2$ computer and a 5 mm inverse geometry $^{1}H/^{13}C/^{15}N$ triple probehead. The compound is studied in DMSO-$d_6$ (or $CDCl_3$) solution at a probe temperature of 313 K or 300 K and at a concentration of 20 mg/ml. The instrument is locked on the deuterium signal of DMSO-$d_6$ (or $CDCl_3$). Chemical shifts are given in ppm downfield from TMS taken as internal standard.

HPLC analyses are performed using one of the following systems:

- an Agilent 1100 series HPLC system mounted with an INERTSIL ODS 3 C18, DP 5 μm, 250×4.6 mm column. The gradient ran from 100% solvent A (acetonitrile, water, $H_3PO_4$ (5/95/0.001, v/v/v)) to 100% solvent B (acetonitrile, water, $H_3PO_4$ (95/5/0.001, v/v/v)) in 6 min with a hold at 100% B of 4 min. The flow rate is set at 2.5 ml/min. The chromatography is carried out at 35° C.
- a HP 1090 series HPLC system mounted with a HPLC Waters Symetry C18, 250×4.6 mm column. The gradient ran from 100% solvent A (MeOH, water, $H_3PO_4$ (15/85/0.00M, v/v/M)) to 100% solvent B (MeOH, water, $H_3PO_4$ (85/15/0.001 M, v/v/M)) in 10 min with a hold at 100% B of 10 min. The flow rate is set at 1 ml/min. The chromatography is carried out at 40° C.

Mass Spectrometric Measurements in LC/MS Mode are Performed as Follows:

HPLC Conditions

Analyses are performed using a WATERS Alliance HPLC system mounted with an INERTSIL ODS 3, DP 5 μm, 250×4.6 mm column.

The gradient ran from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μgr/ml. API spectra (+ or −) are performed using a FINNIGAN (San Jose, Calif., USA) LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization ($CI/CH_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in MeOH. For some molecules, the solvent is $CH_2Cl_2$ or DMSO, due to solubility problems.

Melting points are determined on a Büchi 535 or 545 Tottoli-type fusionometre, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at ±350 ml/min. Solvent mixtures as described in individual procedures.

The following abbreviations are used in the examples:

| Abbreviation | Meaning |
|---|---|
| AcOEt | Ethyl acetate |
| $CH_3CN$ | Acetonitrile |
| DMF | N,N-Dimethylformamide |
| NBS | N-bromosuccinimide |
| NCS | N-chlorosuccinimide |
| NIS | N-iodosuccinimide |
| TFA | Trifluoroacetic acid |
| THF | Tetrahydrofuran |

The following examples illustrate how the compounds covered by formula (I) can be synthesized.

Example 1

Synthesis of 4-Substituted 1-Hydroxymethylpyrrolidin-2-Ones

The starting pyrrolidones are synthesized using either conventional methods described in the literature (see for example: Gouliaev, A. H.; Monster, J. B.; Vedso, M.; Senning, A. *Org. Prep. Proceed. Int.* 1995, 27, 273-303.) or are described from PCT patent application WO01/62726-A2.

1.1. 4-(2-bromo-2,2-difluoro-ethyl)-1-hydroxymethyl-pyrrolidin-2-one a7.

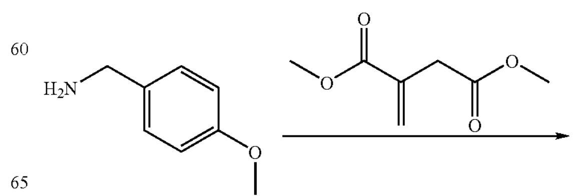

-continued

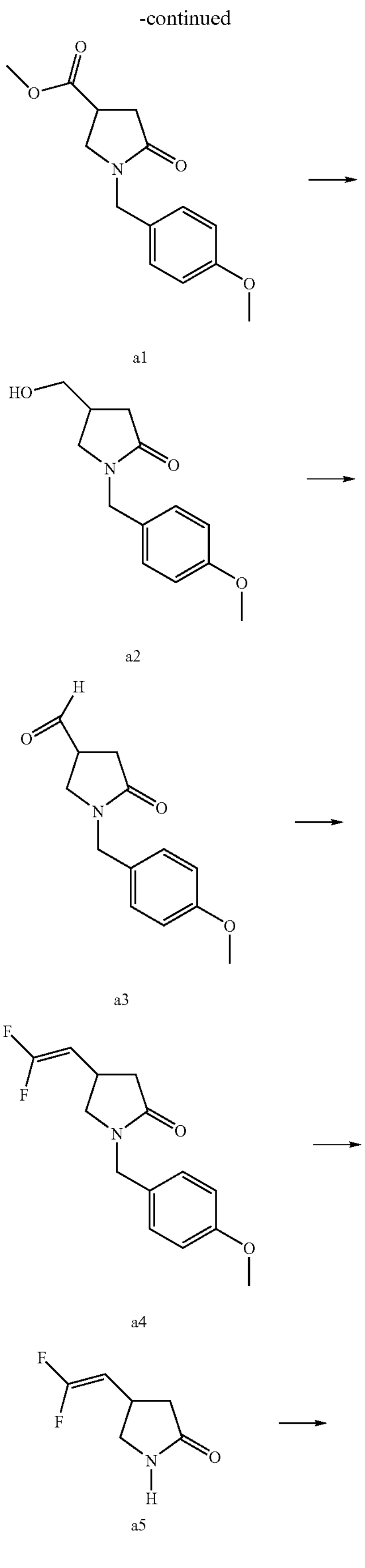

-continued

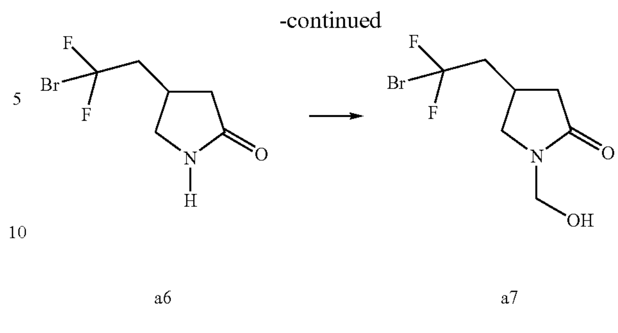

1.1.1. Synthesis of 1-(4-methoxy-benzyl)-5-oxo-pyrrolidine-3-carboxylic acid methyl ester a1

In a 250 ml three necked flask fitted with a magnetic stirrer and reflux condenser, under inert atmosphere, 10 g (73 mmol, 1 eq) of 4-methoxy-benzylamine and 12.7 g (81 mmol, 1.1 eq) of dimethyl itaconate are dissolved in 100 ml of MeOH. The mixture is brought to reflux for 10 h, and cooled down slowly to 20° C. over 4 h and concentrated to dryness. In a 250 ml three necked flask fitted with a magnetic stirrer and Rashig column and distillation arm, under inert atmosphere, the crude intermediate and 0.69 g (7.30 mmol, 0.1 eq) of 2-hydroxypyridine are dissolved in 200 ml of toluene. The mixture is brought to reflux and the methanol formed distilled off for 8 h, until no more methanol is collected. Temperature in the pot reached 112° C. The mixture is cooled down and concentrated to dryness to give the crude ester. It is purified by column chromatography on silicagel (AcOEt/n-Hexane: 1/1 (v/v)) to afford the pure ester a1 (16.48 g, 85.9%).

$^1H$ NMR (250 MHz, $C_2D_6SO$) δ (ppm): 2.40-2.60 (m, 2H); 3.25-3.50 (m, 3H); 3.60 (s, 3H); 3.75 (s, 3H); 4.20 (1H, d, J 13.8); 4.35 (1H, d, J 13.8); 6.87 (2H, d, J 7.4); 7.15 (2H, d, J 7.4).

1.1.2. Synthesis of 4-hydroxymethyl-1-(4-methoxy-benzyl)-pyrrolidin-2-one a2.

In a 250 ml three necked flask fitted with a magnetic stirrer and reflux condenser, under inert atmosphere, a solution of 8.48 g (32 mmol, 1 eq) of 1-(4-methoxy-benzyl)-5-oxo-pyrrolidine-3-carboxylic acid methyl ester a1 in 120 ml of EtOH is cooled down to 0° C. Solid $NaBH_4$ (3.6 g, 96 mol, 3 eq) is then added by portions over 1.5 h, all the while maintaining the temperature between 2 and 4° C. After 2 h, the temperature is raised to 12° C. for 1 h, and lowered again to 2-4° C. A saturated solution of $NH_4Cl$ (240 ml) is added dropwise over 1 h, followed by 120 ml of acetone, and the mixture is left overnight at room temperature. The mixture is extracted by $CH_2Cl_2$ (3 times), dried on $MgSO_4$, filtered and concentrated in vacuo to afford the crude alcohol which is purified by chromatography on silicagel ($CH_2Cl_2$/MeOH: 95/05 (v/v)) to give the pure alcohol a2 (4.3 g, 57%).

$^1H$ NMR (250 MHz, $C_2D_6SO$) δ (ppm): 2.15 (1H, dd, J 7.4); 2.40-2.60 (m, 2H); 2.95 (1H, dd, J 3.7; 9.2); 3.25-3.50 (m, 3H with solvent signal); 3.70 (s, 3H); 4.20 (1H, d, J 13.8); 4.35 (1H, d, J 13.8); 4.65 (1H, t, J 4.6); 6.87 (2H, d, J 7.4); 7.20 (2H, d, J 7.4).

1.1.3. Synthesis of 1-(4-methoxy-benzyl)-5-oxo-pyrrolidine-3-carbaldehyde a3.

In a three necked flask, under argon, a solution 4-hydroxymethyl-1-(4-methoxy-benzyl)-pyrrolidin-2-one a2 (4.3 g, 0.018 mol) and $Et_3N$ (8.9 ml) in $CH_2Cl_2$ (25 ml) is cooled down to −10° C. Pyridine-$SO_3$ (10.1 g, 0.064 mol, 3.5 eq) is added by portions and the temperature raised up to 1° C. After 3 h at −10° C., the reaction is quenched with water (100 ml) and extracted with $CH_2Cl_2$ (3 times). The organic phase is washed with successively a 1M solution of $KHSO_4$, water, brine, dried over $MgSO_4$, filtered and evaporated in vacuo to give the crude aldehyde a3 (3.2 g, 87%). It is dried several times by azeotropic distillation with toluene and used as such in the next step.

$^1H$ NMR (250 MHz, $C_2D_6SO$) δ (ppm): δ 2.45-2.60 (m, 2H); 3.25-3.55 (m, 3H); 3.75 (s, 3H); 4.30 (2H, s); 6.80 (2H, d, J 7.4); 7.20 (2H, d, J 7.4); 9.60 (s, 1H).

1.1.4. Synthesis of 4-(2,2-difluoro-vinyl)-1-(4-methoxy-benzyl)-pyrrolidin-2-one a4.

In a three necked flask under argon, $(Me_2N)_3P$ (11.53 ml, 0.063 mol) is added to a solution of $CF_2Br_2$ (6.6 g, 0.031 mol) in THF (30 ml) at −78° C. (appearance of a white precipitate) and warmed to room temperature. A solution of the 1-(4-methoxy-benzyl)-5-oxo-pyrrolidine-3-carbaldehyde a3 (3.7 g, 0.016 mol) in THF (30 ml) is added dropwise to the pre-formed phosphonium salt. After 1 h, the reaction mixture is filtered through celite and concentrated in vacuo. The reaction mixture is diluted with hexane, washed with brine, dried over $MgSO_4$ and concentrated in vacuo to afford the crude olefin which is purified by column chromatography on silicagel ($CH_2Cl_2$/MeOH: 99/01 (v/v)) to afford 2.45 g of the difluorovinyl derivative a4 (58%).

$^1H$ NMR (250 MHz, $C_2D_6SO$) δ (ppm): 2.15 (1H, dd, J 15.0; 7.5); 2.42-2.55 (1H, m+solvent signal); 2.93 (1H, dd, J 10.0; 7.5); 2.97-3.10 (1H, m); 3.35 (1H, dd, J 10.0; 7.5); 3.71 (s, 3H); 4.24 (1H, d, J 15.0); 4.27 (1H, d, J 15.0); 4.60 (1H, ddd, J 25.0; 7.5, 2.5); 6.86 (2H, d, J 7.4); 7.12 (2H, d, J 7.4).

1.1.5. Synthesis of 4-(2,2-difluoro-vinyl)-pyrrolidin-2-one a5.

In a 200 ml three necked flask fitted with a magnetic stirrer, under inert atmosphere, cerium ammonium nitrate (11.2 g, 0.02 mol, 3 eq) is added to a solution of 4-(2,2-difluoro-vinyl)-1-(4-methoxy-benzyl)-pyrrolidin-2-one a4 (1.8 g, 6.8 mmol in MeCN/$H_2O$ (respectively 70 ml/110 ml) cooled at 4° C. After 5 h at 10° C., the reaction mixture is diluted with water, extracted with AcOEt, dried on $MgSO_4$ and concentrated in vacuo. The residue is diluted with toluene, the solid is filtrated and the solvent is evaporated. The residue is purified by chromatography on silicagel ($CH_2Cl_2$/MeOH: 99/01 (v/v)) to afford fraction A1 (0.5 g of the expected compound) and fraction B (0.7 g of a mixture of synthetic intermediates and starting materials). Fraction B is again reacted with cerium ammonium nitrate as above (CAN: 0.78 g, MeCN (30 ml), $H_2O$ (50 ml)) to afford after purification, another fraction A2 (0.3 g). Fractions A1+A2 put together give 0.8 g of 4-(2,2-difluoro-vinyl)-pyrrolidin-2-one as (81%) contaminated by traces of 4-methoxybenzoic acid.

LC/MS ($MH^+$): 148.

1.1.6. Synthesis of 4-(2-bromo-2,2-difluoro-ethyl)-pyrrolidin-2-one a6.

In a 50 ml three necked flask fitted with a magnetic stirrer, under inert atmosphere, 0.1 g of 4-(2,2-difluoro-vinyl)-pyrrolidin-2-one a5 (0.6 mmol) is heated in HBr (62% w/w in $H_2O$, 10 ml) for 0.75 h at reflux. The reaction mixture is cooled down to room temperature, diluted with water and extracted with $CH_2Cl_2$ (3 times), dried over $MgSO_4$, filtered and concentrated in vacuo to afford 0.076 g of 4-(2-bromo-2,2-difluoro-ethyl)-pyrrolidin-2-one a6 (49%).

GC/MS ($M^{+\bullet}$): 227/229.

1.1.7. Synthesis of 4-(2-bromo-2,2-difluoro-ethyl)-1-hydroxymethyl-pyrrolidin-2-one a7.

The following example is representative of the hydroxymethylation of a pyrrolidin-2-one derivative.

In a 50 ml three necked flask fitted with a magnetic stirrer, under inert atmosphere, a solution of 4-(2-bromo-2,2-difluoro-ethyl)-pyrrolidin-2-one a6 (0.46 g, 2 mmol), paraformaldehyde (0.12 g) and TMSCl (10 ml) is heated at 60° C. for 1 h. The reaction mixture is evaporated to give the crude 4-(2-bromo-2,2-difluoro-ethyl)-1-hydroxymethyl-pyrrolidin-2-one a7 (0.48 g, 92%).

$^1H$ NMR (250 MHz, $C_2D_6SO$) δ (ppm): 2.10-2.23 (1H, m); 2.40-2.80 (4H, m+solvent signal); 3.21 (1H, dd, J 10.0; 7.5); 3.57 (1H, dd, J 10.0; 7.5); 4.53 (1H, d, J 10.0); 4.60 (1H, d, J 10.0).

The following compounds may be synthesized according to the same method: 1-(hydroxymethyl)-4-(3,4,5-trifluorophenyl)pyrrolidin-2-one; 1-hydroxymethyl-4-propyl-pyrrolidin-2-one; 1-hydroxymethyl-4-phenyl-pyrrolidin-2-one; 4-(3-chloro-phenyl)-1-hydroxymethyl-pyrrolidin-2-one; 4-(3-fluoro-phenyl)-1-hydroxymethyl-pyrrolidin-2-one; 4-(4-chloro-phenyl)-1-hydroxymethyl-pyrrolidin-2-one; 4-(4-fluoro-phenyl)-1-hydroxymethyl-pyrrolidin-2-one; 4-(3,5-difluoro-phenyl)-1-hydroxymethyl-pyrrolidin-2-one; 1-hydroxymethyl-4-(2,3,5-trifluoro-phenyl)-pyrrolidin-2-one; 1-hydroxymethyl-4-(2,3,4-trifluoro-phenyl)-pyrrolidin-2-one; 4-(3-chloro-4-fluoro-phenyl)-1-hydroxymethyl-pyrrolidin-2-one; 4-(3,4-difluoro-phenyl)-1-hydroxymethyl-pyrrolidin-2-one; 1-hydroxymethyl-4-(2,4,5-trifluoro-phenyl)-pyrrolidin-2-one and 4-(3-azido-2,4,6-trifluoro-phenyl)-1-hydroxymethyl-pyrrolidin-2-one.

1.2. Synthesis of 4-(3-azido-2,4-difluoro-phenyl)-1-hydroxymethyl-pyrrolidin-2-one a15

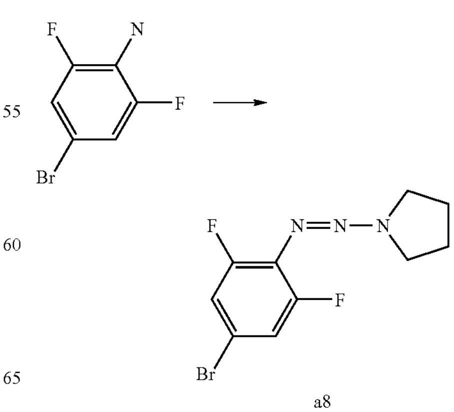

-continued

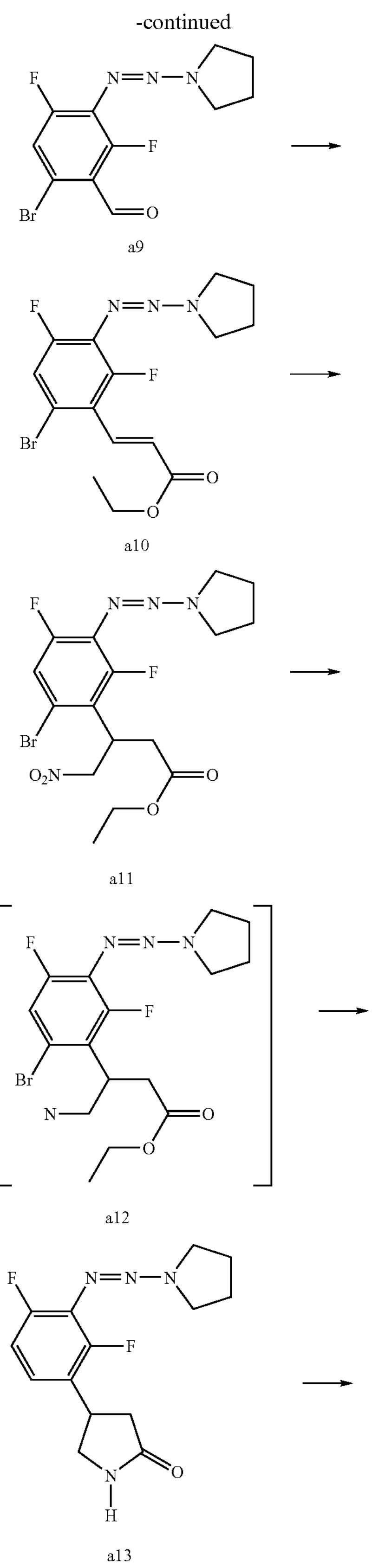

-continued

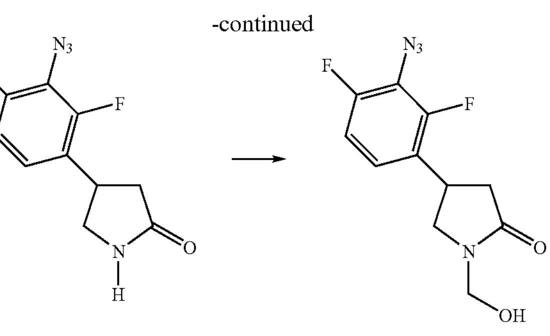

1.2.1. Synthesis of (4-Bromo-2,6-difluoro-phenyl)-pyrrolidin-1-yl-diazene a8.

In a 200 ml three necked flask fitted with a magnetic stirrer, under inert atmosphere, HCl (13 M, 10 ml) is added at −5° C. to a solution of 4-bromo-2,6-difluoroaniline (5.45 g, 0.026 mol) in ether. $NaNO_2$ (3.62 g, 0.056 mol) in water (8 ml) is added carefully while keeping the temperature below 0° C. After 0.5 h at 0° C., the reaction mixture is rapidly separated and the organic layer is added onto a solution of pyrrolidine (8.8 ml) and KOH (2M, 66 ml) cooled at −15° C. The temperature increased at maximum −10° C. The mixture is allowed to reach 0° C. and after 0.5 h, it is extracted with ether and the organic layer is dried over $MgSO_4$, filtered and concentrated in vacuo. The crude triazene is purified by chromatography on silicagel ($CH_2Cl_2$/hexane: 30/70 (v/v)) to give 5.46 g of (4-bromo-2,6-difluoro-phenyl)-pyrrolidin-1-yl-diazene a8 (73%).

GC/MS ($M^{+\bullet}$): 289/291

1.2.2. Synthesis of 6-bromo-2,4-difluoro-3-(pyrrolidin-1-ylazo)-benzaldehyde a9.

In a 200 ml three necked flask fitted with a magnetic stirrer, under inert atmosphere, (4-bromo-2,6-difluoro-phenyl)-pyrrolidin-1-yl-diazene a8 (6.06 g, 0.021 mol.) in THF (50 ml) is added to a solution of diisopropylamide (2 M in THF, 12.5 ml) cooled at −78° C. After 2 h at this temperature, dry DMF (3.2 ml) is added to the green solution. After 1 h, it is poured into water (200 ml), extracted with ether (3×200 ml) and the organic phase is dried over $MgSO_4$, filtered and concentrated in vacuo to give the crude aldehyde a9 (6.62 g, 99%).

GC/MS ($M^{+\bullet}$): 317/319.

1.2.3. Synthesis of 3-[6-bromo-2,4-difluoro-3-(pyrrolidin-1-ylazo)-phenyl]-acrylic acid ethyl ester a10

In a 0.3 l three necked flask fitted with a magnetical stirrer and dropping funnel under inert atmosphere, 6.62 g (20.8 mmol, 1 eq) of 6-bromo-2,4-difluoro-3-(pyrrolidin-1-ylazo)-benzaldehyde a9 are dissolved in THF (100 ml) and cooled down to 0° C. Ethyl (triphenylphosphoranylidene)acetate (9.43 g, 1.3 eq) is then added under efficient stirring, the temperature raising to 10° C. The mixture is kept under stirring one hour at 0° C., and then overnight at room temperature. The mixture is concentrated to dryness, the residue suspended in diethyl ether, the triphenylphospine oxide is filtered off and the filtrate concentrated to dryness. The residue is purified by PrepLC on silicagel ($CH_2Cl_2$/pentane:

50/50 (v/v)) to give 4.17 g of pure of 3-[6-bromo-2,4-difluoro-3-(pyrrolidin-1-ylazo)-phenyl]-acrylic acid ethyl ester a10 (47%).

GC/MS ($M^{+\bullet}$): 387/389.

1.2.4. Synthesis of 3-[6-bromo-2,4-difluoro-3-(pyrrolidin-1-ylazo)-phenyl]-4-nitro-butyric acid ethyl ester a11

In a 500 ml three necked flask fitted with reflux condenser, a magnetic stirrer and dropping funnel under inert atmosphere, 10.14 g (26 mmol, 1 eq) of 3-[6-bromo-2,4-difluoro-3-(pyrrolidin-1-ylazo)-phenyl]-acrylic acid ethyl ester a10 are dissolved in 25 ml of nitromethane. Diazabicycloundecene (4 ml, 1 eq) is then added dropwise under efficient stirring, keeping the temperature below 25° C. (ice/water bath). The deep red mixture is stirred overnight at room temperature. The mixture is diluted with diethyl ether, washed with 1N HCl, the aqueous phase reextracted twice with ethyl ether. The combined organic phases are dried over magnesium sulfate, filtered and concentrated to dryness to give 12.6 g of crude nitro ester. The residue is purified by chromatography on silicagel ($CH_2Cl_2$/pentane: 50/50 (v/v)) to give 10.6 g of 3-[6-bromo-2,4-difluoro-3-(pyrrolidin-1-ylazo)-phenyl]-4-nitro-butyric acid ethyl ester a11 (91%).

LC/MS ($MH^+$): 449/451.

1.2.5. Synthesis of 4-[2,4-difluoro-3-(pyrrolidin-1-ylazo)-phenyl]-pyrrolidin-2-one a13

In a 500 ml pressure jar, under inert atmosphere, 6.29 g (14 mmol) of 3-[6-bromo-2,4-difluoro-3-(pyrrolidin-1-ylazo)-phenyl]-4-nitro-butyric acid ethyl ester all and $Et_3N$ (5.9 ml) are dissolved in 120 ml of ethanol. A suspension of 6 g of predried (3 times, ethanol) Raney nickel is added and the mixture hydrogenated on a Parr hydrogenator at a maximum of 20 psi $H_2$ pressure (strongly exothermically reaction, ice/water cooling required). The mixture is degassed, filtered on a Celite/Norite pad, and the filtrate concentrated in vacuo, to give 6.2 g of crude. It is again hydrogenated as described above to remove the bromide using 0.59 g of Pd/C instead of Raney nickel during 0.75 h on a Parr hydrogenator at a maximum of 40 psi $H_2$ pressure. The crude amino-ester is purified by chromatography on silicagel ($CH_2Cl_2$/EtOH/$NH_4OH$: 94.5/5/0.5 (v/v/v)) to give 3.6 g of 4-amino-3-[2,4-difluoro-3-(pyrrolidin-1-ylazo)-phenyl]-butyric acid ethyl ester a12 (76% yield) used as such in the next step.

LC/MS ($MH^+$): 341.

In a 100 ml flask fitted with reflux condenser and magnetic stirrer, 1.03 g (3 mmol) of the amino-ester a12 are dissolved in 10 ml of toluene, and the mixture is refluxed for 16 h. The solution is concentrated to dryness to give 0.82 g (92%) of pure 4-[2,4-difluoro-3-(pyrrolidin-1-ylazo)-phenyl]-pyrrolidin-2-one a13. GC/MS ($M^{+\bullet}$): 294.

1.2.6. Synthesis of 4-(3-azido-2,4-difluoro-phenyl)-pyrrolidin-2-one a14.

In a 25 ml three necked flask fitted with a magnetic stirrer, under inert atmosphere, $NaN_3$ (0.133 g, 2 mmol) is added to a solution of 4-[2,4-difluoro-3-(pyrrolidin-1-ylazo)-phenyl]-pyrrolidin-2-one a13 (0.2 g, 0.68 mmol) and HCl (1N, 10 ml) at room temperature. After 1.5 h, the reaction mixture is quenched by NaOH (1N, 10 ml), extracted with $CH_2Cl_2$ (3 times), and the organic layer is dried on $MgSO_4$, filtered and concentrated in vacuo to afford the crude 4-(3-azido-2,4-difluoro-phenyl)-pyrrolidin-2-one a14 which is used as such in the next step.

GC/MS ($M^{+\bullet}$): 238.

1.2.7. Synthesis of 4-(3-azido-2,4-difluoro-phenyl)-1-hydroxymethyl-pyrrolidin-2-one a15

The following example is representative for the hydroxymethylation of a pyrrolidin-2-one derivative.

In a 50 ml three necked flask fitted with a magnetic stirrer, under inert atmosphere, a solution of 4-(3-azido-2,4-difluoro-phenyl)-pyrrolidin-2-one a14 (1.84 g, 7.73 mmol), formaldehyde (35% w/w in water, 2.3 g) and NaOH (0.015 g) in EtOH (20 ml) is heated at 60° C. for 3 h. The reaction mixture is evaporated and dried azeotropically with toluene to give the crude alcohol which is purified by chromatography on silicagel ($CH_2Cl_2$/MeOH: 98/02 (v/v)) to give 4-(3-azido-2,4-difluoro-phenyl)-1-hydroxymethyl-pyrrolidin-2-one a15 (1.64 g, 79%).

GC/MS ($M^{+\bullet}$): 268.

Example 2

Synthesis of 1-imidazol-1-ylmethyl-pyrrolidin-2-ones from 1-hydroxymethyl-pyrrolidin-2-ones 2.1. Synthesis of 4-(3-azido-2,4-difluoro-phenyl)-1-imidazol-1-ylmethyl-pyrrolidin-2-one using α-chloroenamines The following example is representative for the synthesis of 1-imidazol-1-ylmethyl-pyrrolidin-2-ones derivatives.

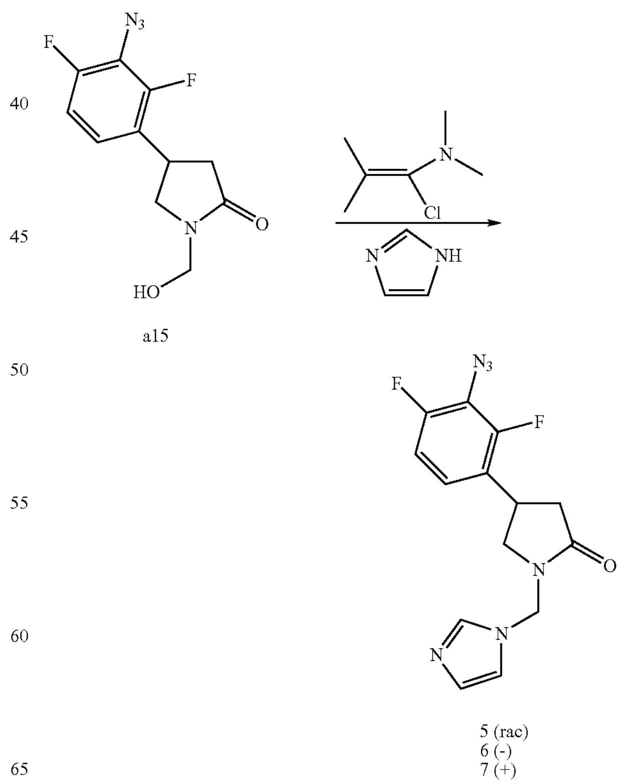

In a 100 ml three necked flask fitted with a magnetic stirrer, under inert atmosphere, distilled tetramethyl-chloro-enamine (1.1 ml, 8.5 mmol) is added to a solution of 4-(3-azido-2,4-difluoro-phenyl)-1-hydroxymethyl-pyrrolidin-2-one a15 (1.9 g, 7.08 mmol) in $CH_2Cl_2$ (45 ml) at 0° C. After 3.5 h, the mixture is transferred via a canula into a second three necked flask fitted with a magnetic stirrer, under inert atmosphere, containing a solution of imidazole (2.4 g, 35.4 mmol) in $CH_2Cl_2$ (45 ml) at room temperature. The temperature raised up to 28° C. and a precipitate appears. After 1 h, the reaction mixture is filtered, evaporated in vacuo, diluted with $CH_2Cl_2$ and the organic layer is washed with water, dried over $MgSO_4$, filtered and evaporated in vacuo. The residue is purified by chromatography on silicagel ($CH_2Cl_2$/EtOH/$NH_4OH$: 93.5/06/0.5 (v/v)) to afford 4-(3-azido-2,4-difluoro-phenyl)-1-imidazol-1-ylmethyl-pyrrolidin-2-one 5 (1.66 g, 75%). The racemate is resolved by preparative chiral chromatography (Chiralpak AD, benzine/EtOH) and the enantiomers are recrystallized successively in toluene and AcOEt to afford the two enantiomers 6 (first eluted) and 7 (second eluted) as white solids (0.5 g and 0.45 g).

LC/MS ($MH^+$): 319.

Alternatively when mixtures of isomers are obtained (racemate, regioisomers, . . . ) the compounds may be purified by preparative HPLC on silicagel or on chiral phase.

2.2. Synthesis of 1-[(4-chloro-1H-imidazol-1-yl)methyl]-4-(3,4,5-trifluorophenyl)-pyrrolidin-2-one 72 using thionyl chloride Alternatively to method 2.1, 1-imidazol-1-ylmethyl-pyrrolidin-2-ones derivatives can also be obtained by a similar reaction of the hydroxymethyl derivative with successively thionyl chloride in toluene for 16 h at room temperature followed by quenching of the chloromethyl derivative with an imidazole in the presence of $Et_3N$ at room temperature. For example, 1-hydroxymethyl-4-(3,4,5-trifluoro-phenyl)-pyrrolidin-2-one reacts with thionyl chloride and 4-chloroimidazole to afford 1-[(4-chloro-1H-imidazol-1-yl)methyl]-4-(3,4,5-trifluorophenyl)-pyrrolidin-2-one 72

LC/MS ($MH^+$): 330/332.

2.3. Synthesis of 4-(2,2-difluorovinyl)-1-(1H-imidazol-1-ylmethyl)pyrrolidin-2-one 18 by functional group transformation

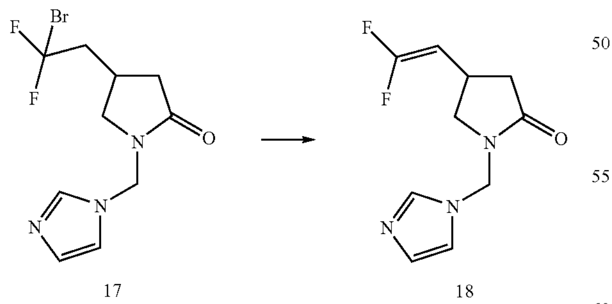

In a 50 ml three necked flask fitted with a magnetic stirrer, under inert atmosphere, 4-(2-bromo-2,2-difluoro-ethyl)-1-(1H-imidazol-1-ylmethyl)-pyrrolidin-2-one 17 (0.16 g, 0.52 mmol) and diazabicyclo [5.4.0]undec-7-ene (0.1 ml, 0.62 mmol) in $CHCl_3$ (0.5 ml) are stirred overnight at room temperature. The reaction mixture is filtered, evaporated in vacuo, diluted with $CH_2Cl_2$ and the organic layer is washed with water, dried over $MgSO_4$, filtered and evaporated in vacuo. The residue is purified by chromatography on silicagel ($CH_2Cl_2$/EtOH/$NH_4OH$: 93.5/06/0.5 (v/v/v)) to afford 4-(2,2-difluorovinyl)-1-(1H-imidazol-1-ylmethyl)pyrrolidin-2-one 18 (0.092 g, 80%) which is crystallized as a maleic salt in THF.

LC/MS ($MH^+$): 228.

Alternatively, other functional group transformation can be used to synthesize 1-imidazol-1-ylmethyl-pyrrolidin-2-one derivatives:

(a) methylthio-imidazole derivatives can be oxidized using $NaIO_4$ in MeOH (eg. for the synthesis of 1-{[2-(methylsulfinyl)-1H-imidazol-1-yl]methyl}-4-propylpyrrolidin-2-one 21);

(b) 1H-imidazole-2-carboxylic acid methyl ester can be transformed into the corresponding amides (by reaction with an amine in MeOH; eg. for the synthesis of 1-[(2-oxo-4-propylpyrrolidin-1-yl)methyl]-1H-imidazole-2-carboxamide 26) or into the corresponding alcohol (by reduction $NaBH_4$ in MeOH; eg. for the synthesis of 1-{[2-(hydroxymethyl)-1H-imidazol-1-yl]methyl}-4-propylpyrrolidin-2-one 37);

(c) nitro-imidazoles can be reduced by hydrogen in the presence of Pd/C into the corresponding amino-imidazoles (eg. for the synthesis of 1-[(2-amino-1H-imidazol-1-yl)methyl]-4-propylpyrrolidin-2-one 42).

Such transformations are within the competence of any person well skilled in the art of organic synthesis.

Example 3

Synthesis of 1-[1-(1H-imidazol-1-yl)cyclopropyl]pyrrolidin-2-one 23

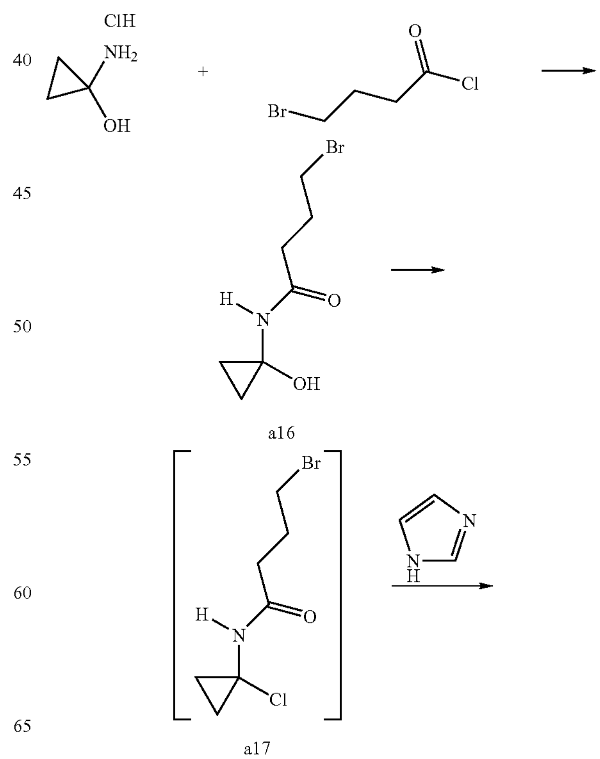

-continued

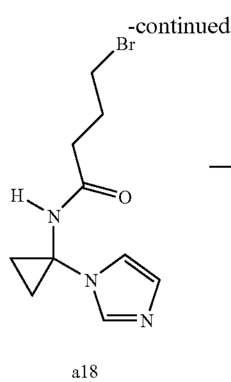

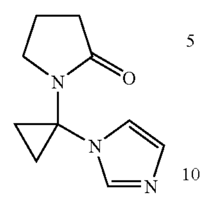

a18 23

3.1. Synthesis of 4-bromo-N-(1-hydroxy-cyclopropyl)-butyramide a16.

In a 50 ml three necked flask fitted with a magnetic stirrer, under inert atmosphere, 4-bromo-butyryl-chloride (1.69 g, 9.13 mmol) is added onto a suspension 1-aminocyclopropanol hydrochloride (1.0 g, 9.13 mmol; synthesized following the method of Matthies, D.; Buechling, U. in Arch. Pharm. (Weinheim Ger.) 1983, 316, 598-608) and $Et_3N$ (2.21 g, 0.022 mol. in dry THF (20 ml at 0° C.). After 4 h, the reaction mixture is left overnight in dry ice and another portion of 4-bromo-butyryl-chloride (0.34 g) and $Et_3N$ (0.44 g) are added. After 2 h at room temperature, the reaction mixture is cooled down to 0° C., filtrated and concentrated in vacuo to give the crude 4-bromo-N-(1-hydroxy-cyclopropyl)-butyramide a16 which is used in the next step without any further purification.

3.2. Synthesis of 4-bromo-N-(1-imidazol-1-yl-cyclopropyl)-butyramide a18.

In a 50 ml three necked flask fitted with a magnetic stirrer, under inert atmosphere, thionyl chloride (2.72 g, 0.023 mmol) is added to the crude 4-bromo-N-(1-hydroxy-cyclopropyl)-butyramide a16 (2.3 g, 9.13 mmol) in $CHCl_3$ (20 ml). After 3 h at room temperature, the light orange reaction mixture is evaporated, diluted in THF (5 ml) and added into another 50 ml three necked flask fitted with a magnetic stirrer, under inert atmosphere, containing a solution of imidazole (0.622 g, 9.1 mmol) and $Et_3N$ (2.8 g) in THF (20 ml) at room temperature. After 6 h, the reaction mixture is cooled down to 0° C., filtrated and concentrated in vacuo to give the crude 4-bromo-N-(1-imidazol-1-yl-cyclopropyl)-butyramide a18 (2.76 g) which is used in the next step without any further purification.

3.3. Synthesis of 1-[1-(1H-imidazol-1-yl)cyclopropyl]pyrrolidin-2-one 23

In a 50 ml three necked flask fitted with a magnetic stirrer, under inert atmosphere, the crude 4-bromo-N-(1-imidazol-1-yl-cyclopropyl)-butyramide a18 (2.76 g), $K_2CO_3$ (1.26 g, 9.1 mmol) and KI (0.0075 g) in DMF (25 ml) are heated 3 h at 60° C., 17 h at 80° C., cooled down to room temperature and concentrated in vacuo. The reaction mixture is diluted with $CH_2Cl_2$, filtered and concentrated in vacuo to give the crude pyrrolidone (1.7 g). The residue is purified by chromatography on silicagel ($CH_2Cl_2$/MeOH/$NH_4OH$: 95/4.5/05 (v/v/v)) to give, after treatment with HCl in ether (1 eq) and recrystallization in MeCN, 1-[1-(1H-imidazol-1-yl)cyclopropyl]pyrrolidin-2-one 23 (0.033 g, 7.5%) as an hydrochloride.

LC/MS ($MH^+$): 192.

Example 4

Synthesis and derivatisation of imidazol-1-yl-(2-oxo-4-propyl-pyrrolidin-1-yl)-acetic acid ethyl ester

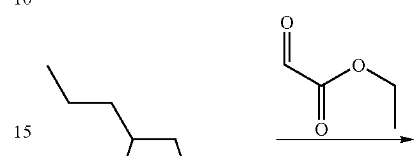

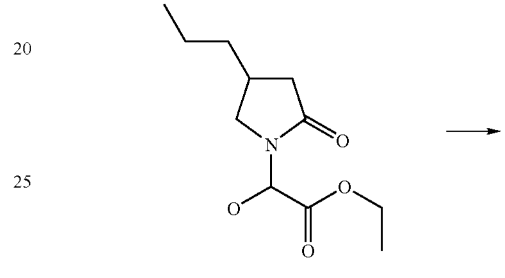

a19

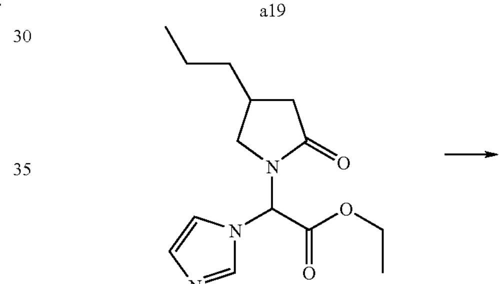

a20

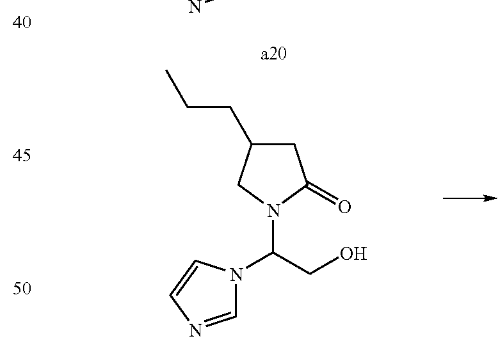

39

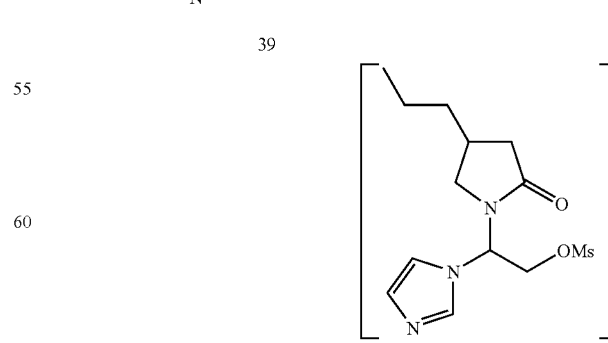

a21

-continued

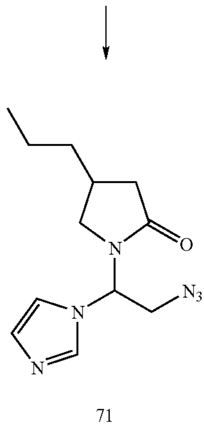

4.1. Synthesis of hydroxy-(2-oxo-4-propyl-pyrrolidin-1-yl)-acetic acid ethyl ester a19

In a 250 ml three necked flask fitted with a magnetic stirrer, under inert atmosphere, a mixture of 4-propyl-pyrrolidin-2-one (0.5 g, 3.9 mmol) and ethyl glyoxylate (50% in toluene, 2.4 ml, 11 mmol) in acetone is heated up at 60° C. for 6 h and another portion of ethyl glyoxylate (0.4 ml) is added. After 17 h at 50° C., the reaction mixture is concentrated in vacuo to give the crude hydroxy-(2-oxo-4-propyl-pyrrolidin-1-yl)-acetic acid ethyl ester a19 (2.02 g). It is used in the next step without any further purification.

$^1$H NMR $\delta_H$ (250 MHz, $CDCl_3$): 0.92 (3H, t, J 7.5); 1.25-1.50 (7H, m); 2.10-2.25 (1H, m); 2.25-2.50 (1H, m); 2.58 (1H, dd, J 10.0; 7.5); 2.85 (1H, dd, J 10.0; 7.5 for one diastereoisomer); 3.17 (1H, dd, J 7.5; 7.5 for one diastereoisomer); 3.20 (1H, dd, J 10.0; 7.5 for one diastereoisomer); 3.63 (1H, dd, J 7.5; 7.5 for one diastereoisomer); 4.32 (2H, q, J 7.5); 5.75 (1H, s).

4.2. Synthesis of imidazol-1-yl-(2-oxo-4-propyl-pyrrolidin-1-yl)-acetic acid ethyl ester a20

In a 50 ml three necked flask fitted with a magnetic stirrer, under inert atmosphere, the crude hydroxy-(2-oxo-4-propyl-pyrrolidin-1-yl)-acetic acid ethyl ester a19 (0.901 g, 3.9 mmol) and carbonyl-diimidazole (0.95 g, 5.9 mmol) in MeCN (20 ml) is allowed to react 48 h at room temperature and concentrated in vacuo. The reaction mixture is diluted with HCl (0.1 M) and extracted with $CH_2Cl_2$. The aqueous layer is basicified to pH 9 with solid $Na_2CO_3$, extracted with $CH_2Cl_2$, dried on $MgSO_4$, filtered and concentrated in vacuo. This residue is purified by chromatography on silicagel ($CH_2Cl_2$/MeOH/$NH_4OH$: 96/3.6/0.04 (v/v/v)) to give imidazol-1-yl-(2-oxo-4-propyl-pyrrolidin-1-yl)-acetic acid ethyl ester a20 (0.8 g, 82%).

LC/MS ($MH^+$): 280.

4.3. Synthesis of 1-(2-hydroxy-1-imidazol-1-yl-ethyl)-4-propyl-pyrrolidin-2-one 39

In a 500 ml three necked flask fitted with a magnetic stirrer, under inert atmosphere, $NaBH_4$ (1.92 g, 0.05 mol) is added by portions into a solution of imidazol-1-yl-(2-oxo-4-propyl-pyrrolidin-1-yl)-acetic acid ethyl ester a20 (9.4 g, 0.034 mol. in dry EtOH (200 ml) at 0° C. After 2.5 h, the reaction mixture is quenched carefully with a saturated solution of $NH_4Cl$ and the temperature raised up to 10° C. The solvent is evaporated to dryness and the residue is purified by chromatography on silicagel ($CH_2Cl_2$/MeOH: 95/05 (v/v)) to give 1-(2-hydroxy-1-imidazol-1-yl-ethyl)-4-propyl-pyrrolidin-2-one 39 (5.47, 68%).

LC/MS ($MH^+$): 238.

4.4. Synthesis of 1-(2-azido-1-imidazol-1-yl-ethyl)-4-propyl-pyrrolidin-2-one 71

In a 50 ml three necked flask fitted with a magnetic stirrer, under inert atmosphere, mesylchloride (0.36 g, 3.2 mmol) is added into a solution of 1-(2-hydroxy-1-imidazol-1-yl-ethyl)-4-propyl-pyrrolidin-2-one 39 (0.5 g, 2.1 mmol) and $Et_3N$ (0.59 ml) in $CH_2Cl_2$ (10 ml) at 0° C. After 1 h at 0° C., the white suspension is treated with saturated $K_2CO_3$, extracted with $CH_2Cl_2$, and the organic layer is dried on $MgSO_4$, filtered and concentrated in vacuo to give the mesylate a21 used as such in the next step.

In a 50 ml three necked flask fitted with a magnetic stirrer, under inert atmosphere, the crude mesylate a21 (0.6 g, 0.002 mol), $NaN_3$ (0.178 g, 0.002 mol) and NaI (0.017 g) in MeCN (5 ml) are heated 1.5 h at 60° C., left overnight at room temperature, heated at 60° C. for another 4 h, cooled down to room temperature and concentrated in vacuo. The reaction mixture is diluted with $CH_2Cl_2$, filtered and concentrated in vacuo to give the crude azide which is purified by chromatography on silicagel ($CH_2Cl_2$/MeOH/$NH_4OH$: 95/4.5/05 (v/v/v)) to give 1-(2-azido-1-imidazol-1-yl-ethyl)-4-propyl-pyrrolidin-2-one 71 (0.29 g, 51%).

LC/MS ($MH^+$): 263.

Example 5

Synthesis of 5-chloro-1-(1H-imidazol-1-ylmethyl)-1,3-dihydro-2H-indol-2-one 160

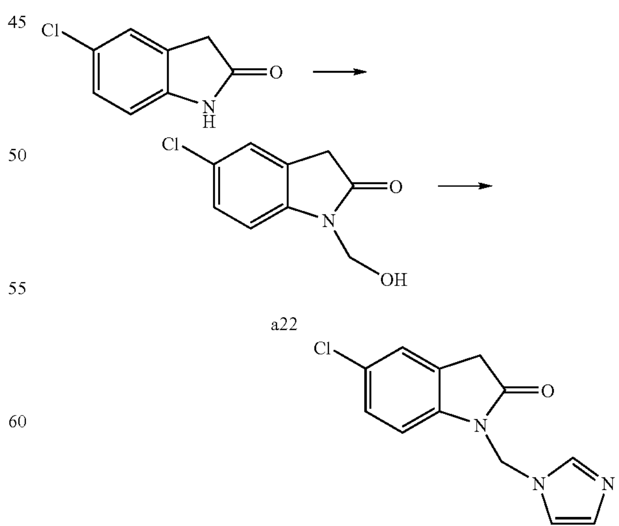

5.1. Synthesis of 5-chloro-1-hydroxymethyl-1,3-dihydro-indol-2-one a22

In an high pressure autoclave, 5-chloro-1,3-dihydro-indol-2-one (5 g, 0.029 mol), paraformaldehyde (1.07 g) and toluene (60 ml) are heated up to 120° C. for 4 h. The mixture is cooled down to room temperature, diluted with ether and filtrated to give 5-chloro-1-hydroxymethyl-1,3-dihydro-indol-2-one a22 as white crystals (4.03 g, 70%). $^1$H NMR $\delta_H$ (250 MHz, $C_2D_6SO$): 3.61 (2H, s); 5.04 (2H, d); 6.26 (1H, t); 7.08 (1H, d); 7.29-7.34 (2H, m).

The following compounds may be synthesized according to the same method: 1-(hydroxymethyl)-1,3-dihydro-2H-indol-2-one; 4-chloro-1-hydroxymethyl-1,3-dihydro-indol-2-one; 4-fluoro-1-hydroxymethyl-1,3-dihydro-indol-2-one; 5-bromo-1-hydroxymethyl-1,3-dihydro-indol-2-one; 1-hydroxymethyl-5-methyl-1,3-dihydro-indol-2-one and 1-hydroxymethyl-5-(2-methyl-thiazol-4-yl)-1,3-dihydro-indol-2-one.

5.2. Synthesis of 5-chloro-1-(1H-imidazol-1-ylmethyl)-1,3-dihydro-2H-indol-2-one 160

In a 50 ml three necked flask fitted with a magnetic stirrer, under inert atmosphere, the crude 5-chloro-1-hydroxymethyl-1,3-dihydro-indol-2-one a22 (4.0 g, 24 mmol) and carbonyl-diimidazole (4.26 g, 26.31 mmol) in MeCN (20 ml) are allowed to react 1 h at room temperature and concentrated in vacuo. The residue is purified by chromatography on silicagel ($CH_2Cl_2$/MeOH/$NH_4OH$: 96/3.6/0.4 (v/v)) to give 5-chloro-1-(1H-imidazol-1-ylmethyl)-1,3-dihydro-2H-indol-2-one 160 (2.82 g, 56%).

LC/MS ($MH^+$): 248/250.

Example 6

Synthesis of 4-(3,4,5-trifluorophenyl)-1-(1H-imidazol-1-ylmethyl)pyrrolidin-2-one 40

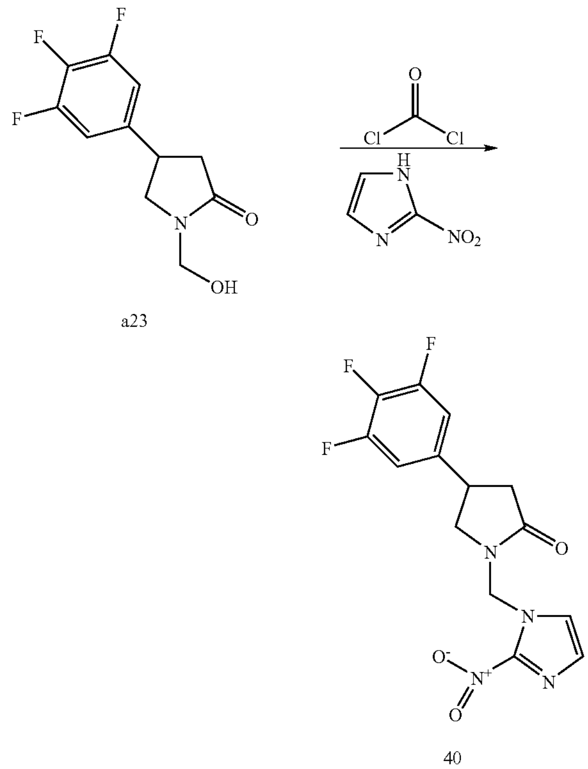

1-(hydroxymethyl)-4-(3,4,5-trifluorophenyl)pyrrolidin-2-one a23 is synthesized as described in Example 1.

LC/MS ($MH^+$): 246.

In a 100 ml three necked flask fitted with a magnetic stirrer, under inert atmosphere, phosgene (20 wt % in toluene, 0.95 eq, 2.02 mmol, 1 g) was added dropwise at room temperature to a solution of 2-nitroimidazole (2.5 eq, 5.1 mmol, 0.577 g) and triethylamine (3 eq, 6.1 mmol, 0.628 g, 0.85 ml) in THF (30 ml). After 0.5 h, 1-hydroxymethyl-4-(3,4,5-trifluoro-phenyl)-pyrrolidin-2-one a23 (1 eq, 2.1 mmol, 0.5 g) in THF (5 ml) was added dropwise at room temperature. After 4 h, the crude mixture was pored into a mixture of ice-cooled saturated sodium carbonate. After extraction (AcOEt), drying of the cumulated organic layers ($MgSO_4$), filtration and evaporation of the solvents, the crude mixture was purified by flash chromatography on silicagel (dichloromethane/methanol: 98/2 (v/v)) to give, after recrystallization in AcOEt, 1-(2-nitro-imidazol-1-ylmethyl)-4-(3,4,5-trifluoro-phenyl)-pyrrolidin-2-one 40 (138 mg, 20.3%).

LC/MS ($MH^+$): 341.

Example 7

Synthesis of 1-(1H-benzimidazol-1-ylmethyl)-4-propyl-pyrrolidin-2-one 91

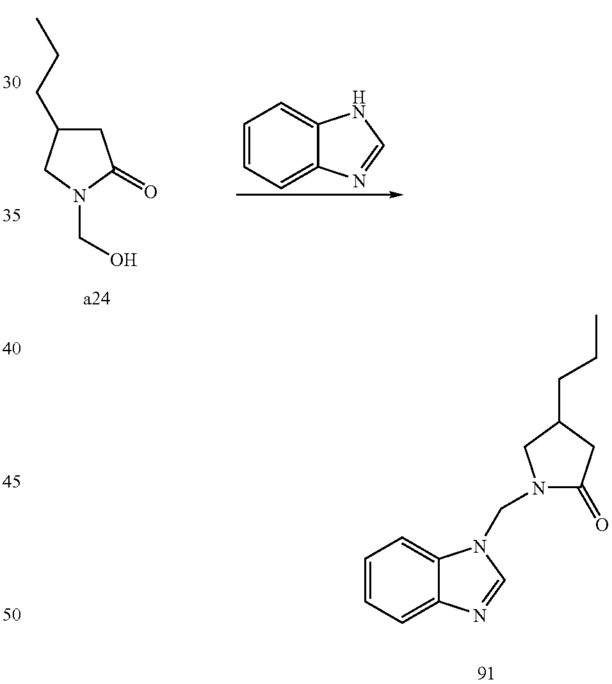

1-(hydroxymethyl)-4-propyl-pyrrolidin-2-one a24 is synthesized as described in Example 1.

LC/MS ($MH^+$): 158.

In a 50 ml three necked flask fitted with a magnetic stirrer, under inert atmosphere, a solution of 1-(hydroxymethyl)-4-propyl-pyrrolidin-2-one a24 (2.5 mmol, 400 mg) and benzimidazole (1 eq, 2.5 mmol, 300 mg) in acetic acid (20 ml) was heated at reflux overnight. After cooling, acetic acid was removed under vacuum, and the crude product was purified by preparative chromatography on silicagel to give 1-(1H-benzimidazol-1-ylmethyl)-4-propyl-pyrrolidin-2-one 91 after recrystallization in diisopropylether (16%).

LC/MS ($MH^+$): 258.

Example 8

Synthesis of 1-(1H-benzimidazol-1-ylmethyl)-1,3-dihydro-2H-indol-2-one 167

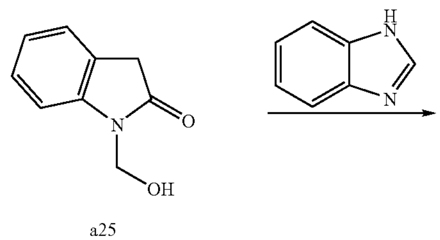

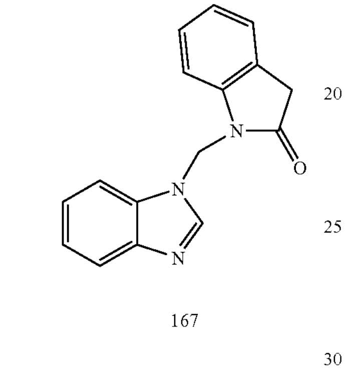

1-(hydroxymethyl)-1,3-dihydro-2H-indol-2-one a25 is synthesized as described in Example 1.

$^1$H NMR (250 MHz, $C_2D_6SO$) δppm: 3.60 (2H, s); 5.10 (2H, s); 6.20 (1H, s(broad)); 6.25-7.40 (4H, m).

A solution of 1-(hydroxymethyl)-1,3-dihydro-2H-indol-2-one a25 (1 eq, 3.06 mmol, 500 mg), benzimidazole (4 eq, 12.26 mmol, 1.45 g) and carbonyldiimidazole (1 eq, 3.06 mmol, 500 mg) in acetonitrile (3 ml) was irradiated in a microwave apparatus (CEM discover) for 10 minutes (100 w). After evaporation of the acetonitrile under reduced pressure, the crude product was purified by preparative HPLC on reverse phase to give 203 mg of 1-(1H-benzimidazol-1-ylmethyl)-1,3-dihydro-2H-indol-2-one 167 (25%) after recrystallization in diisopropylether.

LC/MS (MH$^+$): 263.

Example 9

Synthesis of 1-{[2-(methylthio)-1H-benzimidazol-1-yl]methyl}-4-propyl-pyrrolidin-2-one 90

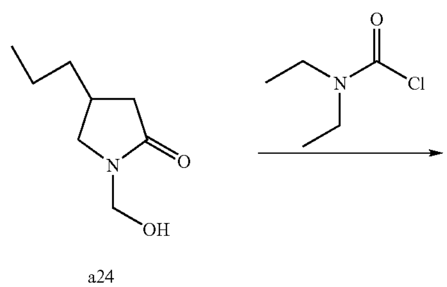

-continued

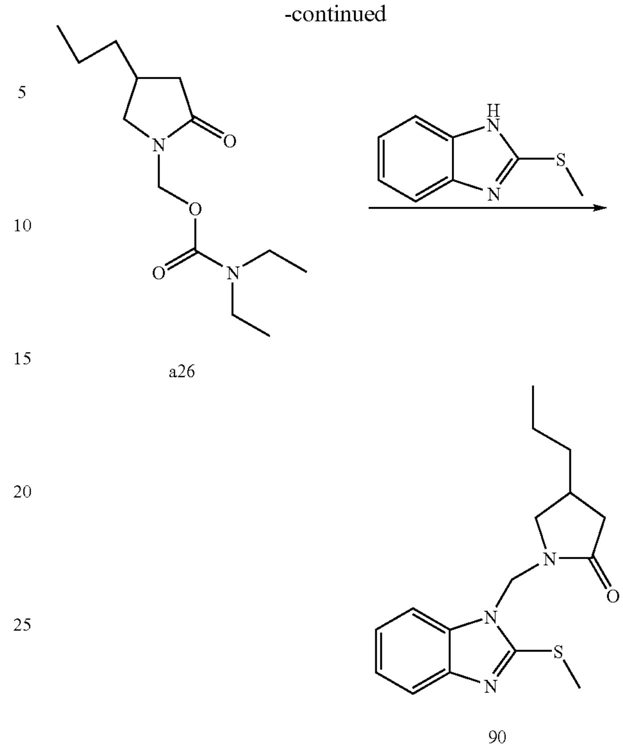

9.1. Synthesis of (2-oxo-4-propylpyrrolidin-1-yl)methyl diethylcarbamate a26

To a solution of 1-(hydroxymethyl)-4-propyl-pyrrolidin-2-one a24 (4 g, 25.44 mmol) and triethylamine (1.2 eq, 30.53 mmol, 3.089 g; 4.26 ml) in 25 ml of dichloromethane was added dropwise a solution of diethylcarbamyl chloride (1.1 eq, 27.99 mmol, 3.795 g, 3.55 ml) in dichloromethane (5 ml) at room temperature. The crude mixture was allowed to react under agitation and inert atmosphere overnight. Hydrolysis (15 ml of water), extraction ($CH_2Cl_2$), drying of the combinated organic layers ($MgSO_4$), filtration and solvent evaporation under reduced pressure gave (2-oxo-4-propylpyrrolidin-1-yl)methyl diethylcarbamate a26 (100%) which was used without any further purification.

$^1$H NMR (250 MHz, $CDCl_3$) δ ppm: 0.93 (3H, t); 1.22 (6H, q); 1.4 (4H, m); 2.10 (1H, dd); 2.34 (1H, quint); 2.53 (1H, dd); 3.20 (1H, dd); 3.45 (4H, m); 3.65 (1H, dd); 4.78 (2H, q).

9.2. Synthesis of 1-{[2-(methylthio)-1H-benzimidazol-1-yl]methyl}-4-propylpyrrolidin-2-one 90

A solution of (2-oxo-4-propylpyrrolidin-1-yl)methyl diethylcarbamate a26 (1 eq, 3.18 mmol, 0.5 g) and 2-(methylthio)-benzimidazole (1.25 eq, 3.90 mmol, 0.64 g) in acetonitrile (4 ml) was heated under reflux for 42 h. The solvent was evaporated under reduce pressure and purification by preparative chromatography on reverse phase afforded 390 mg of 1-{[2-(methylthio)-1H-benzimidazol-1-yl]methyl}-4-propylpyrrolidin-2-one 90 (HPLC purity (U.V.): 85%; Yield: 40.3%).

LC/MS (MH$^+$): 262.

Example 10

Synthesis of 1-[(2-propyl-benzimidazol-1-yl)methyl]-4-propylpyrrolidin-2-one 94

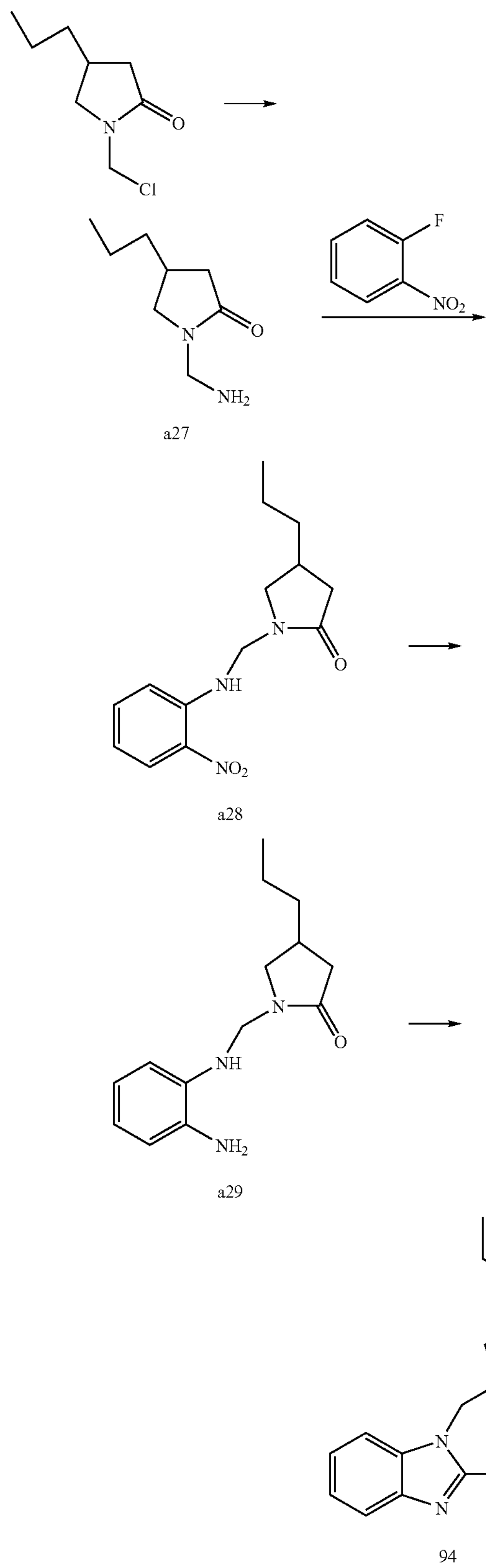

10.1. Synthesis of 1-aminomethyl-4-propyl-pyrrolidin-2-one a27

A solution of 1-chloromethyl-4-propyl-pyrrolidin-2-one (41.34 g, 0.235 mol) in toluene (350 ml) was added dropwise at −78° C. to liquid ammonia (300 ml). At the end of the addition, the temperature was raised slowly to room temperature and ammonia of the crude mixture was allowed to distilled at room temperature overnight. Filtration of the crude solution and subsequent evaporation lead to 55 g of the crude product a27 which was used without further purification.

LC/MS ($MH^+$): 157.

10.2. Synthesis of (2-nitrophenyl){(2-oxo-4-propyl-pyrrolidin-1-yl)methyl}amine a28

A mixture of 1-aminomethyl-4-propyl-pyrrolidin-2-one a27 (1 eq, 17.09 mmol, 2.67 g), 2-fluoro-nitrobenzene (1 eq, 17.09 mmol, 2.411 g, 1.802 ml) and triethylamine (1.1 eq, 18.8 mmol, 1.902 g, 2.62 ml) in dioxane (20 ml) was refluxed 48 h. After cooling, the crude mixture was filtrated and the dioxane was distilled under vacuum. The residue was purified by preparative chromatography on reverse phase to give (2-nitrophenyl){(2-oxo-4-propyl-pyrrolidin-1-yl)methyl}amine a28 (2.747 g, 58%).

LC/MS ($MH^+$): 278.

10.3. Synthesis of (2-aminophenyl){(2-oxo-4-propyl-pyrrolidin-1-yl)methyl}amine a29

Palladium on charcoal (10% wt) was added to a solution of (2-nitrophenyl){(2-oxo-4-propyl-pyrrolidin-1-yl)methyl}amine a28 (1 eq, 2.747 g, 9.905 mmol) and $NH_4CO_2H$ (5 eq, 49.9 mmol, 3.123 g) in water and methanol (1/1 (v/v), 35 ml). The resulting slurry was kept under agitation during 16 hours at room temperature, then filtration over celite and evaporation of the crude mixture gave (2-aminophenyl){(2-oxo-4-propyl-pyrrolidin-1-yl)methyl}amine a29 (2.232 g, 91%).

$^1H$ NMR (250 MHz, $CDCl_3$) δ ppm: 0.86 (3H, t); 1.20-1.35 (4H, m); 2.05 (1H, dd); 2.25 (1H, quint); 2.50 (1H, dd); 2.94 (1H, dd), 3.37 (2H, s); 3.43 (1H, dd); 4.14 (1H, s); 4.73 (2H, s), 6.70-6.84 (4H, m).

10.4. Synthesis of 1-[(substituted-benzimidazol-1-yl)methyl]-4-propylpyrrolidin-2-one 94

In a 50 ml three necked flask fitted with a magnetic stirrer, under inert atmosphere, a solution of (2-aminophenyl){(2-oxo-4-propyl-pyrrolidin-1-yl)methyl}amine a29 (1 eq, 0.69 mmol, 170 mg), propionaldehyde (1.4 eq, 0.966 mmol, 56 mg, 71 μl), acetic acid (0.3 ml) and dioxane (4 ml) was heated at 65° C. during 40 h. After cooling to room temperature, the solvent was removed under vacuum and the crude product was purified by preparative thin layer chromatography ($CH_2Cl_2$/MeOH/$NH_4OH$: 96/3.6/0.4) to give of 1-[(2-propyl)-benzimidazol-1-yl)methyl]-4-propylpyrrolidin-2-one 94 (65 mg, 33%).

LC/MS ($MH^+$): 300.

Example 11

Synthesis of 1-{[5-(hydroxymethyl)-1H-imidazol-1-yl]methyl}-4-propylpyrrolidin-2-one 80 and 1-{[4-(hydroxymethyl)-1H-imidazol-1-yl]methyl}-4-propylpyrrolidin-2-one 81

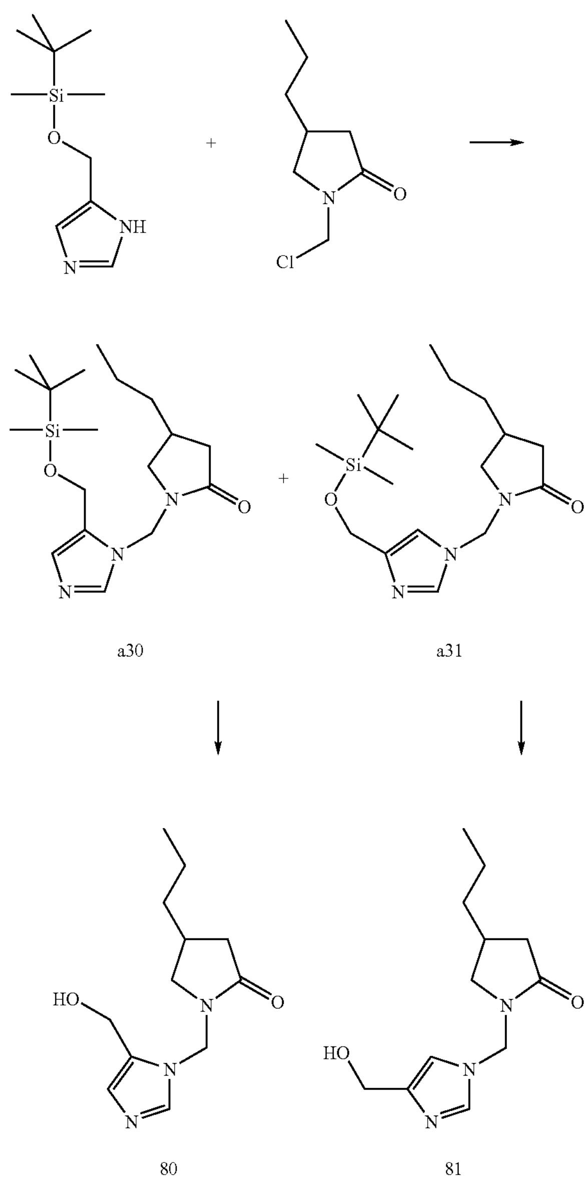

11.1. Synthesis of 1-{([5-({[tert-butyl(dimethyl)silyl]oxy}methyl)-1H-imidazol-1-yl]methyl}-4-propylpyrrolidin-2-one a30 and 1-{[4-({[tert-butyl(dimethyl)silyl]oxy}methyl)-1H-imidazol-1-yl]methyl}-4-propylpyrrolidin-2-one a31

In a 500 ml three necked flask fitted with a magnetic stirrer, under inert atmosphere, 4-(tert-butyl-dimethyl-silanyloxymethyl)-imidazole (21.9 g, 0.109 mol) in dry DMF (10 ml) is added to a suspension of NaH in dry DMF (280 ml) at 0° C. After 0.5 h, 4-propyl-1-chloromethyl-pyrrolidin-2-one (12.08 g, 0.0687 mol, from 4-propyl-1-hydroxymethyl-pyrrolidin-2-one, see procedure 2.1) in DMF (10 ml) is added dropwise at 0° C. and stirred 3.5 h at room temperature. After 1 h, the reaction mixture is filtered, evaporated in vacuo, diluted with $CH_2Cl_2$ and the organic layer is washed with water, dried over $MgSO_4$, filtered and evaporated in vacuo. The residue is purified by chromatography on silicagel ($CH_2Cl_2$/EtOH/$NH_4OH$: 93.5/06/0.5 (v/v)) and the two regioisomers are separated by chromatography on a chiral phase to afford 1-{[5-({[tert-butyl(dimethyl)silyl]oxy}methyl)-1H-imidazol-1-yl]methyl}-4-propylpyrrolidin-2-one a30 (8.9 g) and 1-{[4-({[tert-butyl(dimethyl)silyl]oxy}methyl)-1H-imidazol-1-yl]methyl}-4-propylpyrrolidin-2-one a31 (7.45 g).

Compound a30: $^1$H NMR 5 (250 MHz, $CDCl_3$): 0.02 (6H, s); 0.82-0.87 (12H, m); 1.17-1.37 (4H, m); 2.05 (1H, dd); 2.22-2.32 (1H, m); 2.49 (1H, dd); 2.91 (1H, dd); 3.49 (1H, dd); 4.63 (1H, s); 5.38 (2H, s); 6.84 (1H, s); 7.53 (1H, s).

Compound a31: $^1$H NMR 8 (250 MHz, $CDCl_3$): 0.15 (6H, s); 0.88-0.91 (12H, m); 1.20-1.45 (4H, m); 2.08 (1H, dd); 2.25-2.40 (1H, m); 2.52 (1H, dd); 2.90 (1H, dd); 3.43 (1H, dd); 4.67 (1H, s); 5.28 (1H, d); 5.32 (1H, d); 6.90 (1H, s); 7.49 (1H, s).

11.2 Synthesis of 1-{[5-(hydroxymethyl)-1H-imidazol-1-yl]methyl}-4-propylpyrrolidin-2-one 80

In a 250 ml three necked flask fitted with a magnetic stirrer, under inert atmosphere, 1-[5-(tert-butyl-dimethyl-silanyloxymethyl)-imidazol-1-ylmethyl]-4-propyl-pyrrolidin-2-one a30 (0.5 g, 0.0014 mol) is heated at 80° C. in a AcOH/THF/$H_2O$ mixture (9 ml/3 ml/3 ml) for 9 h, then stirred overnight at room temperature and concentrated in vacuo. The residue is dry by azeotropic distillation with toluene, purified by chromatography on silicagel ($CH_2Cl_2$/MeOH) and the solid is recrystallized from AcOEt to give 1-{[5-(hydroxymethyl)-1H-imidazol-1-yl]methyl}-4-propylpyrrolidin-2-one 80 (0.114 g, 35%).

LC/MS ($MH^+$): 238.

Alternatively, 1-{[4-(hydroxymethyl)-1H-imidazol-1-yl]methyl}-4-propylpyrrolidin-2-one 81 is obtained from 1-{[4-({[tert-butyl(dimethyl)silyl]oxy}methyl)-1H-imidazol-1-yl]methyl}-4-propylpyrrolidin-2-one a31 using a very similar procedure.

LC/MS ($MH^+$): 238.

Example 12

Synthesis of benzyl 1-[(2-oxo-4-propylpyrrolidin-1-yl)methyl]-1H-imidazol-5-ylcarbamate 83

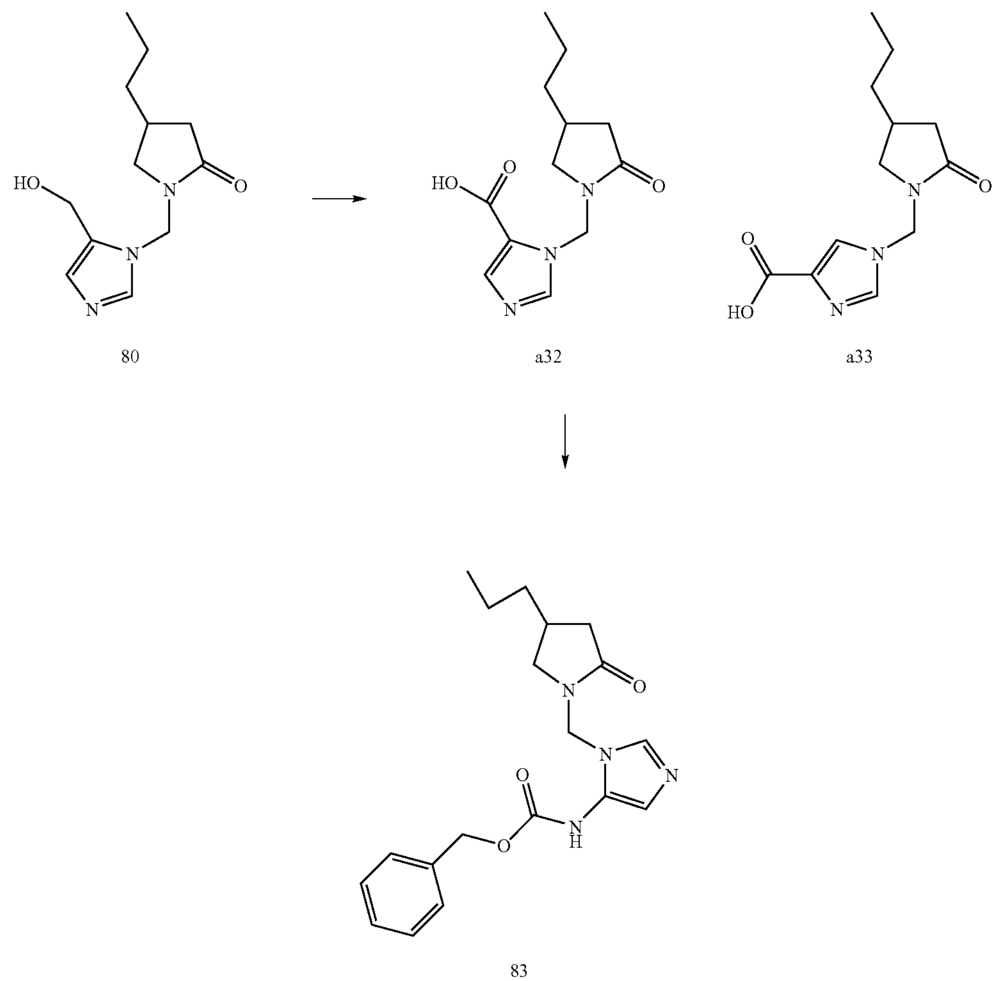

12.1 Synthesis of a 75/25 mixture of 1-[(2-oxo-4-propylpyrrolidin-1-yl)methyl]-1H-imidazole-5-carboxylic acid a32 and 1-[(2-oxo-4-propylpyrrolidin-1-yl)methyl]-1H-imidazole-4-carboxylic acid a33

In a 250 ml three necked flask fitted with a magnetic stirrer, under inert atmosphere, a mixture of 1-{[5-(hydroxymethyl)-1H-imidazol-1-yl]methyl}-4-propylpyrrolidin-2-one 80 (0.5 g, 0.0014 mol) in a $KH_2PO_4/Na_2HPO_4$ buffer (10 ml) and MeCN (10 ml) is heated at 60° C. Tetramethylpiperidine N-oxyde (0.131 g, 0.83 mmol) is added followed by $NaClO_2$ (1.17 g, 0.013 mol dissolved in 2 ml of water) and NaClO (0.155 g, 0.0021 mol dissolved in 1 ml of water), added simultaneously. After 17 h at 60° C., the reaction mixture is cooled down to room temperature, acidified to pH 5.5, concentrated in vacuo. The resulting solid is extracted with $CH_2Cl_2$ and concentrated in vacuo. A fraction (0.15 g) of the crude acid is purified by chromatography on silicagel (AcOEt/MeOH) to afford a 0.57 g of a 75/25 mixture of respectively 1-[(2-oxo-4-propylpyrrolidin-1-yl)methyl]-1H-imidazole-5-carboxylic acid a32 and 1-[(2-oxo-4-propylpyrrolidin-1-yl)methyl]-1H-imidazole-4-carboxylic acid a33 as an oil.

LC/MS ($MH^+$): 252.

12.2 Synthesis of benzyl 1-[(2-oxo-4-propylpyrrolidin-1-yl)methyl]-1H-imidazol-5-ylcarbamate 83

In a three necked flask, under argon, a solution of 1-[(2-oxo-4-propylpyrrolidin-1-yl)methyl]-1H-imidazole-5-carboxylic acid a32 (0.35 g, 1.39 mmol, predried by azeotropic distillation with toluene), diphenylphosphoryl azide (0.58 g, 2.1 mmol) and $Et_3N$ (0.29 ml) in toluene (5 ml) is heated at 40° C. with formation of $N_2$. The temperature is kept at 40° C. for 4 h and benzyl alcohol (0.301 g, 0.21 mmol) is added. The solution is heated at 90° C. for 1 h, cooled down to room temperature, stirred 48 h, heated at 90° C. for 1 h and concentrated in vacuo. The crude carbamate is purified by chromatography on silicagel ($CH_2Cl_2$/MeOH) to afford benzyl 1-[(2-oxo-4-propylpyrrolidin-1-yl)methyl]-1H-imidazol-5-ylcarbamate 83 (0.011 g) as an off white solid.

LC/MS ($MH^+$): 357.

Example 13

Synthesis of N-[(1-{[2-oxo-4-(3,4,5-trifluorophenyl)pyrrolidin-1-yl]methyl}-1H-imidazol-5-yl)methyl]propanamide 86

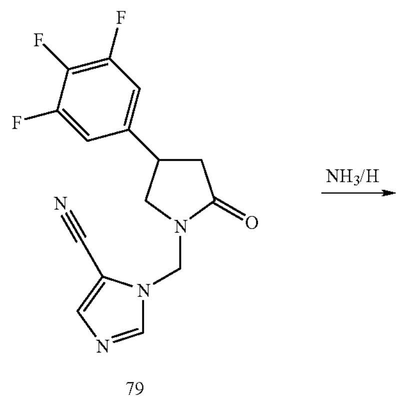

79 a34

-continued

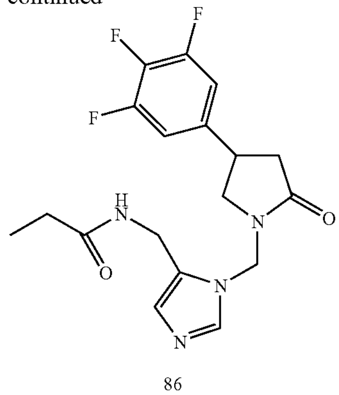

86

13.1 Synthesis of 1-(5-aminomethyl-imidazol-1-ylmethyl)-4-(3,4,5-trifluoro-phenyl)-pyrrolidin-2-one a34

In a 250 ml parr apparatus, Pd/C (0.1 g, 10% w/w) is added onto a solution of the enantiomerically pure (+)-1-{[2-oxo-4-(3,4,5-trifluorophenyl)pyrrolidin-1-yl]methyl}-1H-imidazole-4-carbonitrile 79 (0.2 g, 0.624 mmol) in $NH_3$/MeOH (3 M, 30 ml) and the suspension is stirred under an hydrogen pressure (50 psi) for 6 h. The reaction mixture is concentrated in vacuo, dissolved in AcOEt, dried over $MgSO_4$, filtered and concentrated in vacuo to afford 0.14 g of crude 1-(5-aminomethyl-imidazol-1-ylmethyl)-4-(3,4,5-trifluoro-phenyl)-pyrrolidin-2-one a34 which is used as such in the next step.

LC/MS ($MH^+$): 325.

13.2 Synthesis of N-[(1-{[2-oxo-4-(3,4,5-trifluorophenyl)pyrrolidin-1-yl]methyl}-1H-imidazol-5-yl)methyl]propanamide 86

In a three necked flask, under argon, propionyl chloride (0.0134 ml) is added to a solution of 1-(5-aminomethyl-imidazol-1-ylmethyl)-4-(3,4,5-trifluoro-phenyl)-pyrrolidin-2-one a34 (0.050 g, 0.15 mmol) and $Et_3N$ (0.29 ml) in $CH_2Cl_2$ (3 ml) at 0° C. After 1 h, the reaction mixture is quenched with ice-water, extracted with $CH_2Cl_2$, dried over $MgSO_4$, filtered and evaporated in vacuo. The crude reaction mixture is purified by chromatography on reverse phase silicagel to afford N-[(1-{[2 oxo-4-(3,4,5-trifluorophenyl)pyrrolidin-1-yl]methyl}-1H-imidazol-5-yl)methyl]propanamide 86(37.2 mg).

LC/MS ($MH^+$): 381.

Example 14

Synthesis of 1-[(2-oxo-4-propylpyrrolidin-1-yl)methyl]-1,3-dihydro-2H-benzimidazol-2-one 152

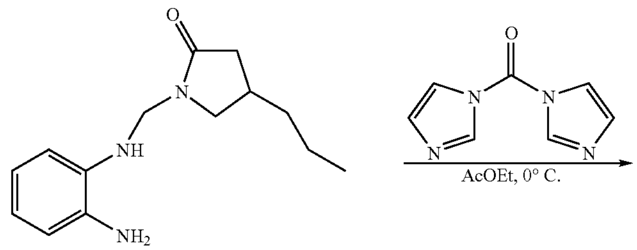

a29

-continued

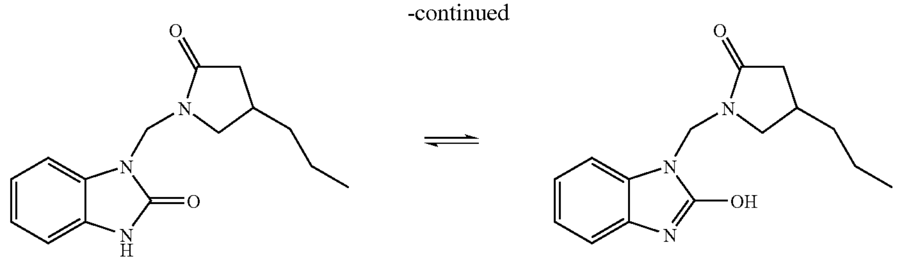

152

A solution of the dianiline a29 (0.3 g, 1.21 mmol) in AcOEt (10 ml) is slowly added, under agitation and inert atmosphere, to a solution of carbonyldiimidazole (2.43 mmol, 0.393 g) in AcOEt (30 ml) at 0° C. After 16 hours of reaction at this temperature, the crude organic layer is washed by HCl 1 N, then by a saturated NaCl solution, dried over $MgSO_4$, filtered and evaporated under reduced pressure. The residue is purified by chromatography on silicagel (dichloromethane/methanol/10% $NH_4OH$: 99/0.9/0.1), then recrystallized ($CH_2Cl_2$/hexane) to give 1-[(2-oxo-4-propylpyrrolidin-1-yl)methyl]-1,3-dihydro-2H-benzimidazol-2-one 152 a white solid (220 mg, 67%).

LC/MS ($MH^+$): 274.

Example 15

Synthesis of 1-[1-(1H-benzimidazol-1-yl)undecyl]-4-propylpyrrolidin-2-one 149

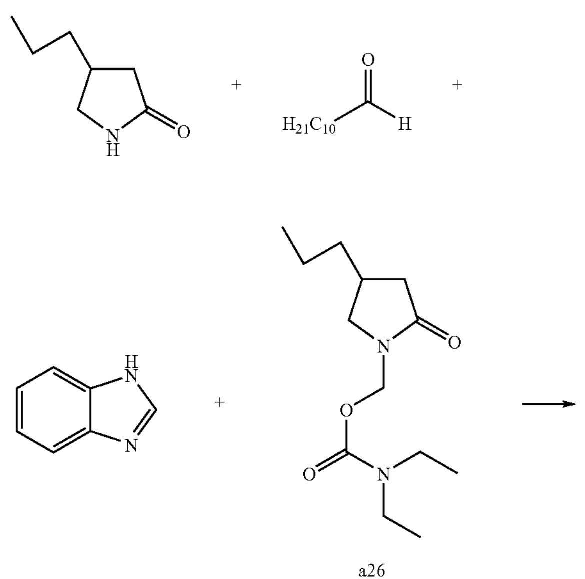

a26

-continued

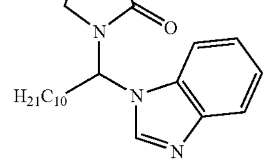

149

A mixture of 4-propyl-pyrrolidone (2 mmol, 254 mg), undecyl aldehyde (8 mmol, 1.651 ml), benzimidazole (2.2 mmol, 260 mg) and N,N-diethylcarbamate derivative a26 (0.2 mmol, 51 mg) in 2 ml of acetonitrile is heated for 1 hour in a microwave apparatus (CEM Discover, Pmax: 150 W, Tmax: 110° C.). After cooling and evaporation of solvent under reduce pressure, the crude product is purified by reverse phase chromatography (acetonitrile/water) to yield 1-[1-(1H-benzimidazol-1-yl)undecyl]-4-propylpyrrolidin-2-one 149 (135 mg, 17%).

Table I indicates the stereochemical information in the columns headed "configuration": the first one indicates whether a compound has no stereogenic center (achiral), is a pure enantiomer (pure), a racemate or is a mixture of two stereoisomers, possibly in unequal proportions (mixture); the second one contains the stereochemical assignment for the recognised center, following the IUPAC numbering used in the "IUPAC name" column. A number alone indicates the existence of both configurations at that center. A number followed by 'R' or 'S' indicates the known absolute configuration at that center. A number followed by '§' indicates the existence of only one but unknown absolute configuration at that center. The letter (A, B) in front is a way of distinguishing the various enantiomers of the same structure. Table 1 indicates also the type of salt, which was synthesized (if not the free base), the IUPAC name of the compound, the ion peak observed in mass spectroscopy and the optical rotation in the case of chiral compounds.

TABLE 1

| n° | Configuration | | Salt | IUPAC NAME | $MH^+$ ($M^+$−) | alphaD |
|---|---|---|---|---|---|---|
| 1 | achiral | — | | 1-(1H-imidazol-1-ylmethyl)pyrrolidin-2-one | 166 | |
| 2 | racemate | 4 | | 1-(1H-imidazol-1-ylmethyl)-4-phenylpyrrolidin-2-one | 242 | |
| 3 | racemate | 4 | | 4-(3-azido-2,4,6-trifluorophenyl)-1-(1H-imidazol-1-ylmethyl)pyrrolidin-2-one | 337 | |

TABLE 1-continued

| n° | Configuration | | Salt | IUPAC NAME | MH+ (M+−) | alphaD |
|---|---|---|---|---|---|---|
| 4 | racemate | 4 | | 1-(1H-imidazol-1-ylmethyl)-4-propylpyrrolidin-2-one | 208 | |
| 5 | racemate | 4 | | 4-(3-azido-2,4-difluorophenyl)-1-(1H-imidazol-1-ylmethyl)pyrrolidin-2-one | 319 | |
| 6 | pure | A-4§ | | (−)-4-(3-azido-2,4-difluorophenyl)-1-(1H-imidazol-1-ylmethyl)pyrrolidin-2-one | 319 | −15.43 |
| 7 | pure | B-4§ | | (+)-4-(3-azido-2,4-difluorophenyl)-1-(1H-imidazol-1-ylmethyl)pyrrolidin-2-one | 319 | +17.41 |
| 8 | racemate | 4 | | 1-[(2-oxo-4-propylpyrrolidin-1-yl)methyl]-1H-imidazole-4,5-dicarbonitrile | 258 | |
| 9 | racemate | 4 | | dimethyl 1-[(2-oxo-4-propylpyrrolidin-1-yl)methyl]-1H-imidazole-4,5-dicarboxylate | 324 | |
| 10 | racemate | 4 | | 1-[(2-ethyl-1H-imidazol-1-yl)methyl]-4-propylpyrrolidin-2-one | 236 | |
| 11 | racemate | 4 | | 1-[(2-isopropyl-1H-imidazol-1-yl)methyl]-4-propylpyrrolidin-2-one | 250 | |
| 12 | racemate | 4 | | 1-[(2-methyl-1H-imidazol-1-yl)methyl]-4-propylpyrrolidin-2-one | 222 | |
| 13 | racemate | 4 | | 1-[(2-phenyl-1H-imidazol-1-yl)methyl]-4-propylpyrrolidin-2-one | 284 | |
| 14 | racemate | 4 | | 4-propyl-1-[(2-propyl-1H-imidazol-1-yl)methyl]pyrrolidin-2-one | 250 | |
| 15 | pure | B-4§ | maleate | (+)-1-(1H-imidazol-1-ylmethyl)-4-propylpyrrolidin-2-one | 208 | +6.64 |
| 16 | pure | A-4§ | maleate | (−)-1-(1H-imidazol-1-ylmethyl)-4-propylpyrrolidin-2-one | 208 | −6.70 |
| 17 | racemate | 4 | | 4-(2-bromo-2,2-difluoroethyl)-1-(1H-imidazol-1-ylmethyl)pyrrolidin-2-one | 308/310 | |
| 18 | racemate | 4 | maleate | 4-(2,2-difluorovinyl)-1-(1H-imidazol-1-ylmethyl)pyrrolidin-2-one | 228 | |
| 19 | racemate | 4 | | 4-(3-chlorophenyl)-1-(1H-imidazol-1-ylmethyl)pyrrolidin-2-one | 276/278 | |
| 20 | racemate | 4 | | 1-{[2-(methylthio)-1H-imidazol-1-yl]methyl}-4-propylpyrrolidin-2-one | 254 | |
| 21 | mixture | 4 | | 1-{[2-(methylsulfinyl)-1H-imidazol-1-yl]methyl}-4-propylpyrrolidin-2-one | 270 | |
| 22 | racemate | 4 | | 1-[(2-tert-butyl-1H-imidazol-1-yl)methyl]-4-propylpyrrolidin-2-one | 264 | |
| 23 | achiral | — | HCl | 1-[1-(1H-imidazol-1-yl)cyclopropyl]pyrrolidin-2-one | 192 | |
| 24 | racemate | 4 | | 1-[(2-methyl-1H-imidazol-1-yl)methyl]-4-phenylpyrrolidin-2-one | 202 | |
| 25 | racemate | 4 | | 1-{[2-(methylsulfonyl)-1H-imidazol-1-yl]methyl}-4-propylpyrrolidin-2-one | 286 | |
| 26 | racemate | 4 | | 1-[(2-oxo-4-propylpyrrolidin-1-yl)methyl]-1H-imidazole-2-carboxamide | 251 | |
| 27 | racemate | 4 | maleate | 4-(4-fluorophenyl)-1-(1H-imidazol-1-ylmethyl)pyrrolidin-2-one | 260 | |
| 28 | racemate | 4 | maleate | 1-(1H-imidazol-1-ylmethyl)-4-(3,4,5-trifluorophenyl)pyrrolidin-2-one | 296 | |
| 29 | racemate | 4 | maleate | 4-(3-fluorophenyl)-1-(1H-imidazol-1-ylmethyl)pyrrolidin-2-one | 260 | |
| 30 | racemate | 4 | maleate | 4-(3,5-difluorophenyl)-1-(1H-imidazol-1-ylmethyl)pyrrolidin-2-one | 278 | |
| 31 | racemate | 4 | maleate | 4-(3,4-difluorophenyl)-1-(1H-imidazol-1-ylmethyl)pyrrolidin-2-one | 278 | |
| 32 | racemate | 4 | maleate | 4-(3-chloro-4-fluorophenyl)-1-(1H-imidazol-1-ylmethyl)pyrrolidin-2-one | 294/296 | |
| 33 | racemate | 4 | maleate | 4-(4-chlorophenyl)-1-(1H-imidazol-1-ylmethyl)pyrrolidin-2-one | 276 | |
| 34 | racemate | 4 | maleate | 1-(1H-imidazol-1-ylmethyl)-4-(2,3,4-trifluorophenyl)pyrrolidin-2-one | 296 | |
| 35 | racemate | 4 | maleate | 1-(1H-imidazol-1-ylmethyl)-4-(2,3,5-trifluorophenyl)pyrrolidin-2-one | 296 | |
| 36 | racemate | 4 | maleate | 1-(1H-imidazol-1-ylmethyl)-4-(2,4,5-trifluorophenyl)pyrrolidin-2-one | 296 | |
| 37 | racemate | 4 | HCl | 1-{[2-(hydroxymethyl)-1H-imidazol-1-yl]methyl}-4-propylpyrrolidin-2-one | 238 | |
| 38 | racemate | 4 | | methyl 1-[(2-oxo-4-propylpyrrolidin-1-yl)methyl]-1H-imidazole-2-carboxylate | 266 | |
| 39 | mixture | A-4§, 1 | | 1-[2-hydroxy-1-(1H-imidazol-1-yl)ethyl]-4-propylpyrrolidin-2-one | 238 | |
| 40 | racemate | 4 | | 1-[(2-nitro-1H-imidazol-1-yl)methyl]-4-(3,4,5-trifluorophenyl)pyrrolidin-2-one | 341 | |
| 41 | racemate | 4 | | 1-{[2-oxo-4-(3,4,5-trifluorophenyl)pyrrolidin-1-yl]methyl}-1H-imidazole-2-carbonitrile | 321 | |
| 42 | racemate | 4 | | 1-[(2-amino-1H-imidazol-1-yl)methyl]-4-propylpyrrolidin-2-one | 223 | |
| 43 | racemate | 4 | | 1-[(2,4-dichloro-1H-imidazol-1-yl)methyl]-4-(3,4,5-trifluorophenyl)pyrrolidin-2-one | 364/366/368 | |
| 44 | mixture | A-4§ (20%) B-4§ (80%) | | 1-[(5-chloro-1H-imidazol-1-yl)methyl]-4-(3,4,5-trifluorophenyl)pyrrolidin-2-one | 330/332 | |
| 45 | racemate | 4 | | 1-{[2-oxo-4-(3,4,5-trifluorophenyl)pyrrolidin-1-yl]methyl}-1H-imidazole-4-carbonitrile | 321 | |
| 46 | racemate | 4 | | 1-{[2-oxo-4-(3,4,5-trifluorophenyl)pyrrolidin-1-yl]methyl}-1H-imidazole-5-carbonitrile | 321 | |
| 47 | pure | B-4§ | | (+)-1-(1H-imidazol-1-ylmethyl)-4-phenylpyrrolidin-2-one | 242 | +0.264 |
| 48 | pure | A-4§ | | (−)-1-(1H-imidazol-1-ylmethyl)-4-phenylpyrrolidin-2-one | 242 | −0.299 |
| 49 | racemate | 4 | | 1-{[2-oxo-4-(2,3,5-trifluorophenyl)pyrrolidin-1-yl]methyl}-1H-imidazole-5-carbonitrile | (320) | |
| 50 | pure | A-4§ | | (−)-1-{[2-oxo-4-(2,3,4-trifluorophenyl)pyrrolidin-1-yl]methyl}-1H-imidazole-5-carbonitrile | (320) | −16.12 |
| 51 | pure | B-4§ | | (+)-1-{[2-oxo-4-(2,3,4-trifluorophenyl)pyrrolidin-1-yl]methyl}-1H-imidazole-5-carbonitrile | (320) | +16.51 |
| 52 | pure | B-4§ | | (−)-1-{[2-oxo-4-(2,3,4-trifluorophenyl)pyrrolidin-1-yl]methyl}-1H-imidazole-4-carbonitrile | (320) | −15.17 |
| 53 | pure | A-4§ | | (+)-1-{[2-oxo-4-(2,3,4-trifluorophenyl)-1-pyrrolidinyl]methyl}-1H-imidazole-4-carbonitrile | (320) | +16.03 |
| 54 | pure | A-4§ | | (−)-1-{[2-oxo-4-(3,4,5-trifluorophenyl)pyrrolidin-1-yl]methyl}-1H-imidazole-4-carbonitrile | (320) | −13.56 |
| 55 | pure | B-4§ | | (+)-1-{[2-oxo-4-(3,4,5-trifluorophenyl)pyrrolidin-1-yl]methyl}-1H-imidazole-4-carbonitrile | (320) | +15.02 |
| 56 | pure | A-4§ | | (+)-1-{[2-oxo-4-(2,4,5-trifluorophenyl)pyrrolidin-1-yl]methyl}-1H-imidazole-4-carbonitrile | 321 | +12.79 |
| 57 | pure | B-4§ | | (−)-1-{[2-oxo-4-(2,4,5-trifluorophenyl)pyrrolidin-1-yl]methyl}-1H-imidazole-4-carbonitrile | 321 | −11.70 |
| 58 | pure | A-4§ | | (+)-1-{[2-oxo-4-(2,4,5-trifluorophenyl)pyrrolidin-1-yl]methyl}-1H-imidazole-5-carbonitrile | 321 | +13.37 |
| 59 | pure | B-4§ | | (−)-1-{[2-oxo-4-(2,4,5-trifluorophenyl)pyrrolidin-1-yl]methyl}-1H-imidazole-5-carbonitrile | 321 | −12.91 |
| 60 | pure | A-4§ | | (−)-1-{[2-oxo-4-(2,3,5-trifluorophenyl)pyrrolidin-1-yl]methyl}-1H-imidazole-4-carbonitrile | 321 | −0.19 |

TABLE 1-continued

| n° | Configuration | | Salt | IUPAC NAME | MH⁺ (M⁺−) | alphaD |
|---|---|---|---|---|---|---|
| 61 | pure | A-4§ | | (−)-1-{[2-oxo-4-(3,4,5-trifluorophenyl)pyrrolidin-1-yl]methyl}-1H-imidazole-5-carbonitrile | (320) | −11.87 |
| 62 | pure | A-4§ | | 1-{[2-oxo-4-(2,3,5-trifluorophenyl)pyrrolidin-1-yl]methyl}-1H-imidazole-5-carbonitrile | (320) | |
| 63 | pure | B-4§ | | 1-{[2-oxo-4-(2,3,5-trifluorophenyl)pyrrolidin-1-yl]methyl}-1H-imidazole-5-carbonitrile | 321 | |
| 64 | racemate | 4 | | 1-[(5-methyl-2-phenyl-1H-imidazol-1-yl)methyl]-4-propylpyrrolidin-2-one | 298 | |
| 65 | racemate | 4 | | methyl 1-[(2-oxo-4-propylpyrrolidin-1-yl)methyl]-1H-imidazole-5-carboxylate | 266 | |
| 66 | racemate | 4 | | 1-[(5-methyl-1H-imidazol-1-yl)methyl]-4-propylpyrrolidin-2-one | 222 | |
| 67 | racemate | 4 | | 1-[(5-phenyl-1H-imidazol-1-yl)methyl]-4-propylpyrrolidin-2-one | 284 | |
| 68 | racemate | 4 | | 1-[(2-ethyl-5-methyl-1H-imidazol-1-yl)methyl]-4-propylpyrrolidin-2-one | 250 | |
| 69 | racemate | 4 | | 1-[(2,5-dimethyl-1H-imidazol-1-yl)methyl]-4-propylpyrrolidin-2-one | 236 | |
| 70 | racemate | 4 | | 1-[(2-chloro-1H-imidazol-1-yl)methyl]-4-(3,4,5-trifluorophenyl)pyrrolidin-2-one | 330/332 | |
| 71 | mixture | A-4§, 1 | | 1-[2-azido-1-(1H-imidazol-1-yl)ethyl]-4-propylpyrrolidin-2-one | 263 | |
| 72 | pure | A-4§ | | 1-[(4-chloro-1H-imidazol-1-yl)methyl]-4-(3,4,5-trifluorophenyl)pyrrolidin-2-one | 330/332 | |
| 73 | racemate | 4 | | 1-[(2-bromo-4,5-dichloro-1H-imidazol-1-yl)methyl]-4-propylpyrrolidin-2-one | 354/356/358 | |
| 74 | racemate | 4 | | 1-[(4,5-dichloro-1H-imidazol-1-yl)methyl]-4-propylpyrrolidin-2-one | 276/278 | |
| 75 | racemate | 4 | | 1-[(4,5-dichloro-2-methyl-1H-imidazol-1-yl)methyl]-4-propylpyrrolidin-2-one | 290/292 | |
| 76 | racemate | 4 | | 1-[(2-chloro-1H-imidazol-1-yl)methyl]-4-propylpyrrolidin-2-one | 242/244 | |
| 77 | racemate | 4 | | 4-propyl-1-[(2,4,5-tribromo-1H-imidazol-1-yl)methyl]pyrrolidin-2-one | 442/444/446 | |
| 78 | racemate | 4 | | 1-[(2-nitro-1H-imidazol-1-yl)methyl]-4-propylpyrrolidin-2-one | 253 | |
| 79 | pure | B-4§ | | (+)-1-{[2-oxo-4-(3,4,5-trifluorophenyl)pyrrolidin-1-yl]methyl}-1H-imidazole-5-carbonitrile | 321 | +12.57 |
| 80 | racemate | 4 | | 1-{[5-(hydroxymethyl)-1H-imidazol-1-yl]methyl}-4-propylpyrrolidin-2-one | 238 | |
| 81 | racemate | 4 | fumarate | 1-{[4-(hydroxymethyl)-1H-imidazol-1-yl]methyl}-4-propylpyrrolidin-2-one | 238 | |
| 82 | racemate | 4 | | N-methoxy-N-methyl-1-[(2-oxo-4-propylpyrrolidin-1-yl)methyl]-1H-imidazole-5-carboxamide | 295 | |
| 83 | racemate | 4 | | benzyl 1-[(2-oxo-4-propylpyrrolidin-1-yl)methyl]-1H-imidazol-5-ylcarbamate | 357 | |
| 84 | pure | A-4§ | | N-[(1-{[2-oxo-4-(3,4,5-trifluorophenyl)pyrrolidin-1-yl]methyl}-1H-imidazol-5-yl)methyl]acetamide | 367 | |
| 85 | pure | A-4§ | | N-[(1-{[2-oxo-4-(3,4,5-trifluorophenyl)pyrrolidin-1-yl]methyl}-1H-imidazol-5-yl)methyl]benzamide | 429 | |
| 86 | pure | A-4§ | | N-[(1-{[2-oxo-4-(3,4,5-trifluorophenyl)pyrrolidin-1-yl]methyl}-1H-imidazol-5-yl)methyl]propanamide | 381 | |
| 88 | racemate | 4 | | propyl {1-[(2-oxo-4-propylpyrrolidin-1-yl)methyl]-1H-imidazol-5-yl}carbamate | 309 | |
| 89 | achiral | — | | 1-(1H-benzimidazol-1-ylmethyl)pyrrolidin-2-one | 215 | |
| 90 | achiral | — | | 1-{[2-(methylthio)-1H-benzimidazol-1-yl]methyl}pyrrolidin-2-one | 262 | |
| 91 | racemate | 4 | $CF_3COOH$ | 1-(1H-benzimidazol-1-ylmethyl)-4-propylpyrrolidin-2-one | 258 | |
| 92 | racemate | 4 | | 1-[(2-methyl-1H-benzimidazol-1-yl)methyl]-4-propylpyrrolidin-2-one | 272 | |
| 93 | racemate | 4 | | 4-propyl-1-[(2-pyridin-2-yl-1H-benzimidazol-1-yl)methyl]pyrrolidin-2-one | 335 | |
| 94 | racemate | 4 | | 4-propyl-1-[(2-propyl-1H-benzimidazol-1-yl)methyl]pyrrolidin-2-one | 300 | |
| 95 | racemate | 4 | | 1-[(2-isopropyl-1H-benzimidazol-1-yl)methyl]-4-propylpyrrolidin-2-one | 300 | |
| 96 | racemate | 4 | | 4-propyl-1-{[2-(trifluoromethyl)-1H-benzimidazol-1-yl]methyl}pyrrolidin-2-one | 326 | |
| 97 | racemate | 4 | | 1-[(2-phenyl-1H-benzimidazol-1-yl)methyl]-4-propylpyrrolidin-2-one | 334 | |
| 98 | racemate | 4 | | 1-{[2-(methylthio)-1H-benzimidazol-1-yl]methyl}-4-propylpyrrolidin-2-one | 304 | |
| 99 | racemate | 4 | | 1-[(2-amino-1H-benzimidazol-1-yl)methyl]-4-propylpyrrolidin-2-one | 273 | |
| 100 | racemate | 4 | | N-{1-[(2-oxo-4-propylpyrrolidin-1-yl)methyl]-1H-benzimidazol-2-yl}guanidine | 315 | |
| 101 | racemate | 4 | | 1-{[2-(hydroxymethyl)-1H-benzimidazol-1-yl]methyl}-4-propylpyrrolidin-2-one | 288 | |
| 102 | racemate | 4 | | 1-{[2-(chloromethyl)-1H-benzimidazol-1-yl]methyl}-4-propylpyrrolidin-2-one | 306/308 | |
| 103 | racemate | 4 | | {1-[(2-oxo-4-propylpyrrolidin-1-yl)methyl]-1H-benzimidazol-2-yl}acetonitrile | 297 | |
| 104 | racemate | 4 | | 1-({2-[(4-chlorophenoxy)methyl]-1H-benzimidazol-1-yl}methyl)-4-propylpyrrolidin-2-one | 398/400 | |
| 105 | racemate | 4 | | 1-[(5-methoxy-1H-benzimidazol-1-yl)methyl]-4-propylpyrrolidin-2-one | 288 | |
| 106 | racemate | 4 | | 1-[(5-methyl-1H-benzimidazol-1-yl)methyl]-4-propylpyrrolidin-2-one | 272 | |
| 107 | racemate | 4 | | 1-[(5,6-dimethyl-1H-benzimidazol-1-yl)methyl]-4-propylpyrrolidin-2-one | 286 | |
| 108 | racemate | 4 | | 1-{[2-isopropyl-5-(trifluoromethyl)-1H-benzimidazol-1-yl]methyl}-4-propylpyrrolidin-2-one | 368 | |
| 109 | racemate | 4 | | 1-[(6-chloro-1H-benzimidazol-1-yl)methyl]-4-propylpyrrolidin-2-one | 292/294 | |
| 110 | racemate | 4 | $CF_3COOH$ | 1-[(2-oxo-4-propylpyrrolidin-1-yl)methyl]-2-propyl-1H-benzimidazole-5-carbonitrile | 325 | |
| 111 | racemate | 4 | $CF_3COOH$ | 2-benzyl-1-[(2-oxo-4-propylpyrrolidin-1-yl)methyl]-1H-benzimidazole-5-carbonitrile | 373 | |
| 112 | racemate | 4 | $CF_3COOH$ | 1-{[2-ethyl-5-(trifluoromethyl)-1H-benzimidazol-1-yl]methyl}-4-propylpyrrolidin-2-one | 354 | |
| 113 | racemate | 4 | $CF_3COOH$ | 1-{[2-benzyl-5-(trifluoromethyl)-1H-benzimidazol-1-yl]methyl}-4-propylpyrrolidin-2-one | 416 | |
| 114 | racemate | 4 | $CF_3COOH$ | 4-propyl-1-{[2-(1H-pyrrol-2-yl)-1H-benzimidazol-1-yl]methyl}pyrrolidin-2-one | 323 | |
| 115 | racemate | 4 | $CF_3COOH$ | 1-[(5-fluoro-2-propyl-1H-benzimidazol-1-yl)methyl]-4-propylpyrrolidin-2-one | 318 | |
| 116 | racemate | 4 | $CF_3COOH$ | 1-[(2-cyclohexyl-5-fluoro-1H-benzimidazol-1-yl)methyl]-4-propylpyrrolidin-2-one | 358 | |
| 117 | racemate | 4 | $CF_3COOH$ | 1-[(2-benzyl-6-methyl-1H-benzimidazol-1-yl)methyl]-4-propylpyrrolidin-2-one | 362 | |
| 118 | racemate | 4 | $CF_3COOH$ | 1-{[6-methyl-2-(1H-pyrrol-2-yl)-1H-benzimidazol-1-yl]methyl}-4-propylpyrrolidin-2-one | 337 | |
| 119 | racemate | 4 | $CF_3COOH$ | 1-[(6-methoxy-2-propyl-1H-benzimidazol-1-yl)methyl]-4-propylpyrrolidin-2-one | 330 | |

TABLE 1-continued

| n° | Configuration | | Salt | IUPAC NAME | MH+ (M+−) | alphaD |
|---|---|---|---|---|---|---|
| 120 | racemate | 4 | $CF_3COOH$ | 1-[(2-oxo-4-propylpyrrolidin-1-yl)methyl]-2-pyridin-3-yl-1H-benzimidazole-5-carbonitrile | 360 | |
| 121 | racemate | 4 | $CF_3COOH$ | 2-butyl-1-[(2-oxo-4-propylpyrrolidin-1-yl)methyl]-1H-benzimidazole-5-carbonitrile | 339 | |
| 122 | racemate | 4 | $CF_3COOH$ | 1-{[2-]2-(methythio)ethyl]-5-(trifluoromethyl)-1H-benzimidazol-1-yl]methyl}-4-propylpyrrolidin-2-one | 400 | |
| 123 | racemate | 4 | $CF_3COOH$ | 1-[(5-fluoro-2-isobutyl-1H-benzimidazol-1-yl)methyl]-4-propylpyrrolidin-2-one | 332 | |
| 124 | mixture | 4, 2 | $CF_3COOH$ | 1-{[5-fluoro-2-(2,4,4-trimethylpentyl)-1H-benzimidazol-1-yl]methyl}-4-propylpyrrolidin-2-one | 388 | |
| 125 | racemate | 4 | $CF_3COOH$ | 1-{[6-methyl-2-(2-phenylethyl)-1H-benzimidazol-1-yl]methyl}-4-propylpyrrolidin-2-one | 376 | |
| 126 | racemate | 4 | $CF_3COOH$ | 1-[(2-heptyl-6-methyl-1H-benzimidazol-1-yl)methyl]-4-propylpyrrolidin-2-one | 370 | |
| 127 | racemate | 4 | $CF_3COOH$ | 1-{[6-methoxy-2-(3,3,3-trifluoropropyl)-1H-benzimidazol-1-yl]methyl}-4-propylpyrrolidin-2-one | 384 | |
| 128 | racemate | 4 | $CF_3COOH$ | 2-cyclopropyl-1-[(2-oxo-4-propylpyrrolidin-1-yl)methyl]-1H-benzimidazole-5-carbonitrile | 323 | |
| 129 | racemate | 4 | $CF_3COOH$ | 1-[(2-oxo-4-propylpyrrolidin-1-yl)methyl]-2-pyridin-4-yl-1H-benzimidazole-5-carbonitrile | 360 | |
| 130 | racemate | 4 | $CF_3COOH$ | 1-[(2-oxo-4-propylpyrrolidin-1-yl)methyl]-2-(1H-pyrazol-3-yl)-1H-benzimidazole-5-carbonitrile | 349 | |
| 131 | racemate | 4 | $CF_3COOH$ | 1-[(2-cyclopropyl-5-fluoro-1H-benzimidazol-1-yl)methyl]-4-propylpyrrolidin-2-one | 316 | |
| 132 | racemate | 4 | $CF_3COOH$ | 1-{[2-(5-chloro-1,3-dimethyl-1H-pyrazol-4-yl)-5-fluoro-1H-benzimidazol-1-yl]methyl}-4-propylpyrrolidin-2-one | 404/406 | |
| 133 | racemate | 4 | $CF_3COOH$ | 1-[(5-fluoro-2-isopropyl-1H-benzimidazol-1-yl)methyl]-4-propylpyrrolidin-2-one | 318 | |
| 134 | racemate | 4 | $CF_3COOH$ | 1-{[2-(3-furyl)-6-methoxy-1H-benzimidazol-1-yl]methyl}-4-propylpyrrolidin-2-one | 354 | |
| 135 | racemate | 4 | $CF_3COOH$ | 1-[(6-methoxy-2-thien-3-yl-1H-benzimidazol-1-yl)methyl]-4-propylpyrrolidin-2-one | 370 | |
| 136 | racemate | 4 | $CF_3COOH$ | 1-{[6-methoxy-2-(1-methyl-1H-imidazol-2-yl)-1H-benzimidazol-1-yl]methyl}-4-propylpyrrolidin-2-one | 368 | |
| 137 | racemate | 4 | $CF_3COOH$ | 1-{[6-methoxy-2-(4-methyl-1H-imidazol-5-yl)-1H-benzimidazol-1-yl]methyl}-4-propylpyrrolidin-2-one | 368 | |
| 138 | racemate | 4 | $CF_3COOH$ | 1-[(2-cyclopropyl-6-methoxy-1H-benzimidazol-1-yl)methyl]-4-propylpyrrolidin-2-one | 328 | |
| 139 | racemate | 4 | $CF_3COOH$ | 1-{[2-(3,5-dimethylisothiazol-4-yl)-6-methoxy-1H-benzimidazol-1-yl]methyl}-4-propylpyrrolidin-2-one | 399 | |
| 140 | racemate | 4 | $CF_3COOH$ | 1-[(2-isopropyl-6-methoxy-1H-benzimidazol-1-yl)methyl]-4-propylpyrrolidin-2-one | 330 | |
| 141 | racemate | 4 | $CF_3COOH$ | 1-[(2-oxo-4-propylpyrrolidin-1-yl)methyl]-2-(1,2,3-thiadiazol-4-yl)-1H-benzimidazole-5-carbonitrile | 367 | |
| 142 | racemate | 4 | $CF_3COOH$ | 1-{[2-(1H-imidazol-2-yl)-5-(trifluoromethyl)-1H-benzimidazol-1-yl]methyl}-4-propylpyrrolidin-2-one | 392 | |
| 143 | mixture | 2, 4 | $CF_3COOH$ | 1-[(5-fluoro-2-tetrahydrofuran-2-yl-1H-benzimidazol-1-yl)methyl]-4-propylpyrrolidin-2-one | 346 | |
| 144 | racemate | 4 | $CF_3COOH$ | 1-{[5-fluoro-2-(2,2,2-trifluoroethyl)-1H-benzimidazol-1-yl]methyl}-4-propylpyrrolidin-2-one | 358 | |
| 145 | racemate | 4 | $CF_3COOH$ | 1-{[2-(4-chloro-1-methyl-1H-pyrazol-3-yl)-5-fluoro-1H-benzimidazol-1-yl]methyl}-4-propylpyrrolidin-2-one | 390/392 | |
| 146 | racemate | 4 | $CF_3COOH$ | 1-{[2-(1-ethylpropyl)-6-methoxy-1H-benzimidazol-1-yl]methyl}-4-propylpyrrolidin-2-one | 358 | |
| 147 | racemate | 4 | $CF_3COOH$ | 1-{[6-methoxy-2-(1-methyl-1H-pyrrol-2-yl)-1H-benzimidazol-1-yl]methyl}-4-propylpyrrolidin-2-one | 367 | |
| 148 | racemate | 4 | $CF_3COOH$ | 1-[(6-methoxy-1H-benzimidazol-1-yl)methyl]-4-propylpyrrolidin-2-one | 288 | |
| 149 | mixture | 4, 1 | | 1-[1-(1H-benzimidazol-1-yl)undecyl]-4-propylpyrrolidin-2-one | 398 | |
| 150 | racemate | 4 | | 6-methoxy-1-[(2-oxo-4-propylpyrrolidin-1-yl)methyl]-1,3-dihydro-2H-benzimidazol-2-one | 304 | |
| 151 | racemate | 4 | | 6-methyl-1-[(2-oxo-4-propylpyrrolidin-1-yl)methyl]-1,3-dihydro-2H-benzimidazol-2-one | 288 | |
| 152 | racemate | 4 | | 1-[(2-oxo-4-propylpyrrolidin-1-yl)methyl]-1,3-dihydro-2H-benzimidazol-2-one | 274 | |
| 153 | racemate | 4 | | 1-{[2-(2-furyl)-5-(trifluoromethyl)-1H-benzimidazol-1-yl]methyl}-4-propylpyrrolidin-2-one | 392 | |
| 154 | racemate | 4 | | 4-propyl-1-{[2-thien-2-yl-5-(trifluoromethyl)-1H-benzimidazol-1-yl]methyl}pyrrolidin-2-one | 408 | |
| 155 | racemate | 4 | | 1-{[2-(3-furyl)-5-(trifluoromethyl)-1H-benzimidazol-1-yl]methyl}-4-propylpyrrolidin-2-one | 392 | |
| 156 | racemate | 4 | | 1-{[2-cyclopropyl-5-(trifluoromethyl)-1H-benzimidazol-1-yl]methyl}-4-propylpyrrolidin-2-one | 366 | |
| 157 | racemate | 4 | | 4-propyl-1-{[2-(1H-pyrrol-2-yl)-5-(trifluoromethyl)-1H-benzimidazol-1-yl]methyl}pyrrolidin-2-one | 391 | |
| 158 | achiral | — | | 1-(1H-imidazol-1-ylmethyl)-1,3-dihydro-2H-indol-2-one | 214 | |
| 159 | achiral | — | | 5-bromo-1-(1H-imidazol-1-ylmethyl)-1,3-dihydro-2H-indol-2-one | 293 | |
| 160 | achiral | — | | 5-chloro-1-(1H-imidazol-1-ylmethyl)-1,3-dihydro-2H-indol-2-one | 248/250 | |
| 161 | achiral | — | | 4-fluoro-1-(1H-imidazol-1-ylmethyl)-1,3-dihydro-2H-indol-2-one | 232 | |
| 162 | achiral | — | | 4-chloro-1-(1H-imidazol-1-ylmethyl)-1,3-dihydro-2H-indol-2-one | 248/250 | |

TABLE 1-continued

| n° | Configuration | Salt | IUPAC NAME | MH⁺ (M⁺−) | alphaD |
|---|---|---|---|---|---|
| 163 | achiral | — | 1-(1H-imidazol-1-ylmethyl)-5-methyl-1,3-dihydro-2H-indol-2-one | (227) | |
| 164 | achiral | — | 1-(1H-imidazol-1-ylmethyl)-5-(2-methyl-1,3-thiazol-4-yl)-1,3-dihydro-2H-indol-2-one | 311 | |
| 165 | achiral | — | 1-[(2-oxo-2,3-dihydro-1H-indol-1-yl)methyl]-1H-imidazole-4-carbonitrile | (238) | |
| 166 | achiral | — | 1-[(2-oxo-2,3-dihydro-1H-indol-1-yl)methyl]-1H-imidazole-5-carbonitrile | (238) | |
| 167 | achiral | — | 1-(1H-benzimidazol-1-ylmethyl)-1,3-dihydro-2H-indol-2-one | 263 | |
| 168 | achiral | — | 1-[(5-chloro-2-oxo-2,3-dihydro-1H-indol-1-yl)methyl]-1H-imidazole-5-carbonitrile | 273 | |

Example 16

LBS Binding Assay

[LBS stands for Levetiracetam Binding Site cf. M. Noyer et al., Eur. J. Pharmacol. (1995), 286, 137-146.]

The inhibition constant ($K_i$) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant $K_i$ is proportional to the $IC_{50}$ and is calculated using the equation of Cheng and Prusoff (Cheng Y. et al., Biochem. Pharmacol. (1972), 22, 3099-3108).

The concentration range usually encompasses 6 log units with variable steps (0.3 to 0.5 log). Assays are performed in mono- or duplicate, each $K_i$ determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The homogenate is centrifuged at 30,000 g for 15 min. The crude membrane pellet obtained is resuspended in 50 mmol/l Tris-HCl (pH 7.4), (buffer B) and incubated 15 min at 37° C., centrifuged at 30,000 g for 15 min and washed twice with the same buffer. The final pellet is resuspended in buffer A at a protein concentration ranging from 15 to 25 mg/ml and stored in liquid nitrogen.

Membranes (150-200 μg of protein/assay) are incubated at 4° C. for 120 min in 0.5 ml of a 50 mmol/l Tris-HCl buffer (pH 7.4) containing 2 mmol/l $MgCl_2$, 1 to 2 $10^{-9}$ mol/l of [$^3$H]-2-[4-(3-azidophenyl)-2-oxo-1-pyrrolidinyl]butanamide and increasing concentrations of the test substance. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a β-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors, which obey the law of mass.

Example 17

Animal Model of Sound-Susceptible Mice

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consisted of several groups, one group receiving the vehicle control and the other groups different doses of the test-compound. The compounds are administered intraperitoneally 60 minutes before the induction of audiogenic seizures. The range of the doses administered had a logarithmic progression, generally between $1.0\times10^{-5}$ mol/kg and $1.0\times10^{-3}$ mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an $ED_{50}$ value, i.e. the dose producing 50% protection relative to the control group, together with 95% confidence limits, was calculated using a Probit Analysis (SAS/STAT® Software, version 6.09, PROBIT procedure) of the proportions of protected mice for each of the 3 phases of the seizure activity.

Example 18

Figure 2A:
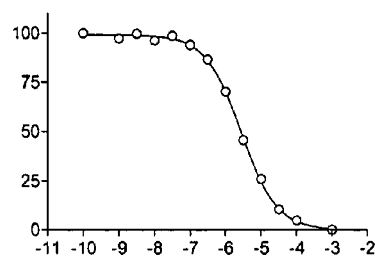
FIGS. 2*a* and 2*b* depict competition binding curves showing that compound 7 binds to LBS with about 30 fold higher affinity than levetiracetam. Y-axis represents [$^3H$]-compound 7 bound (% of control) and X-axis represents Log [Drug] (M). Test drugs are levetiracetam (2a) and compound 7 (2b).
Figure 2B:
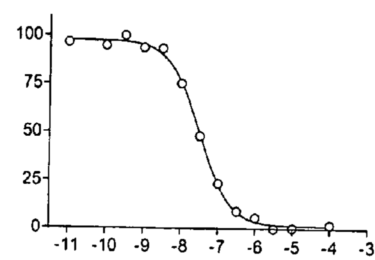

Development of [$^3$H]-(+)-4-(3-azido-2,4-difluorophenyl)-1-(1H-imidazol-1-ylmethyl)pyrrolidin-2-one ([$^3$H]-compound 7) for Binding Studies Levetiracetam or L059 has been shown to bind to a specific binding site located preferentially in the brain (levetiracetam binding site or LBS: Noyer M. et al., Euro. J. Pharmacol. (1995), 286, 137-146). However, [$^3$H]-L059 displayed only micromolar affinity for this site, making it unsuitable for in depth characterization. This example describes the binding properties of [$^3$H]-compound 7. Binding experiments were conducted on crude rat brain membranes at 4° C. as described in Noyer M. et al. (Euro. J. Pharmacol. (1995), 286, 137-146). Incubation time for equilibrium studies was 120 min. [$^3$H]-compound 7 (25 Ci/mmol) was used at a concentration of 0.4 nM in 0.5 ml of a Tris-HCl (pH 7.4) buffer containing 2 mM $Mg^{2+}$. FIG. 1 shows that the saturation binding curves of [$^3$H]-compound 7 were compatible with the labeling of a homogeneous population of binding sites. $K_D$ and $B_{max}$ were respectively 13 nM and 9 pmol/mg protein. The $B_{max}$ being similar to the value estimated using [$^3$H]-L059 as radioligand in similar membrane preparations (5 pmol/mg protein). Competition binding curves showed that compound 7 binds to LBS with about 30 fold higher affinity than L059 (FIG. 2). The pKi of compound 7 (7.5) agrees well with the $K_D$ of [$^3$H]-compound 7 as determined by the saturation binding curve (FIG. 2).

Example 19

Photolabelling of LBS in Rat Brain Membranes Using [$^3$H]-(+)-4-(3-azido-2,4-difluorophenyl)-1-(1H-imidazol-1-ylmethyl)pyrrolidin-2-one ([$^3$H]-compound 7)

Figure 3:
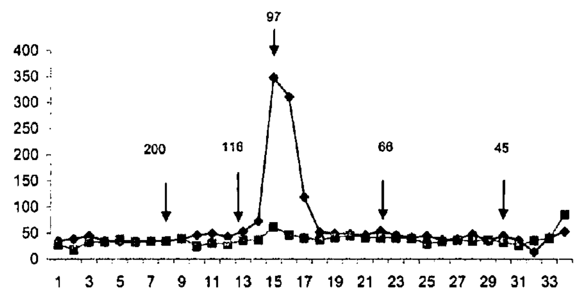
FIG. 3 depicts gel electrophoresis of membrane proteins labelled by [$^3$H]-compound 7. Y-axis represents the radioactivity (DPM) in gel slices and X-axis represents the gel slice number. Each number and arrow in the graph represents the position and the size in kilodaltons of molecular weight standards.

This example provides a photoactivable ligand for labelling SV2A/LBS and its detection in biological samples. This ligand was designed to cross-link to the LBS/SV2A with an azidophenyl motif capable of forming a covalent complex with the protein upon UV light irradiation. FIG. 3 shows a typical experiment with [$^3$H]-compound 7 where irradiated rat brain membrane are loaded onto SDS-PAGE. After gel slicing and radioactivity counting, it was found that the radiolabel incorporates into a 90-kDa protein.

Example 20

Screening Assays for the Discovery of More Potent LBS/SV2 Ligands

Figure 4:
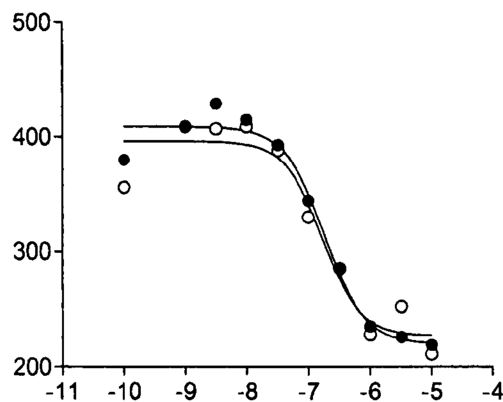
FIG. 4 depicts an $IC_{50}$ plot of compound 7 using SPA beads coated with rat brain membranes and compound 7. Y-axis represents [$^3$H]-compound 7 bound (DPM/assay) and X-axis represents Log [Drug] (M). The test drug is compound 7 (duplicate experiment).

In order to identify compounds or agents which interact with LBS/SV2 proteins, SV2 transfected cells or brain membranes are exposed to a potential binding partner from a proprietary compound library and labelled compound 7. Cells or membranes are incubated at 4° C. for 2 hours, and then rapidly filtered and transferred to scintillation vials with scintillation fluid and counted for $^3$H decay emission. Compounds which are found to compete with the probe for binding to the LBS/SV2 are subject to further analysis using dose-response curves and $IC_{50}$ determination. Alternatively, labelled compound 7 can be used in scintillation proximity assay (SPA, Amersham Biosciences) with microspheres coated with SV2A/LBS-containing membranes. Typical HTS assays are performed in 96-well plates with beads coated with rat brain membranes. Briefly, competition binding of [$^3$H]-compound 7 (9 nM) to rat brain membranes (100 μg) was carried out using WGA SPA bead and test drugs in 200 μl total assay volume at 25° C. for 2 h in 50 mM Tris-HCl (pH 7.4) containing 2 mM $MgCl_2$ and 1% DMSO followed by beta counting. Nonspecific binding was measured in the presence of 1 mM L059. Data in FIG. 4 showed potency profiles of compound 7 obtained with [$^3$H]-compound 7 and coated beads in 96-well plates which are in line with studies using filtration binding assays in 1% DMSO.

Example 21

Figure 5:
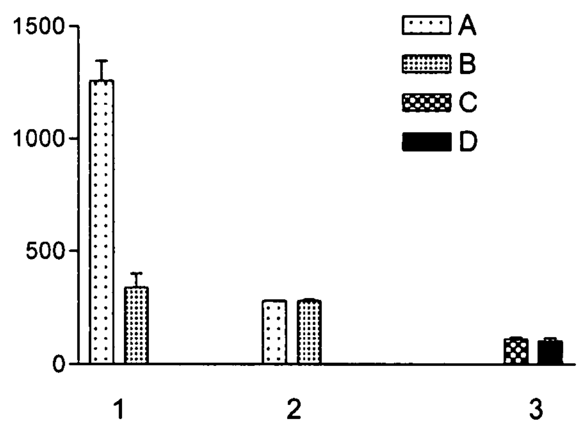
FIG. 5 depicts the binding of two radioligands ([$^3$H]-compound 7 and [$^3$H]-compound A against transiently transfected COS-7 cells with SV2C. The Y axis represents CPM bound. On the X axis, the first pair of bars (labeled "1") represents the specific binding to cells expressing hSV2C using [$^3$H]-compound 7 as a probe (A=[$^3$H]-alone, B=[$^3$H]-compound 7 plus excess levetiracetam, which displaces the specifically bound probe). The second pair of bars (labeled "2") is the same experiment in untransfected cells (A and B have the same meaning as above), which shows no specific binding. The last pair of bars (labeled "3"), shows the absence of specific binding to cells transfected with hSV2C using the probe [$^3$H]-compound Z (C=[$^3$H]-compound Z alone, and D=[$^3$H]-compound Z plus excess levetiracetam).
Figure 6:
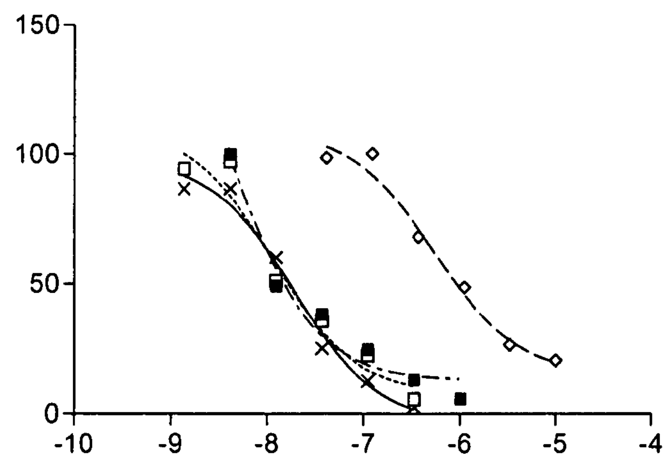
FIG. 6 depicts an $IC_{50}$ plot comparing the binding of two different ligands to human SV2A and SV2C using [$^3$H]-compound 7 as a radioligand. The Y-axis represents [$^3$H]-compound 7 bound (% of control) and X-axis represents Log [Drug] (M). Depicted are the $IC_{50}$ curves of compound 7 binding to hSV2A (x) and hSV2C (□), and compound Z binding to hSV2A (■) and hSV2C (◇). Note the different affinities of compound Z to hSV2A and hSV2C, and the equivalent affinities of compound 7 to hSV2A and hSV2C (●).

SV2C Binds Selectively to [$^3$H]-(+)-4-(3-azido-2,4-difluorophenyl)-1-(1H-imidazol-1-ylmethyl)pyrrolidin-2-one ([$^3$H]-compound 7) Compared to SV2A Testing of binding of two [$^3$H]-L059 derivatives with similar affinity for human SV2A, shows a differential binding towards SV2C. [$^3$H]-compound Z shows a lack of binding to SV2C expressed in COS-7 cells under standard conditions (see above), where it binds well to SV2A. In contrast, [$^3$H]-compound 7 binds well to SV2C expressed under the same conditions (FIG. 5). This differential binding of the two ligands to SV2C is confirmed by measuring the $IC_{50}$s of the unlabelled ligands against SV2A and SV2C using [$^3$H]-compound 7 as the labeled probe (FIG. 6). As can be seen, compound Z and compound 7 show similar affinities to SV2A. In addition, compound 7 shows similar affinities to SV2A and SV2C. However, compound Z shows a much weaker affinity to SV2C than it does to SV2A. This confirms that labeled-compound Z has poor affinity for utilizing as a probe against SV2C, and that labeled-compound 7 is a preferred probe to utilize in screening against SV2C.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

The invention claimed is:

1. A compound having formula I, geometrical isomers (including cis and trans, Z and E isomers), enantiomers, diastereoisomers and mixtures thereof (including all possible mixtures of stereoisomers), or pharmaceutically acceptable salts thereof, (I)

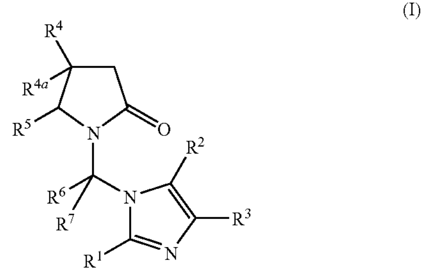

wherein $R^1$ is hydrogen, $C_{1-20}$ alkyl, $C_{3-8}$ cycloalkyl, halogen, hydroxy, alkoxy, aryloxy, ester, amido, cyano, nitro, amino, guanidine, amino derivative, alkylthio, arylthio, alkylsulfonyl, arylsulfonyl, alkylsulfinyl, arylsulfinyl, aryl or heterocycle;

$R^2$ and $R^3$ form together with the imidazole ring the following 1H— benzimidazole cycle

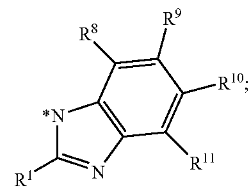

$R^4$ is $C_{1-20}$ alkyl, $C_{2-12}$ alkenyl, $C_{2-12}$ alkynyl, or aryl;

$R^{4a}$ is hydrogen;

$R^5$ is hydrogen;

$R^6$ is hydrogen;

$R^7$ is hydrogen;

$R^8$ is hydrogen, halogen, nitro, cyano, $C_{1-20}$ alkyl or alkoxy;

$R^9$ is hydrogen, $C_{1-20}$ alkyl, halogen, hydroxy, alkoxy, aryloxy, ester, amido, cyano, nitro, amino, alkylthio, arylthio, alkylsulfonyl, arylsulfonyl, alkylsulfinyl or arylsulfinyl;

$R^{10}$ is hydrogen, $C_{1-20}$ alkyl, halogen, hydroxy, alkoxy, aryloxy, ester, amido, cyano, nitro, amino, alkylthio, arylthio, alkylsulfonyl, arylsulfonyl, alkylsulfinyl or arylsulfinyl; and $R^{11}$ is hydrogen, halogen, nitro, cyano, $C_{1-20}$ alkyl or alkoxy.

2. A compound having formula I, geometrical isomers (including cis and trans, Z and E isomers), enantiomers, diastereoisomers and mixtures thereof (including all possible mixtures of stereoisomers), or pharmaceutically acceptable salts thereof,

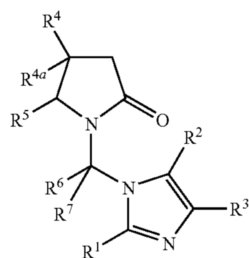

wherein $R^1$ is hydrogen, $C_{1-20}$ alkyl, $C_{3-8}$ cycloalkyl, halogen, hydroxy, ester, amido, cyano, nitro, amino, guanidine, alkylthio, alkylsulfonyl, alkylsulfinyl, aryl or heterocycle;

$R^2$ and $R^3$ form together with the imidazole ring the following 1H— benzimidazole cycle

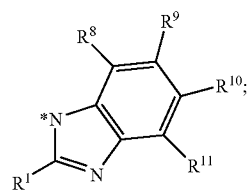

$R^4$ is $C_{1-20}$ alkyl, $C_{2-12}$ alkenyl or aryl;

$R^{4a}$ is hydrogen;

$R^5$ is hydrogen;

$R^6$ is hydrogen;

$R^7$ is hydrogen;

$R^8$ is hydrogen;

$R^9$ is hydrogen, $C_{1-20}$ alkyl, halogen or alkoxy;

$R^{10}$ is hydrogen, $C_{1-20}$ alkyl, halogen or cyano; and $R^{11}$ is hydrogen.

3. A compound according to claim 2, wherein $R^1$ is hydrogen; methyl; ethyl; i-propyl; n-propyl; cyclopropyl; n-butyl; i-butyl; t-butyl; 1-ethylpropyl; 2,4,4-trimethylpentyl; hydroxymethyl; chloromethyl; trifluoromethyl; 2,2,2-trifluoroethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl or 1H-imidazol-2-yl.

4. A compound according to claim 2, wherein $R^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl or 3-azido-2,4,6-trifluorophenyl.

5. A compound according to claim 2, wherein $R^8$ is hydrogen;

$R^9$ is selected from hydrogen; methyl; chloro; methoxy;

$R^{10}$ is selected from methyl; hydrogen; trifluoromethyl; fluoro; cyano or methoxy;

$R^{11}$ is hydrogen.

6. A compound according to claim 2, wherein $R^1$ is selected from hydrogen; methyl; ethyl; i-propyl; n-propyl; n-butyl; methylthio; nitro; cyano; amino; chloro; and 1H-pyrrol-2-yl;

$R^8$ is hydrogen;

$R^9$ is hydrogen;

$R^{10}$ is selected from hydrogen; trifluoromethyl; fluoro; cyano;

$R^{11}$ is hydrogen;

$R^4$ is selected from hydrogen; n propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; and 3-azido-2,4-difluorophenyl;

$R^{4a}$ is hydrogen; and $R^5$ is hydrogen.

7. A compound according to claim 2, selected from the group:

1-(1H-benzimidazol-1-ylmethyl)-4-propylpyrrolidin-2-one;

1-[(2-methyl-1H-benzimidazol-1-yl)methyl]-4-propylpyrrolidin-2-one;

4-propyl-1-[(2-propyl-1H-benzimidazol-1-yl)methyl]pyrrolidin-2-one;

1-[(2-isopropyl-1H-benzimidazol-1-yl)methyl]-4-propylpyrrolidin-2-one;

4-propyl-1-{[2-(trifluoromethyl)-1H-benzimidazol-1-yl]methyl}pyrrolidin-2-one;

1-{[2-(methylthio)-1H-benzimidazol-1-yl]methyl}-4-propylpyrrolidin-2-one;

1-[(2-amino-1H-benzimidazol-1-yl)methyl]-4-propylpyrrolidin-2-one;

1-{[2-(chloromethyl)-1H-benzimidazol-1-yl]methyl}-4-propylpyrrolidin-2-one;

{1-[(2-oxo-4-propylpyrrolidin-1-yl)methyl]-1H-benzimidazol-2-yl}acetonitrile;

1-[(5-methyl-1H-benzimidazol-1-yl)methyl]-4-propylpyrrolidin-2-one;

1-[(5,6-dimethyl-1H-benzimidazol-1-yl)methyl]-4-propylpyrrolidin-2-one;

1-{[2-isopropyl-5-(trifluoromethyl)-1H-benzimidazol-1-yl]methyl}-4-propylpyrrolidin-2-one;

1-[(6-chloro-1H-benzimidazol-1-yl)methyl]-4-propylpyrrolidin-2-one;

1-[(2-oxo-4-propylpyrrolidin-1-yl)methyl]-2-propyl-1H-benzimidazole-5-carbonitrile;

1-{[2-ethyl-5-(trifluoromethyl)-1H-benzimidazol-1-yl]methyl}-4-propylpyrrolidin-2-one;

4-propyl-1-{[2-(1H-pyrrol-2-yl)-1H-benzimidazol-1-yl]methyl}pyrrolidin-2-one;

1-[(5-fluoro-2-propyl-1H-benzimidazol-1-yl)methyl]-4-propylpyrrolidin-2-one;

1-{[6-methyl-2-(1H-pyrrol-2-yl)-1H-benzimidazol-1-yl] methyl}-4-propylpyrrolidin-2-one;

1-[(6-methoxy-2-propyl-1H-benzimidazol-1-yl)methyl]-4-propylpyrrolidin-2-one;

2-butyl-1-[(2-oxo-4-propylpyrrolidin-1-yl)methyl]-1H-benzimidazole-5-carbonitrile;

1-{[2-[2-(methylthio)ethyl]-5-(trifluoromethyl)-1H-benzimidazol-1-yl]methyl}-4-propylpyrrolidin-2-one;

1-[(5-fluoro-2-isobutyl-1H-benzimidazol-1-yl)methyl]-4-propylpyrrolidin-2-one;

1-{[5-fluoro-2-(2,4,4-trimethylpentyl)-1H-benzimidazol-1-yl]methyl}-4-propylpyrrolidin-2-one;

2-cyclopropyl-1-[(2-oxo-4-propylpyrrolidin-1-yl)methyl]-1H-benzimidazole-5-carbonitrile;

1-[(2-oxo-4-propylpyrrolidin-1-yl)methyl]-2-(1H-pyrazol-3-y1)-1H-benzimidazole-5-carbonitrile;

1-[(2-cyclopropyl-5-fluoro-1H-benzimidazol-1-yl)methyl]-4-propylpyrrolidin-2-one;

1-[(5-fluoro-2-isopropyl-1H-benzimidazol-1-yl)methyl]-4-propylpyrrolidin-2-one;

1-{[2-(3-furyl)-6-methoxy-1H-benzimidazol-1-yl]methyl}-4-propylpyrrolidin-2-one;

1-[(2-cyclopropyl-6-methoxy-1H-benzimidazol-1-yl)methyl]-4-propylpyrrolidin-2-one;

1-[(2-isopropyl-6-methoxy-1H-benzimidazol-1-yl)methyl]-4-propylpyrrolidin-2-one;

1-[(2-oxo-4-propylpyrrolidin-1-yl)methyl]-2-(1,2,3-thiadiazol-4-yl)-1H-benzimidazole-5-carbonitrile;

1-{[2-(1H-imidazol-2-yl)-5-(trifluoromethyl)-1H-benzimidazol-1-yl]methyl}-4-propylpyrrolidin-2-one;

1-{[5-fluoro-2-(2,2,2-trifluoroethyl)-1H-benzimidazol-1-yl]methyl}-4-propylpyrrolidin-2-one;

1-{[2-(1-ethylpropyl)-6-methoxy-1H-benzimidazol-1-yl] methyl}-4-propylpyrrolidin-2-one;

1-{[6-methoxy-2-(1-methyl-1-pyrrol-2-yl)-1H-benzimidazol-1-yl]methyl}-4-propylpyrrolidin-2-one;

1-{[2-(2-furyl)-5-(trifluoromethyl)-1H-benzimidazol-1-yl]methyl}-4-propylpyrrolidin-2-one;

4-propyl-1-{[2-thien-2-yl-5-(trifluoromethyl)-1H-benzimidazol-1-yl]methyl}pyrrolidin-2-one;

1-{[2-(3-furyl)-5-(trifluoromethyl)-1H-benzimidazol-1-yl]methyl}-4-propylpyrrolidin-2-one;

1-{[2-cyclopropyl-5-(trifluoromethyl)-1H-benzimidazol-1-yl]methyl}-4-propylpyrrolidin-2-one; and 4-propyl-1-{[2-(1H-pyrrol-2-yl)-5-(trifluoromethyl)-1H-benzimidazol-1-yl]methyl}pyrrolidin-2-one.

8. A compound according to claim 2, selected from the group:

1-[(2-oxo-4-propylpyrrolidin-1-yl)methyl]-2-propyl-1H-benzimidazole-5-carbonitrile;

1-{[2-ethyl-5-(trifluoromethyl)-1H-benzimidazol-1-yl] methyl}-4-propylpyrrolidin-2-one; 4-propyl-1-{[2-(1H-pyrrol-2-yl)-1H-benzimidazol-1-yl] methyl}pyrrolidin-2-one;

1-[(5-fluoro-2-propyl-1H-benzimidazol-1-yl)methyl]-4-propylpyrrolidin-2-one;

2-butyl-1-[(2-oxo-4-propylpyrrolidin-1-yl)methyl]-1H-benzimidazole-5-carbonitrile; and 1-[(5-fluoro-2-isopropyl-1H-benzimidazol-1-yl)methyl]-4-propylpyrrolidin-2-one.

9. A pharmaceutical composition comprising an effective amount of a compound according to claim 2 in combination with a pharmaceutically acceptable diluent or carrier.

* * * * *